US011054425B2

(12) United States Patent
Albert et al.

(10) Patent No.: US 11,054,425 B2
(45) Date of Patent: *Jul. 6, 2021

(54) SYSTEM AND METHOD FOR IDENTIFICATION AND CHARACTERIZATION OF TRANSGLUTAMINASE SPECIES

(71) Applicant: Roche Sequencing Solutions, Inc., Pleasanton, CA (US)

(72) Inventors: Thomas Albert, Danville, CA (US); Frank Bergmann, Iffeldorf (DE); Victor Lyamichev, Madison, WI (US); Mohamed Yosry Hassan Mohamed, Munich (DE); Tobias Oelschlaegel, Munich (DE); Jigar Patel, Verona, WI (US); Michael Schraeml, Penzberg (DE); Wojtek Steffen, Murnau (DE); Thomas Streidl, Seeshaupt (DE)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/785,406

(22) Filed: Feb. 7, 2020

(65) Prior Publication Data

US 2020/0249231 A1 Aug. 6, 2020

Related U.S. Application Data

(63) Continuation-in-part of application No. 15/974,385, filed on May 8, 2018, now Pat. No. 10,788,495, which is a continuation of application No. 14/973,472, filed on Dec. 17, 2015, now Pat. No. 10,006,915.

(60) Provisional application No. 62/260,162, filed on Nov. 25, 2015, provisional application No. 62/094,495, filed on Dec. 19, 2014.

(51) Int. Cl.
*G01N 33/573* (2006.01)
*C12N 9/10* (2006.01)
*C07K 1/107* (2006.01)
*C07K 7/06* (2006.01)

(52) U.S. Cl.
CPC ......... *G01N 33/573* (2013.01); *C07K 1/1075* (2013.01); *C07K 7/06* (2013.01); *C12N 9/1044* (2013.01); *C12Y 203/01013* (2013.01); *G01N 2333/91085* (2013.01)

(58) Field of Classification Search
None
See application file for complete search history.

(56) References Cited

U.S. PATENT DOCUMENTS

| | | | |
|---|---|---|---|
| 10,006,915 B2* | 6/2018 | Albert | C07K 7/06 |
| 2009/0117640 A1 | 5/2009 | Norskov-Lauritsen et al. | |
| 2009/0318349 A1 | 12/2009 | Hu et al. | |
| 2012/0190561 A1 | 7/2012 | Wildt et al. | |
| 2018/0252714 A1* | 9/2018 | Albert | C07K 1/1075 |

FOREIGN PATENT DOCUMENTS

| | | |
|---|---|---|
| CA | 2402563 A1 | 7/2001 |
| CA | 2902841 A1 | 10/2014 |
| WO | 2007/020290 A1 | 2/2007 |
| WO | 2008/020074 A1 | 2/2008 |
| WO | 2012059882 A2 | 5/2012 |
| WO | 2013163162 A1 | 10/2013 |
| WO | 2013130953 A2 | 10/2014 |

OTHER PUBLICATIONS

Shikhman A R et al: "Cytokeratin Peptide SFGSGFGGGY Mimics N-Acetyl-Beta-D-Glucosamine in Reaction With Antibodies and Lectins, and Induced In Vivo Anti-Carbohydrate Antibody Response", The Journal of Immunology, The American Association of Immunologists, US, vol. 153, Jan. 1, 1994 (Jan. 1, 1994), pp. 5593-5606, XP000941613, ISSN: 0022-1767.

Karen Chao Butterfield et al: "Identification and Sequence Composition Characterization of Chondroitin Sulfate-Binding Peptides through Peptide Array Screening", Biochemistry, vol. 49, No. 7, Feb. 23, 2010 (Feb. 23, 2010), pp. 1549-1555, XP055067897, ISSN: 0006-2960, DOI: 10.1021/bi9021044.

Yuriy Rebets et al: "Complete genome sequence of producer of the glycopeptide antibiotic Auleximycin Kutzneria albida DSM 43870T, a representative of minor genus of Pseudonocardiaceae", BMC Genomics, Biomed Central Ltd, London, UK, vol. 15, No. 1, Oct. 10, 2014 (Oct. 10, 2014), p. 885, XP021200656, ISSN: 1471-2164, DOI: 10.1186/1471-2164-15-885.

Hemung, B.—O. et al., Reactivity of Fish and Microbial Transglutaminases on Glutaminyl Sites of Peptides Derived from Threadfin Bream Myosin, J. Agric. Food Chern., (2008), pp. 7510-7516, vol. 56 No. 16.

Kuramoto, K. et al., Phage-displayed peptide library screening for preferred human substrate peptide sequences for transglutaminase 7, Archives of Biochemistry and Biophysics, (2013), pp. 138-143, vol. 537 Issue 1.

(Continued)

*Primary Examiner* — Brian Gangle
(74) *Attorney, Agent, or Firm* — Eric Grant Lee; Daniel E. Agnew

(57) ABSTRACT

In one aspect, the present disclosure provides a system and method for the identification and characterization of a transglutaminase. Further, the present disclosure provides transglutaminase enzymes for forming isopeptide bonds, methods of forming isopeptide bonds in the presence of transglutaminases, and substrate tags for use with transglutaminases. In another aspect, the present disclosure provides glutamine-containing substrates (or Q-tag substrates) that are more resistant to proteases/clipping and therefore, more stable, than other Q-tag substrates, and their uses in substrate tags for cross-linking to an amine-donor tag via an isopeptide bond mediated by a microbial transglutaminase.

31 Claims, 27 Drawing Sheets
(10 of 27 Drawing Sheet(s) Filed in Color)
Specification includes a Sequence Listing.

(56) References Cited

OTHER PUBLICATIONS

Sugimura, Y. et al., Identification of preferred substrate sequences of microbial transglutaminase from Streptomyces mobaraensis using a phage-displayed peptide library, Archives of Biochemistry and Biophysics, (2008), pp. 379-383, vol. 477 Issue 2.

International Search Report and Written Opinion dated Mar. 14, 2016 in corresponding PCT Application No. PCT/US2015/066491 filed Dec. 17, 2015, pp. 1-16.

Strop, P., Versatility of Microbial Transglutaminase, Bioconjugate Chem., 2014, 25 (5), pp. 855-862, DOI: 10.1021/bc500099v, Publication Date (Web): Apr. 2, 2014.

Oteng-Pabi, S. K. and Keillor, J. W., Continuous enzyme-coupled assay for microbial transglutaminase activity, Analytical Biochemistry 2013, 441 (2), pp. 169-173.

Steffen, et al., "Discovery of a microbial transglutaminase enabling highly site-specific labeling of proteins," J. Biol. Chem. 292(38):15622-15635 (2017).

Butterfield, et al., "Identification and Sequence Composition Characterization of Chondroitin Sulfate-Binding Peptides through Peptide Array Screening," Biochemistry 49:1549-1555 (2010).

Rebets, et al., "Complete genome sequence of producer of glycopeptide antibiotic Aculeximycin Kutzneria albida DSM 43870T, a representative of minor genus of Pseudonocardiaceae," BMC Genomics 15:885 (2014).

UniProt, Sequence of Heme A synthase (ctaA) gene from Bacilus velezensis, UniProtKB—A7Z4B0 (CTAA_BACVZ) (last modified Oct. 23, 2007).

UniProt, Sequence of 8-amino-7-oxononanoate synthase (bioF) gene from Cellvibrio japonicus, UniProtKB—B3PI88 (BIOF_CELJU) (last modified Jul. 28, 2009).

UniProt, Sequence of 4-hydroxyproline 2-epimerase (proR) gene from Pseudomonas putida, UniProtKB—Q88NF3 (4HYPE_PSEPK) (last modified Jun. 1, 2003).

UniProt, Sequence of Autophagy-related protein 23 (ATG23) gene from Ashbya gossypii, UniProtKB—Q756Z7 (ATG23_ASHGO) (last modified Jul. 5, 2004).

* cited by examiner

FIG. 2A

| Conjugate under testing | (Calibrator 2) Counts 0d | (Calibrator 2) Counts 7d 35°C | % Signal recovery after stress |
|---|---|---|---|
| Sales lot rackpack (reference) | 692282 | 666742 | 96% |
| Fab with heavy chain C-terminal GGGYRYRQGGGP | 1548916 | 544607 | 35% |
| IgG with heavy chain C-terminal GGGSYRYRQGGGS | 363103 | 36116 | 10% |

FIG. 9B

| Conjugate under testing | (Calibrator 2) Counts 0d | (Calibrator 2) Counts 7d 35°C | % Signal recovery after stress |
|---|---|---|---|
| Sales lot rackpack (reference) | 692282 | 666742 | 96% |
| IgG with heavy chain C-terminal GGGSYRYRQGGGS | 363103 | 36116 | 10% |
| IgG with heavy chain C-terminal GGGSRVRQRGGGS | 358854 | 349418 | 97% |

FIG. 16

SEQUENCE LISTING

<160> NUMBER OF SEQ ID NOS: 119

<210> SEQ ID NO 1
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 1

Tyr Arg Tyr Arg Gln
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 2

Arg Tyr Glu Ser Lys
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic peptide sequence

<400> SEQUENCE: 3

Asn His Glu Glu Pro Arg
1               5

<210> SEQ ID NO 4
<211> LENGTH: 6
<212> TYPE: PRT
<213> ORGANISM: Artificial Sequence
<220> FEATURE:
<223> OTHER INFORMATION: synthetic peptide sequence

<400> SEQUENCE: 4

Tyr Arg Tyr Arg Ala Arg
1               5

<210> SEQ ID NO 5
<211> LENGTH: 407
<212> TYPE: PRT
<213> ORGANISM: Streptomyces mobaraensis
<220> FEATURE:
<221> NAME/KEY: MISC_FEATURE
<222> LOCATION: (1)..(407)
<223> OTHER INFORMATION: protein-glutamine gamma-glutamyltransferase

<400> SEQUENCE: 5

Met Arg Ile Arg Arg Arg Ala Leu Val Phe Ala Thr Met Ser Ala Val
1               5                   10                  15

Leu Cys Thr Ala Gly Phe Met Pro Ser Ala Gly Glu Ala Ala Ala Asp
                20                  25                  30

Asn Gly Ala Gly Glu Glu Thr Lys Ser Tyr Ala Glu Thr Tyr Arg Leu
            35                  40                  45

Thr Ala Asp Asp Val Ala Asn Ile Asn Ala Leu Asn Glu Ser Ala Pro
        50                  55                  60

Ala Ala Ser Ser Ala Gly Pro Ser Phe Arg Ala Pro Asp Ser Asp Asp

```
            65                  70                  75                  80
Arg Val Thr Pro Pro Ala Glu Pro Leu Asp Arg Met Pro Asp Pro Tyr
                85                  90                  95
Arg Pro Ser Tyr Gly Arg Ala Glu Thr Val Val Asn Asn Tyr Ile Arg
               100                 105                 110
Lys Trp Gln Gln Val Tyr Ser His Arg Asp Gly Arg Lys Gln Gln Met
               115                 120                 125
Thr Glu Glu Gln Arg Glu Trp Leu Ser Tyr Gly Cys Val Gly Val Thr
               130                 135                 140
Trp Val Asn Ser Gly Gln Tyr Pro Thr Asn Arg Leu Ala Phe Ala Ser
145                150                 155                 160
Phe Asp Glu Asp Arg Phe Lys Asn Glu Leu Lys Asn Gly Arg Pro Arg
               165                 170                 175
Ser Gly Glu Thr Arg Ala Glu Phe Glu Gly Arg Val Ala Lys Glu Ser
               180                 185                 190
Phe Asp Glu Glu Lys Gly Phe Gln Arg Ala Arg Glu Val Ala Ser Val
               195                 200                 205
Met Asn Arg Ala Leu Glu Asn Ala His Asp Glu Ser Ala Tyr Leu Asp
210                215                 220
Asn Leu Lys Lys Glu Leu Ala Asn Gly Asn Asp Ala Leu Arg Asn Glu
225                230                 235                 240
Asp Ala Arg Ser Pro Phe Tyr Ser Ala Leu Arg Asn Thr Pro Ser Phe
               245                 250                 255
Lys Glu Arg Asn Gly Gly Asn His Asp Pro Ser Arg Met Lys Ala Val
               260                 265                 270
Ile Tyr Ser Lys His Phe Trp Ser Gly Gln Asp Arg Ser Ser Ser Ala
               275                 280                 285
Asp Lys Arg Lys Tyr Gly Asp Pro Asp Ala Phe Arg Pro Ala Pro Gly
               290                 295                 300
Thr Gly Leu Val Asp Met Ser Arg Asp Arg Asn Ile Pro Arg Ser Pro
305                310                 315                 320
Thr Ser Pro Gly Glu Gly Phe Val Asn Phe Asp Tyr Gly Trp Phe Gly
               325                 330                 335
Ala Gln Thr Glu Ala Asp Ala Asp Lys Thr Val Trp Thr His Gly Asn
               340                 345                 350
His Tyr His Ala Pro Asn Gly Ser Leu Gly Ala Met His Val Tyr Glu
               355                 360                 365
Ser Lys Phe Arg Asn Trp Ser Glu Gly Tyr Ser Asp Phe Asp Arg Gly
               370                 375                 380
Ala Tyr Val Ile Thr Phe Ile Pro Lys Ser Trp Asn Thr Ala Pro Asp
385                390                 395                 400
Lys Val Lys Gln Gly Trp Pro
               405
```

<210> SEQ ID NO 6
<211> LENGTH: 262
<212> TYPE: PRT
<213> ORGANISM: Kutzneria albida
<220> FEATURE:
<221> NAME/KEY: MISC_FEATURE
<222> LOCATION: (1)..(262)
<223> OTHER INFORMATION: Hypothetical_transglutaminase

<400> SEQUENCE: 6

```
Met His Lys Trp Phe Leu Arg Ala Ala Val Val Ala Ala Val Gly Phe
1               5                   10                  15
```

```
Gly Leu Pro Thr Leu Ile Ala Thr Thr Ala Gln Ala Ala Ala Val Ala
            20                  25                  30

Ala Pro Thr Pro Arg Ala Pro Leu Ala Pro Pro Leu Ala Glu Asp Arg
        35                  40                  45

Ser Tyr Arg Thr Trp Arg Val Glu Asp Tyr Val Glu Ala Trp Glu Arg
 50                  55                  60

Tyr His Gly Arg Glu Met Thr Glu Asp Glu Arg Asn Leu Ala Arg
 65                  70                  75                  80

Gly Cys Ile Gly Val Thr Val Asn Leu Asn Arg Glu Asp Leu Ser
                 85                  90                  95

Asn Pro Pro Leu Asn Leu Ser Phe Gly Ser Leu Arg Thr Ala Glu Ala
            100                 105                 110

Val Gln Ala Ala Leu Asn Lys Ile Val Asp Thr His Pro Ser Pro Ala
        115                 120                 125

Gln Tyr Glu Ala Ala Val Ala Lys Asp Pro Ile Leu Lys Arg Leu Lys
130                 135                 140

Asn Val Val Lys Ala Leu Pro Ser Trp Ile Asp Ser Ala Lys Leu Lys
145                 150                 155                 160

Ala Ser Ile Phe Ser Lys Arg Phe Tyr Ser Trp Gln Asn Pro Asp Trp
                165                 170                 175

Ser Glu Glu Arg Ala His Thr Thr Tyr Arg Pro Asp Arg Glu Thr Asp
            180                 185                 190

Gln Val Asp Met Ser Thr Tyr Arg Tyr Arg Ala Arg Pro Gly Tyr Val
        195                 200                 205

Asn Phe Asp Tyr Gly Trp Phe Asp Gln Asp Thr Asn Thr Trp Trp His
210                 215                 220

Ala Asn His Glu Glu Pro Arg Met Val Val Tyr Gln Ser Thr Leu Arg
225                 230                 235                 240

His Tyr Ser Arg Pro Leu Gln Asp Phe Asp Glu Gln Val Phe Thr Val
                245                 250                 255

Ala Phe Ala Lys Lys Asp
                260

<210> SEQ ID NO 7
<211> LENGTH: 165
<212> TYPE: PRT
<213> ORGANISM: Escherichia coli
<220> FEATURE:
<221> NAME/KEY: MISC_FEATURE
<222> LOCATION: (1)..(165)
<223> OTHER INFORMATION: SlyD_fragment

<400> SEQUENCE: 7

Met Lys Val Ala Lys Asp Leu Val Val Ser Leu Ala Tyr Gln Val Arg
 1               5                  10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
 50                  55                  60

Asn Asp Ala Tyr Gly Gln Tyr Asp Glu Asn Leu Val Gln Arg Val Pro
 65                  70                  75                  80

Lys Asp Val Phe Met Gly Val Asp Glu Leu Gln Val Gly Met Arg Phe
                 85                  90                  95
```

```
Leu Ala Glu Thr Asp Gln Gly Pro Val Pro Val Glu Ile Thr Ala Val
                100                 105                 110

Glu Asp Asp His Val Val Val Asp Gly Asn His Met Leu Ala Gly Gln
            115                 120                 125

Asn Leu Lys Phe Asn Val Glu Val Val Ala Ile Arg Glu Ala Thr Glu
        130                 135                 140

Glu Glu Leu Ala His Gly His Val His Gly Ala His Asp His His
145                 150                 155                 160

Asp His Asp His Asp
                165

<210> SEQ ID NO 8
<211> LENGTH: 637
<212> TYPE: PRT
<213> ORGANISM: Artificial Sequence
<220> FEATURE:
<223> OTHER INFORMATION: synthetic peptide sequence - EcSlyD2-Xa-
      KalbTGt3-8xHis-tag
<220> FEATURE:
<221> NAME/KEY: MISC_FEATURE
<222> LOCATION: (1)..(165)
<223> OTHER INFORMATION: SlyD
<220> FEATURE:
<221> NAME/KEY: MISC_FEATURE
<222> LOCATION: (189)..(353)
<223> OTHER INFORMATION: SlyD
<220> FEATURE:
<221> NAME/KEY: MISC_FEATURE
<222> LOCATION: (377)..(380)
<223> OTHER INFORMATION: factor_Xa_cleavage_site
<220> FEATURE:
<221> NAME/KEY: MISC_FEATURE
<222> LOCATION: (386)..(624)
<223> OTHER INFORMATION: K-albida_MTG
<220> FEATURE:
<221> NAME/KEY: MISC_FEATURE
<222> LOCATION: (630)..(637)
<223> OTHER INFORMATION: 8xHis-tag

<400> SEQUENCE: 8

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
            85                  90                  95

Leu Ala Glu Thr Asp Gln Gly Pro Val Pro Val Glu Ile Thr Ala Val
                100                 105                 110

Glu Asp Asp His Val Val Val Asp Gly Asn His Met Leu Ala Gly Gln
            115                 120                 125

Asn Leu Lys Phe Asn Val Glu Val Val Ala Ile Arg Glu Ala Thr Glu
        130                 135                 140

Glu Glu Leu Ala His Gly His Val His Gly Ala His Asp His His
145                 150                 155                 160

Asp His Asp His Asp Gly Gly Gly Ser Gly Gly Gly Ser Gly Gly Gly
                165                 170                 175
```

```
Ser Gly Gly Gly Ser Gly Gly Ser Gly Gly Gly Met Lys Val Ala
            180                 185                 190

Lys Asp Leu Val Val Ser Leu Ala Tyr Gln Val Arg Thr Glu Asp Gly
        195                 200                 205

Val Leu Val Asp Glu Ser Pro Val Ser Ala Pro Leu Asp Tyr Leu His
    210                 215                 220

Gly His Gly Ser Leu Ile Ser Gly Leu Glu Thr Ala Leu Glu Gly His
225                 230                 235                 240

Glu Val Gly Asp Lys Phe Asp Val Ala Val Gly Ala Asn Asp Ala Tyr
                245                 250                 255

Gly Gln Tyr Asp Glu Asn Leu Val Gln Arg Val Pro Lys Asp Val Phe
            260                 265                 270

Met Gly Val Asp Glu Leu Gln Val Gly Met Arg Phe Leu Ala Glu Thr
        275                 280                 285

Asp Gln Gly Pro Val Pro Val Glu Ile Thr Ala Val Glu Asp Asp His
    290                 295                 300

Val Val Val Asp Gly Asn His Met Leu Ala Gly Gln Asn Leu Lys Phe
305                 310                 315                 320

Asn Val Glu Val Val Ala Ile Arg Glu Ala Thr Glu Glu Glu Leu Ala
                325                 330                 335

His Gly His Val His Gly Ala His Asp His His His Asp His Asp His
            340                 345                 350

Asp Gly Gly Gly Ser Gly Gly Ser Gly Gly Gly Ser Gly Gly Gly
        355                 360                 365

Ser Gly Gly Gly Ser Gly Gly Gly Ile Glu Gly Arg Met Gly Gly Gly
    370                 375                 380

Ser Thr Thr Ala Gln Ala Ala Val Ala Ala Pro Thr Pro Arg Ala
385                 390                 395                 400

Pro Leu Ala Pro Pro Leu Ala Glu Asp Arg Ser Tyr Arg Thr Trp Arg
                405                 410                 415

Val Glu Asp Tyr Val Glu Ala Trp Glu Arg Tyr His Gly Arg Glu Met
            420                 425                 430

Thr Glu Asp Glu Arg Glu Asn Leu Ala Arg Gly Cys Ile Gly Val Thr
        435                 440                 445

Val Val Asn Leu Asn Arg Glu Asp Leu Ser Asn Pro Pro Leu Asn Leu
    450                 455                 460

Ser Phe Gly Ser Leu Arg Thr Ala Glu Ala Val Gln Ala Ala Leu Asn
465                 470                 475                 480

Lys Ile Val Asp Thr His Pro Ser Pro Ala Gln Tyr Glu Ala Ala Val
                485                 490                 495

Ala Lys Asp Pro Ile Leu Lys Arg Leu Lys Asn Val Val Lys Ala Leu
            500                 505                 510

Pro Ser Trp Ile Asp Ser Ala Lys Leu Lys Ala Ser Ile Phe Ser Lys
        515                 520                 525

Arg Phe Tyr Ser Trp Gln Asn Pro Asp Trp Ser Glu Glu Arg Ala His
    530                 535                 540

Thr Thr Tyr Arg Pro Asp Arg Glu Thr Asp Gln Val Asp Met Ser Thr
545                 550                 555                 560

Tyr Arg Tyr Arg Ala Arg Pro Gly Tyr Val Asn Phe Tyr Gly Trp
                565                 570                 575

Phe Asp Gln Asp Thr Asn Thr Trp Trp His Ala Asn His Glu Glu Pro
            580                 585                 590

Arg Met Val Val Tyr Gln Ser Thr Leu Arg His Tyr Ser Arg Pro Leu
```

```
                    595                 600                 605
Gln Asp Phe Asp Glu Gln Val Phe Thr Val Ala Phe Ala Lys Lys Asp
            610                 615                 620
Gly Gly Gly Ser Gly His His His His His His
625                 630                 635
```

<210> SEQ ID NO 9
<211> LENGTH: 257
<212> TYPE: PRT
<213> ORGANISM: Artificial Sequence
<220> FEATURE:
<223> OTHER INFORMATION: synthetic peptide sequence - KalbTGt3-8xHis-tag
<220> FEATURE:
<221> NAME/KEY: MISC_FEATURE
<222> LOCATION: (6)..(244)
<223> OTHER INFORMATION: K-albida_MTG
<220> FEATURE:
<221> NAME/KEY: MISC_FEATURE
<222> LOCATION: (250)..(257)
<223> OTHER INFORMATION: 8xHis-tag

<400> SEQUENCE: 9

```
Met Gly Gly Gly Ser Thr Thr Ala Gln Ala Ala Val Ala Ala Pro
1               5                   10                  15

Thr Pro Arg Ala Pro Leu Ala Pro Leu Ala Glu Asp Arg Ser Tyr
                20                  25                  30

Arg Thr Trp Arg Val Glu Asp Tyr Val Glu Ala Trp Glu Arg Tyr His
            35                  40                  45

Gly Arg Glu Met Thr Glu Asp Glu Arg Glu Asn Leu Ala Arg Gly Cys
        50                  55                  60

Ile Gly Val Thr Val Val Asn Leu Asn Arg Glu Asp Leu Ser Asn Pro
65                  70                  75                  80

Pro Leu Asn Leu Ser Phe Gly Ser Leu Arg Thr Ala Glu Ala Val Gln
                85                  90                  95

Ala Ala Leu Asn Lys Ile Val Asp Thr His Pro Ser Pro Ala Gln Tyr
            100                 105                 110

Glu Ala Ala Val Ala Lys Asp Pro Ile Leu Lys Arg Leu Lys Asn Val
        115                 120                 125

Val Lys Ala Leu Pro Ser Trp Ile Asp Ser Ala Lys Leu Lys Ala Ser
130                 135                 140

Ile Phe Ser Lys Arg Phe Tyr Ser Trp Gln Asn Pro Asp Trp Ser Glu
145                 150                 155                 160

Glu Arg Ala His Thr Thr Tyr Arg Pro Asp Arg Glu Thr Asp Gln Val
                165                 170                 175

Asp Met Ser Thr Tyr Arg Tyr Arg Ala Arg Pro Gly Tyr Val Asn Phe
            180                 185                 190

Asp Tyr Gly Trp Phe Asp Gln Asp Thr Asn Thr Trp Trp His Ala Asn
        195                 200                 205

His Glu Glu Pro Arg Met Val Val Tyr Gln Ser Thr Leu Arg His Tyr
    210                 215                 220

Ser Arg Pro Leu Gln Asp Phe Asp Glu Gln Val Phe Thr Val Ala Phe
225                 230                 235                 240

Ala Lys Lys Asp Gly Gly Gly Ser Gly His His His His His His
                245                 250                 255

His
```

<210> SEQ ID NO 10
<211> LENGTH: 238

```
<212> TYPE: PRT
<213> ORGANISM: Artificial Sequence
<220> FEATURE:
<223> OTHER INFORMATION: synthetic peptide sequence - KalbTGt3-8xHis-tag
      (post-trypsin digest)
<220> FEATURE:
<221> NAME/KEY: MISC_FEATURE
<222> LOCATION: (1)..(225)
<223> OTHER INFORMATION: K-albida_MTG
<220> FEATURE:
<221> NAME/KEY: MISC_FEATURE
<222> LOCATION: (231)..(238)
<223> OTHER INFORMATION: 8xHis-tag

<400> SEQUENCE: 10

Ala Pro Leu Ala Pro Pro Leu Ala Glu Asp Arg Ser Tyr Arg Thr Trp
1               5                   10                  15

Arg Val Glu Asp Tyr Val Glu Ala Trp Glu Arg Tyr His Gly Arg Glu
                20                  25                  30

Met Thr Glu Asp Glu Arg Glu Asn Leu Ala Arg Gly Cys Ile Gly Val
            35                  40                  45

Thr Val Val Asn Leu Asn Arg Glu Asp Leu Ser Asn Pro Pro Leu Asn
        50                  55                  60

Leu Ser Phe Gly Ser Leu Arg Thr Ala Glu Ala Val Gln Ala Ala Leu
65                  70                  75                  80

Asn Lys Ile Val Asp Thr His Pro Ser Pro Ala Gln Tyr Glu Ala Ala
                85                  90                  95

Val Ala Lys Asp Pro Ile Leu Lys Arg Leu Lys Asn Val Val Lys Ala
                100                 105                 110

Leu Pro Ser Trp Ile Asp Ser Ala Lys Leu Lys Ala Ser Ile Phe Ser
            115                 120                 125

Lys Arg Phe Tyr Ser Trp Gln Asn Pro Asp Trp Ser Glu Glu Arg Ala
                130                 135                 140

His Thr Thr Tyr Arg Pro Asp Arg Glu Thr Asp Gln Val Asp Met Ser
145                 150                 155                 160

Thr Tyr Arg Tyr Arg Ala Arg Pro Gly Tyr Val Asn Phe Asp Tyr Gly
                165                 170                 175

Trp Phe Asp Gln Asp Thr Asn Thr Trp Trp His Ala Asn His Glu Glu
            180                 185                 190

Pro Arg Met Val Val Tyr Gln Ser Thr Leu Arg His Tyr Ser Arg Pro
                195                 200                 205

Leu Gln Asp Phe Asp Glu Gln Val Phe Thr Val Ala Phe Ala Lys Lys
            210                 215                 220

Asp Gly Gly Gly Ser Gly His His His His His His His
225                 230                 235

<210> SEQ ID NO 11
<211> LENGTH: 613
<212> TYPE: PRT
<213> ORGANISM: Artificial Sequence
<220> FEATURE:
<223> OTHER INFORMATION: synthetic peptide sequence - EcSlyD2-Xa-
      KalbTGt1-8xHis
<220> FEATURE:
<221> NAME/KEY: MISC_FEATURE
<222> LOCATION: (1)..(165)
<223> OTHER INFORMATION: SlyD
<220> FEATURE:
<221> NAME/KEY: MISC_FEATURE
<222> LOCATION: (189)..(353)
<223> OTHER INFORMATION: SlyD
<220> FEATURE:
<221> NAME/KEY: MISC_FEATURE
```

-continued

```
<222> LOCATION: (377)..(380)
<223> OTHER INFORMATION: Factor_Xa_cleavage_site
<220> FEATURE:
<221> NAME/KEY: MISC_FEATURE
<222> LOCATION: (382)..(604)
<223> OTHER INFORMATION: K-albida_MTG
<220> FEATURE:
<221> NAME/KEY: MISC_FEATURE
<222> LOCATION: (606)..(613)
<223> OTHER INFORMATION: 8xHis-tag

<400> SEQUENCE: 11

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
        115                 120                 125

Asn Leu Lys Phe Asn Val Glu Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Met Lys Val Ala
            180                 185                 190

Lys Asp Leu Val Val Ser Leu Ala Tyr Gln Val Arg Thr Glu Asp Gly
        195                 200                 205

Val Leu Val Asp Glu Ser Pro Val Ser Ala Pro Leu Asp Tyr Leu His
    210                 215                 220

Gly His Gly Ser Leu Ile Ser Gly Leu Glu Thr Ala Leu Glu Gly His
225                 230                 235                 240

Glu Val Gly Asp Lys Phe Asp Val Ala Val Gly Ala Asn Asp Ala Tyr
                245                 250                 255

Gly Gln Tyr Asp Glu Asn Leu Val Gln Arg Val Pro Lys Asp Val Phe
            260                 265                 270

Met Gly Val Asp Glu Leu Gln Val Gly Met Arg Phe Leu Ala Glu Thr
        275                 280                 285

Asp Gln Gly Pro Val Pro Val Glu Ile Thr Ala Val Glu Asp Asp His
    290                 295                 300

Val Val Asp Gly Asn His Met Leu Ala Gly Gln Asn Leu Lys Phe
305                 310                 315                 320

Asn Val Glu Val Val Ala Ile Arg Glu Ala Thr Glu Glu Glu Leu Ala
                325                 330                 335

His Gly His Val His Gly Ala His Asp His His Asp His Asp His
            340                 345                 350
```

```
Asp Gly Gly Gly Ser Gly Gly Ser Gly Gly Ser Gly Gly
            355                 360                 365

Ser Gly Gly Gly Ser Gly Gly Gly Ile Glu Gly Arg Met Leu Ala Pro
    370                 375                 380

Pro Leu Ala Glu Asp Arg Ser Tyr Arg Thr Trp Arg Val Glu Asp Tyr
385                 390                 395                 400

Val Glu Ala Trp Glu Arg Tyr His Gly Arg Glu Met Thr Glu Asp Glu
                405                 410                 415

Arg Glu Asn Leu Ala Arg Gly Cys Ile Gly Val Thr Val Asn Leu
            420                 425                 430

Asn Arg Glu Asp Leu Ser Asn Pro Pro Leu Asn Leu Ser Phe Gly Ser
        435                 440                 445

Leu Arg Thr Ala Glu Ala Val Gln Ala Leu Asn Lys Ile Val Asp
    450                 455                 460

Thr His Pro Ser Pro Ala Gln Tyr Glu Ala Ala Val Ala Lys Asp Pro
465                 470                 475                 480

Ile Leu Lys Arg Leu Lys Asn Val Val Lys Ala Leu Pro Ser Trp Ile
                485                 490                 495

Asp Ser Ala Lys Leu Lys Ala Ser Ile Phe Ser Lys Arg Phe Tyr Ser
            500                 505                 510

Trp Gln Asn Pro Asp Trp Ser Glu Glu Arg Ala His Thr Thr Tyr Arg
        515                 520                 525

Pro Asp Arg Glu Thr Asp Gln Val Asp Met Ser Thr Tyr Arg Tyr Arg
    530                 535                 540

Ala Arg Pro Gly Tyr Val Asn Phe Asp Tyr Gly Trp Phe Asp Gln Asp
545                 550                 555                 560

Thr Asn Thr Trp Trp His Ala Asn His Glu Glu Pro Arg Met Val Val
                565                 570                 575

Tyr Gln Ser Thr Leu Arg His Tyr Ser Arg Pro Leu Gln Asp Phe Asp
            580                 585                 590

Glu Gln Val Phe Thr Val Ala Phe Ala Lys Lys Asp Gly His His
        595                 600                 605

His His His His His
    610

<210> SEQ ID NO 12
<211> LENGTH: 233
<212> TYPE: PRT
<213> ORGANISM: Artificial Sequence
<220> FEATURE:
<223> OTHER INFORMATION: synthetic peptide sequence - KalbTGt1-8xHis
<220> FEATURE:
<221> NAME/KEY: MISC_FEATURE
<222> LOCATION: (2)..(224)
<223> OTHER INFORMATION: K-albida_MTG
<220> FEATURE:
<221> NAME/KEY: MISC_FEATURE
<222> LOCATION: (226)..(233)
<223> OTHER INFORMATION: 8xHis-tag

<400> SEQUENCE: 12

Met Leu Ala Pro Pro Leu Ala Glu Asp Arg Ser Tyr Arg Thr Trp Arg
1               5                   10                  15

Val Glu Asp Tyr Val Glu Ala Trp Glu Arg Tyr His Gly Arg Glu Met
                20                  25                  30

Thr Glu Asp Glu Arg Glu Asn Leu Ala Arg Gly Cys Ile Gly Val Thr
            35                  40                  45

Val Val Asn Leu Asn Arg Glu Asp Leu Ser Asn Pro Pro Leu Asn Leu
```

```
                50                  55                  60
Ser Phe Gly Ser Leu Arg Thr Ala Glu Ala Val Gln Ala Ala Leu Asn
 65                  70                  75                  80

Lys Ile Val Asp Thr His Pro Ser Pro Ala Gln Tyr Glu Ala Ala Val
                 85                  90                  95

Ala Lys Asp Pro Ile Leu Lys Arg Leu Lys Asn Val Val Lys Ala Leu
            100                 105                 110

Pro Ser Trp Ile Asp Ser Ala Lys Leu Lys Ala Ser Ile Phe Ser Lys
        115                 120                 125

Arg Phe Tyr Ser Trp Gln Asn Pro Asp Trp Ser Glu Glu Arg Ala His
    130                 135                 140

Thr Thr Tyr Arg Pro Asp Arg Glu Thr Asp Gln Val Asp Met Ser Thr
145                 150                 155                 160

Tyr Arg Tyr Arg Ala Arg Pro Gly Tyr Val Asn Phe Asp Tyr Gly Trp
                165                 170                 175

Phe Asp Gln Asp Thr Asn Thr Trp Trp His Ala Asn His Glu Glu Pro
            180                 185                 190

Arg Met Val Val Tyr Gln Ser Thr Leu Arg His Tyr Ser Arg Pro Leu
        195                 200                 205

Gln Asp Phe Asp Glu Gln Val Phe Thr Val Ala Phe Ala Lys Lys Asp
    210                 215                 220

Gly His His His His His His His
225                 230
```

<210> SEQ ID NO 13
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 13

```
Met Leu Ala Gln Gly
 1               5
```

<210> SEQ ID NO 14
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 14

```
Arg Tyr Arg Gln Arg
 1               5
```

<210> SEQ ID NO 15
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 15

```
Arg Tyr Ser Gln Arg
 1               5
```

<210> SEQ ID NO 16
<211> LENGTH: 5
<212> TYPE: PRT
<213> ORGANISM: Artificial Sequence

```
<220> FEATURE:
<223> OTHER INFORMATION: synthetic peptide sequence

<400> SEQUENCE: 16

Phe Arg Gln Arg Gln
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 17

Arg Gln Arg Gln Arg
1               5

<210> SEQ ID NO 18
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 18

Phe Arg Gln Arg Gly
1               5

<210> SEQ ID NO 19
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 19

Gln Arg Gln Arg Gln
1               5

<210> SEQ ID NO 20
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 20

Tyr Lys Tyr Arg Gln
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 21

Gln Tyr Arg Gln Arg
1               5

<210> SEQ ID NO 22
<211> LENGTH: 5
<212> TYPE: PRT
<213> ORGANISM: Artificial Sequence
<220> FEATURE:
```

<223> OTHER INFORMATION: synthetic peptide sequence

<400> SEQUENCE: 22

Asp Tyr Ala Leu Gln
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic peptide sequence

<400> SEQUENCE: 23

Met Leu Ala Gln Gly Ser
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic peptide sequence

<400> SEQUENCE: 24

Ala Pro Arg Tyr Arg Gln Arg Ala Ala
1               5

<210> SEQ ID NO 25
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 25

Arg Tyr Ser Lys Tyr
1               5

<210> SEQ ID NO 26
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 26

Ala Tyr Arg Thr Lys
1               5

<210> SEQ ID NO 27
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 27

Arg Tyr Arg Ser Lys
1               5

<210> SEQ ID NO 28
<211> LENGTH: 5
<212> TYPE: PRT
<213> ORGANISM: Artificial Sequence
<220> FEATURE:
<223> OTHER INFORMATION: synthetic peptide sequence

```
<400> SEQUENCE: 28

Arg Tyr Gly Lys Ser
1               5

<210> SEQ ID NO 29
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 29

Tyr Lys Gly Arg Gly
1               5

<210> SEQ ID NO 30
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 30

Ala Arg Ser Lys Leu
1               5

<210> SEQ ID NO 31
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 31

Ala Pro Arg Tyr Arg Gln Arg Ala Ala Gly Gly Gly
1               5                   10

<210> SEQ ID NO 32
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 32

Tyr Arg Gln Ser Arg
1               5

<210> SEQ ID NO 33
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 33

Leu Arg Tyr Arg Gln
1               5

<210> SEQ ID NO 34
<211> LENGTH: 5
<212> TYPE: PRT
<213> ORGANISM: Artificial Sequence
<220> FEATURE:
<223> OTHER INFORMATION: synthetic peptide sequence
```

<400> SEQUENCE: 34

Tyr Arg Gln Arg Ala
1               5

<210> SEQ ID NO 35
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 35

Val Arg Tyr Arg Gln
1               5

<210> SEQ ID NO 36
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 36

Gln Arg Gln Thr Arg
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 37

Tyr Arg Gln Thr Arg
1               5

<210> SEQ ID NO 38
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 38

Pro Arg Tyr Arg Gln
1               5

<210> SEQ ID NO 39
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 39

Arg Phe Ser Gln Arg
1               5

<210> SEQ ID NO 40
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 40

```
Trp Gln Arg Gln Arg
1               5

<210> SEQ ID NO 41
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 41

Val Arg Gln Arg Gln
1               5

<210> SEQ ID NO 42
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 42

Arg Tyr Thr Gln Arg
1               5

<210> SEQ ID NO 43
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 43

Ala Tyr Arg Gln Arg
1               5

<210> SEQ ID NO 44
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 44

Tyr Gln Arg Gln Arg
1               5

<210> SEQ ID NO 45
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 45

Asn Tyr Arg Phe Lys
1               5

<210> SEQ ID NO 46
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 46
```

Tyr Gln Lys Trp Lys
1               5

<210> SEQ ID NO 47
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 47

Tyr Lys Tyr Lys Tyr
1               5

<210> SEQ ID NO 48
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 48

Arg Trp Lys Phe Lys
1               5

<210> SEQ ID NO 49
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 49

Arg Phe Tyr Ser Lys
1               5

<210> SEQ ID NO 50
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 50

Tyr Lys Tyr Ala Lys
1               5

<210> SEQ ID NO 51
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 51

Tyr Arg Tyr Ala Lys
1               5

<210> SEQ ID NO 52
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 52

Arg Tyr Ser Tyr Lys 1               5

<210> SEQ ID NO 53
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 53

Tyr Lys Ser Phe Lys
1               5

<210> SEQ ID NO 54
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 54

Tyr Lys Ser Trp Lys
1               5

<210> SEQ ID NO 55
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 55

Lys Tyr Arg Tyr Lys
1               5

<210> SEQ ID NO 56
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 56

Tyr Lys Tyr Asn Lys
1               5

<210> SEQ ID NO 57
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 57

Pro Tyr Lys Tyr Lys
1               5

<210> SEQ ID NO 58
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 58

Phe Tyr Lys Tyr Lys
1               5

```
<210> SEQ ID NO 59
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 59

Phe Tyr Glu Ser Lys
1               5

<210> SEQ ID NO 60
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 60

Glu Trp Val Ala Gln
1               5

<210> SEQ ID NO 61
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 61

Glu Trp Ala Leu Gln
1               5

<210> SEQ ID NO 62
<211> LENGTH: 5
<212> TYPE: PRT
<213> ORGANISM: Artificial Sequence
<220> FEATURE:
<223> OTHER INFORMATION: Artificial Peptide Sequence

<400> SEQUENCE: 62

Asp Tyr Phe Leu Gln
1               5

<210> SEQ ID NO 63
<211> LENGTH: 5
<212> TYPE: PRT
<213> ORGANISM: Artificial Sequence
<220> FEATURE:
<223> OTHER INFORMATION: Artificial Peptide Sequence

<400> SEQUENCE: 63

Glu Tyr Trp Leu Gln
1               5

<210> SEQ ID NO 64
<211> LENGTH: 5
<212> TYPE: PRT
<213> ORGANISM: Artificial Sequence
<220> FEATURE:
<223> OTHER INFORMATION: Artificial Peptide Sequence

<400> SEQUENCE: 64

Asp Trp Ala Leu Gln
1               5
```

```
<210> SEQ ID NO 65
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 65

Asp Trp Tyr Leu Gln
1               5

<210> SEQ ID NO 66
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 66

Asp Tyr Trp Leu Gln
1               5

<210> SEQ ID NO 67
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 67

Glu Tyr Val Ala Gln
1               5

<210> SEQ ID NO 68
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 68

Asp Tyr Val Ala Gln
1               5

<210> SEQ ID NO 69
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 69

Asp Trp Val Ala Gln
1               5

<210> SEQ ID NO 70
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 70

Glu Tyr Val Leu Gln
1               5
```

```
<210> SEQ ID NO 71
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 71

Glu Trp Ile Ala Gln
1               5

<210> SEQ ID NO 72
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 72

Trp Tyr Ala Leu Gln
1               5

<210> SEQ ID NO 73
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 73

Glu Tyr Ala Leu Gln
1               5

<210> SEQ ID NO 74
<211> LENGTH: 5
<212> TYPE: PRT
<213> ORGANISM: Artificial Sequence
<220> FEATURE:
<223> OTHER INFORMATION: synthetic peptide sequence

<400> SEQUENCE: 74

Glu Tyr Phe Leu Gln
1               5

<210> SEQ ID NO 75
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 75

Gly Gly Gly Tyr Arg Tyr Arg Gln Gly Gly Gly Gly
1               5                   10

<210> SEQ ID NO 76
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 76

Gly Gly Gly Asp Tyr Ala Leu Gln Gly Gly Gly Gly
1               5                   10

<210> SEQ ID NO 77
```

```
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 77

Gly Gly Gly Gln Arg Trp Arg Gln Gly Gly Gly Gly
1               5                   10

<210> SEQ ID NO 78
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 78

Gly Gly Gly Trp Arg Tyr Arg Gln Gly Gly Gly Gly
1               5                   10

<210> SEQ ID NO 79
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 79

Gly Gly Gly Arg Tyr Arg Gln Arg Gly Gly Gly Gly
1               5                   10

<210> SEQ ID NO 80
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 80

Gly Gly Gly Arg Tyr Ser Gln Arg Gly Gly Gly Gly
1               5                   10

<210> SEQ ID NO 81
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 81

Gly Gly Gly Phe Arg Gln Arg Gln Gly Gly Gly Gly
1               5                   10

<210> SEQ ID NO 82
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 82

Gly Gly Gly Arg Gln Arg Gln Arg Gly Gly Gly Gly
1               5                   10

<210> SEQ ID NO 83
<211> LENGTH: 12
```

```
<212> TYPE: PRT
<213> ORGANISM: Artificial Sequence
<220> FEATURE:
<223> OTHER INFORMATION: synthetic peptide sequence

<400> SEQUENCE: 83

Gly Gly Gly Phe Arg Gln Arg Gly Gly Gly Gly
1               5                   10

<210> SEQ ID NO 84
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 84

Gly Gly Gly Gln Arg Gln Arg Gln Gly Gly Gly Gly
1               5                   10

<210> SEQ ID NO 85
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 85

Gly Gly Gly Tyr Lys Tyr Arg Gln Gly Gly Gly Gly
1               5                   10

<210> SEQ ID NO 86
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 86

Gly Gly Gly Gln Tyr Arg Gln Arg Gly Gly Gly Gly
1               5                   10

<210> SEQ ID NO 87
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 87

Gly Gly Gly Met Leu Ala Gln Gly Ser Gly Gly Gly
1               5                   10

<210> SEQ ID NO 88
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 88

Gly Gly Gly Arg Tyr Ser Lys Tyr Gly Gly Gly Gly
1               5                   10

<210> SEQ ID NO 89
<211> LENGTH: 12
<212> TYPE: PRT
```

```
<213> ORGANISM: Artificial Sequence
<220> FEATURE:
<223> OTHER INFORMATION: synthetic peptide sequence

<400> SEQUENCE: 89

Gly Gly Gly Ala Tyr Arg Thr Lys Gly Gly Gly Gly
1               5                   10

<210> SEQ ID NO 90
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 90

Gly Gly Gly Arg Tyr Arg Ser Lys Gly Gly Gly Gly
1               5                   10

<210> SEQ ID NO 91
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 91

Gly Gly Gly Tyr Lys Gly Arg Gly Gly Gly Gly Gly
1               5                   10

<210> SEQ ID NO 92
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 92

Gly Gly Gly Arg Tyr Gly Lys Ser Gly Gly Gly Gly
1               5                   10

<210> SEQ ID NO 93
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 93

Gly Gly Gly Arg Tyr Glu Ser Lys Gly Gly Gly Gly
1               5                   10

<210> SEQ ID NO 94
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 94

Gly Gly Gly Pro Gly Arg Tyr Lys Gly Gly Gly Gly
1               5                   10

<210> SEQ ID NO 95
<211> LENGTH: 12
<212> TYPE: PRT
<213> ORGANISM: Artificial Sequence
```

-continued

```
<220> FEATURE:
<223> OTHER INFORMATION: synthetic peptide sequence

<400> SEQUENCE: 95

Gly Gly Gly Ala Arg Ser Lys Leu Gly Gly Gly Gly
1               5                   10

<210> SEQ ID NO 96
<211> LENGTH: 149
<212> TYPE: PRT
<213> ORGANISM: Thermus thermophilus
<220> FEATURE:
<221> NAME/KEY: MISC_FEATURE
<222> LOCATION: (1)..(149)
<223> OTHER INFORMATION: SlyD

<400> SEQUENCE: 96

Met Lys Val Gly Gln Asp Lys Val Val Thr Ile Arg Tyr Thr Leu Gln
1               5                   10                  15

Val Glu Gly Glu Val Leu Asp Gln Gly Glu Leu Ser Tyr Leu His Gly
            20                  25                  30

His Arg Asn Leu Ile Pro Gly Leu Glu Glu Ala Leu Glu Gly Arg Glu
        35                  40                  45

Glu Gly Glu Ala Phe Gln Ala His Val Pro Ala Glu Lys Ala Tyr Gly
    50                  55                  60

Pro His Asp Pro Glu Gly Val Gln Val Val Pro Leu Ser Ala Phe Pro
65                  70                  75                  80

Glu Asp Ala Glu Val Val Pro Gly Ala Gln Phe Tyr Ala Gln Asp Met
                85                  90                  95

Glu Gly Asn Pro Met Pro Leu Thr Val Val Ala Val Glu Gly Glu Glu
            100                 105                 110

Val Thr Val Asp Phe Asn His Pro Leu Ala Gly Lys Asp Leu Asp Phe
        115                 120                 125

Gln Val Glu Val Val Lys Val Arg Glu Ala Thr Pro Glu Glu Leu Leu
    130                 135                 140

His Gly His Ala His
145

<210> SEQ ID NO 97
<211> LENGTH: 117
<212> TYPE: PRT
<213> ORGANISM: Artificial Sequence
<220> FEATURE:
<223> OTHER INFORMATION: synthetic peptide sequence - KalbTG acyl-donor
      sequence grafted onto the FKBP domain of SlyD
<220> FEATURE:
<221> NAME/KEY: MISC_FEATURE
<222> LOCATION: (1)..(64)
<223> OTHER INFORMATION: FKBP_domain
<220> FEATURE:
<221> NAME/KEY: MISC_FEATURE
<222> LOCATION: (72)..(76)
<223> OTHER INFORMATION: acyl-donor_tag
<220> FEATURE:
<221> NAME/KEY: MISC_FEATURE
<222> LOCATION: (110)..(117)
<223> OTHER INFORMATION: 8xHis_tag

<400> SEQUENCE: 97

Met Lys Val Gly Gln Asp Lys Val Val Thr Ile Arg Tyr Thr Leu Gln
1               5                   10                  15

Val Glu Gly Glu Val Leu Asp Gln Gly Glu Leu Ser Tyr Leu His Gly
            20                  25                  30
```

His Arg Asn Leu Ile Pro Gly Leu Glu Glu Ala Leu Glu Gly Arg Glu
                 35                  40                  45

Glu Gly Glu Ala Phe Gln Ala His Val Pro Ala Glu Lys Ala Tyr Gly
 50                  55                  60

Ala Gly Ser Gly Gly Gly Arg Tyr Arg Gln Arg Gly Gly Gly
 65                  70                  75                  80

Gly Ser Ser Gly Lys Asp Leu Asp Phe Gln Val Glu Val Lys Val
                 85                  90                  95

Arg Glu Ala Thr Pro Glu Glu Leu Leu His Gly His Ala His His
             100                 105                 110

His His His His His
         115

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Gly Gly Ser Tyr Arg Tyr Arg Gln Gly Gly Gly Ser
 1               5                  10

<210> SEQ ID NO 105
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 105

Gly Gly Gly Tyr Arg Tyr Arg Gln Gly Gly Gly Pro
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Gly Gly Ser Tyr Arg Tyr Arg Gln Gly Gly Gly Ser
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Gly Gly Ser Pro Arg Tyr Arg Gln Gly Gly Gly Ser
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Gly Ser Arg Trp Arg Gln Arg Gly Gly Gly Ser
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Gly Ser Arg Val Arg Gln Arg Gly Gly Gly Ser
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Gly Gly Ser Pro Lys Phe Arg Gln Gly Gly Gly Ser
1               5                   10
```

```
<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Gly Ser Pro Lys Gln Arg Gln Gly Gly Gly Ser
1               5                   10

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Trp Arg Gln Arg
1               5

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Val Arg Gln Arg
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Pro Lys Phe Arg Gln
1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Pro Lys Gln Arg Gln
1               5

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 116

Gly Gly Gly Ser
1

<210> SEQ ID NO 117
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Gly Gly Tyr
1

<210> SEQ ID NO 118
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Gly Gly Pro
1

<210> SEQ ID NO 119
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Gly Gly
1
```

SYSTEM AND METHOD FOR IDENTIFICATION AND CHARACTERIZATION OF TRANSGLUTAMINASE SPECIES

CROSS-REFERENCE TO RELATED APPLICATIONS

This application is a continuation-in-part of, and incorporates herein by reference, U.S. patent application Ser. No. 15/974,385, filed on May 8, 2018, and entitled "System and Method for Identification and Characterization of Transglutaminase Species," which is based on, claims the benefit of, and incorporates herein by reference, U.S. Provisional Patent Application No. 62/094,495 filed on Dec. 19, 2014, and entitled, "Identification of Transglutaminase Substrates and Uses Therefor," and U.S. Provisional Patent Application No. 62/260,162 filed on Nov. 25, 2015, and entitled, "System and Method for Identification and Characterization of Transglutaminase Species."

STATEMENT REGARDING FEDERALLY SPONSORED RESEARCH

Not applicable.

SEQUENCE LISTING

The instant patent application contains a Sequence Listing, which has been submitted electronically in ASCII format and is hereby incorporated by reference in its entirety. The ASCII copy, created Feb. 7, 2020, is named 33154-US3_SL, and is 48 KB in size.

BACKGROUND OF THE INVENTION

The disclosure relates, in general, to the identification of transglutaminases and substrates therefore, and more particularly to the discovery and characterization of a microbial transglutaminase from *Kutzneria albida*.

Elucidating the details of enzyme activity and specificity is important for understanding the physiological function of enzymes and for biotechnological applications of the reactions catalyzed by enzymes. For example, transglutaminases belong to a large family of related enzymes, including microbial and mammalian transglutaminases. Transglutaminases catalyze cross-linking between two polypeptide or peptide chains by forming an isopeptide bond between a gamma-carboxamide group of a glutamine residue and an epsilon-amino group of a lysine residue. Elucidating the details of transglutaminase activity and specificity is important for biotechnological applications of the cross-linking reaction catalyzed by transglutaminases, for example, for modification of proteins for labeling, tagging, multi-protein complex formation, and the like.

To date, microbial transglutaminase is the most studied transglutaminase enzyme because of its small size, robust performance, stability, and the calcium independence of its activity. Several studies have shown that a broad variety of long alkylamines can substitute for the lysine substrate of transglutaminases and the simple dipeptide glutamine-glycine can serve as the glutamine substrate. These discoveries of lysine and glutamine substrates of transglutaminases have helped to develop a variety of tests for transglutaminase activity and practical assays for modification of proteins using transglutaminases. However, several challenges may still arise in the identification and characterization of known and novel transglutaminases. One challenge is the specificity of a particular transglutaminase for isopeptide bond formation may be too broad or too narrow for a particular application. Another challenge is transglutaminases having the same or similar substrate specificity may not be useful for orthogonal labeling strategies, or the like. Yet another challenge is the identification of substrates for uncharacterized or poorly characterized transglutaminases. Still other challenges may arise depending on factors associated with a given transglutaminase, such as the origin, specificity, activity, stability, the like, and combinations thereof.

SUMMARY OF THE INVENTION

The present invention overcomes the aforementioned drawbacks by providing a system and method for the identification and characterization of transglutaminases, as well as substrates and uses therefor.

In accordance with one aspect of the present disclosure, a substrate tag for a microbial transglutaminase includes one of an acyl-donor tag having at least 80% sequence identity to the peptide sequence YRYRQ (SEQ ID NO:1), and an amine donor tag having at least 80% sequence identity to the peptide sequence RYESK (SEQ ID NO:2).

In one aspect, the microbial transglutaminase has at least 80% sequence identity to the *Kutzneria albida* microbial transglutaminase (SEQ ID NO:6).

In another aspect, the substrate tag further includes a detectable label.

In another aspect, the detectable label is selected from a biotin moiety, a fluorescent dye, a ruthenium label, a radiolabel, and a chemiluminescent label.

In another aspect, the acyl-donor tag having the peptide sequence APRYRQRAA (SEQ ID NO:24).

In accordance with another aspect of the present disclosure, a method of forming an isopeptide bond in the presence of a microbial transglutaminase includes exposing a microbial transglutaminase to a first substrate and a second substrate, the first substrate including an acyl-donor tag having at least 80% sequence identity to the peptide sequence YRYRQ (SEQ ID NO:1), and the second substrate including an amine-donor tag having at least 80% sequence identity to the peptide sequence RYESK (SEQ ID NO:2), and cross-linking the first substrate and the second substrate, thereby forming an isopeptide bond between the acyl donor tag and the amino donor tag.

In one aspect, the microbial transglutaminase has at least 80% sequence identity to the *Kutzneria albida* microbial transglutaminase (SEQ ID NO:6).

In another aspect, the step of cross-linking the first substrate and the second substrate forms an isopeptide bond between a gamma-carboxamide group of the acyl-donor tag and an epsilon-amino group of the amino-donor tag.

In another aspect, at least one of the first substrate and the second substrate includes a detectable label.

In another aspect, the detectable label is selected from a biotin moiety, a fluorescent dye, a ruthenium label, a radiolabel, and a chemiluminescent label.

In another aspect, the acyl-donor tag having the peptide sequence APRYRQRAA (SEQ ID NO:24).

In another aspect, cross-linking of the first substrate to the second substrate is achieved with a yield of at least about 70%.

In another aspect, the yield is achieved within about 30 minutes.

In accordance with another aspect of the present disclosure, a kit for forming an isopeptide bond in the presence of a microbial transglutaminase, includes a purified microbial transglutaminase having at least 80% sequence identity to the *Kutzneria albida* microbial transglutaminase (SEQ ID NO:6).

In one aspect, the kit further includes one of a first substrate including an acyl-donor tag having at least 80% sequence identity to the peptide sequence YRYRQ (SEQ ID NO:1), and a second substrate including an amine-donor tag having at least 80% sequence identity to the peptide sequence RYESK (SEQ ID NO:2).

In another aspect, at least one of the first substrate and the second substrate includes a detectable label.

In another aspect, the detectable label is selected from a biotin moiety, a fluorescent dye, a ruthenium label, a radiolabel, and a chemiluminescent label.

In another aspect, the acyl-donor tag having the peptide sequence APRYRQRAA (SEQ ID NO:24).

In another aspect, the kit further includes the other one of the first substrate and the second substrate.

In accordance with another aspect of the present disclosure, an enzyme for forming an isopeptide bond includes a purified microbial transglutaminase having at least 80% sequence identity to the *Kutzneria albida* microbial transglutaminase (SEQ ID N0:6).

In one aspect, the isolated microbial transglutaminase is expressed and isolated in the presence of ammonium.

In another aspect, the ammonium is present at a concentration of at least about 10 µM.

In accordance with another aspect of the present disclosure, an acyl-donor substrate for a transglutaminase includes an amino acid sequence having the formula $Xaa_1$-$Xaa_2$-$Xaa_3$-$Xaa_4$-$Xaa_5$, where Xaa is any amino acid, where at least one of $Xaa_3$, $Xaa_4$, and $Xaa_5$ is glutamine, where one of $Xaa_4$ and $Xaa_5$ is arginine, where the amino acid sequence includes at least one arginine sequentially adjacent to a glutamine, and where the total number of amino acids in the amino acid sequence selected from arginine, glutamine, phenylalanine, tryptophan, and tyrosine is at least four.

In one aspect, $Xaa_5$ and at least one of $Xaa_1$, $Xaa_2$, and $Xaa_3$ is arginine.

In accordance with another aspect of the present disclosure, an amine-donor substrate for a transglutaminase includes an amino acid sequence having the formula $Xaa_1$-$Xaa_2$-$Xaa_3$-$Xaa_4$-$Xaa_5$, where Xaa is any amino acid, where the amino acid sequence includes at least one lysine, where one of $Xaa_1$ and $Xaa_2$ is selected from tyrosine and arginine, and where the total number of amino acids in the amino acid sequence selected from arginine, serine, tyrosine, and lysine is at least three.

In one aspect, one of $Xaa_4$ and $Xaa_5$ is lysine.

In another aspect, the amino acid sequence includes no more than two of the amino acid lysine.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A is a Clustal Omega version 1.2.1 (Sievers et al., 2011. *Molecular Systems Biology* 7:539) multiple sequence alignment of *Kutzneria albida* KALB_7456 hypothetical protein (SEQ ID NO:6) (upper row) and *Streptomyces mobaraensis* microbial transglutaminase (SEQ ID NO:5) (lower row). Identical amino acid residues are marked by asterisks (*), similar residues by colons (:). Conserved residues of the *S. mobaraensis* microbial transglutaminase catalytic triad (Cys, Asp, His) are highlighted in grey.

FIG. 9B depicts the assay performance data showing only 35% recovery of the Fab with heavy chain C-terminal GGGYRYRQGGGP and only 10% recovery of the IgG with heavy chain C-terminal GGGYRYRQGGGS, which also shows significant clipping/degradation of the Fab- or IgG-conjugated Q-tag substrates over time, as described in Example 7.

FIG. 16 depicts data showing IgG with C-terminal RVRQR (SEQ ID NO:113) show superior stability in tested Elecsys buffer compared to those with YRYRQ (SEQ ID NO:1). IgGs with C-terminal tagging of heavy chain with different Q-tag substrate, either GGGYRYRQGGGP (SEQ ID NO:105) or GGGSRVRQRGGGS (SEQ ID NO:109), were conjugated with biotin using *Kutzneria albida* transglutaminase. The substrate tag GGGYRYRQGGGP (SEQ ID NO:105) comprises the Q-tag YRYRQ (SEQ ID NO:1), with the linkers GGG (SEQ ID NO:119) and GGGP (SEQ ID NO:118) attached to either side. Similarly, the substrate tag GGGSRVRQRGGGS (SEQ ID NO:109) comprises the Q-tag RVRQR (SEQ ID NO:113), with the linker GGGS (SEQ ID NO:116) attached to both of its sides. Conjugates were tested on Elecsys E170 analyzer in the respective assay buffer using calibrator 2 of the respective assay. Conjugates were then stressed for seven days at 35° C. Elecsys measurements were repeated and amount of signal recovery (reflected as a percentage) was calculated compared to an original sales lot rackpack of the same assay.

DETAILED DESCRIPTION

Figure 1:
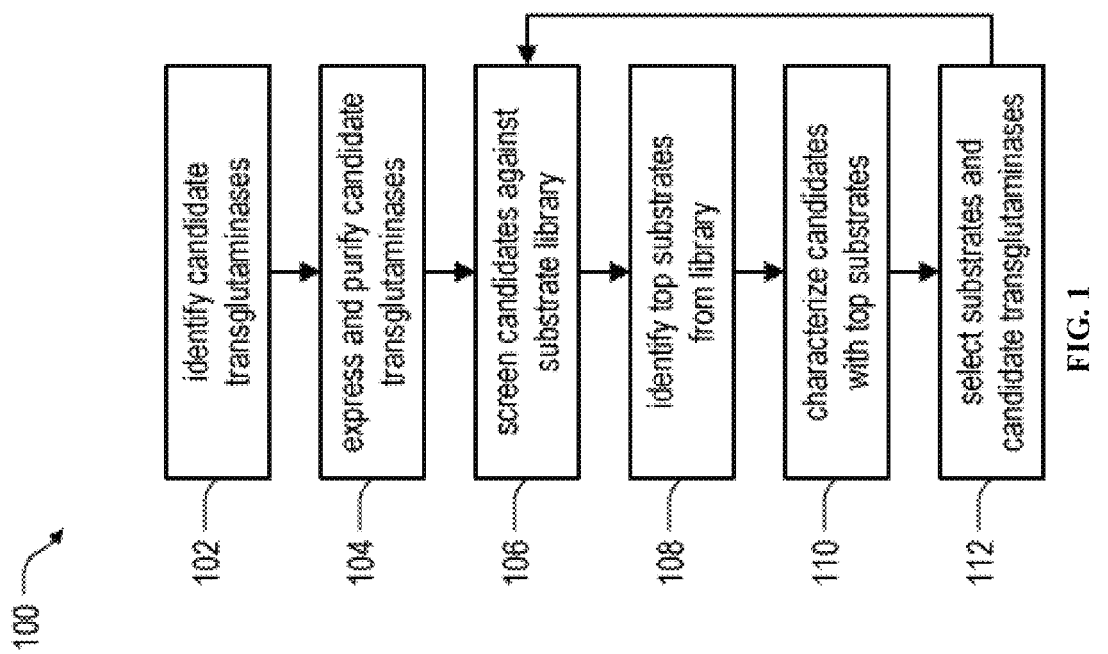
FIG. 1 is a schematic diagram illustrating an embodiment of a method for identification and characterization of transglutaminase species according to the present disclosure.

As discussed above, in various situations it may be useful to elucidate details of enzyme activity and specificity to provide both a basic understanding of those enzymes, as well as for the development of biotechnological applications including those enzymes. For example, conventional chemical strategies for the modification of therapeutic and diagnostic proteins often lack site-specificity, linkage stability, stoichiometric control, or a combination thereof, giving rise to heterogeneous conjugates which may cause interference (e.g., with immunoreactivity or stability of a therapeutic agent). In one aspect, it is anticipated that the industrial development of therapeutic and diagnostic reagents of the coming years will see a massive increase in sophisticated formats requiring stable and truly site-specific conjugation. Therefore, there is a need for new enzymatic methods that offer an attractive and cost-effective alternative to established chemical strategies.

Microbial transglutaminase (MTG) is a protein-glutamine γ-glutamyltransferase (EC 2.3.2.13) that was first described by researchers of Ajinomoto Co., Inc. in 1989, and is one of the most widely used groups of enzymes for the cross-linking of proteins and peptides in many food and biotechnological applications. MTG was first discovered in and later extracted from the organism *Streptomyces mobaraensis*. MTG catalyzes the formation of a stable isopeptide bond between an acyl-group (e.g., a glutamine side chain; acyl-donor) and an alkyl-amine (e.g., a lysine side chain; amine-donor). In the absence of reactive amine groups, the enzymatic reaction with water leads to deamination of glutamine side chains. The bacterial enzyme works without the addition of cofactors such as $Ca^{2+}$ or GTP and in a broad range of pH, buffer, and temperature conditions.

In contrast to sortase A, whose natural substrate specificity is very stringent, the known MTG (e.g., from *S. mobaraensis*) are generally promiscuous enzymes with regard to substrate molecules and the specificities of transglutaminase variants remain largely unknown. While significant scientific efforts have been made to establish MTG as the enzyme of choice in the development of therapeutic antibody-drug conjugates, the large-scale production of such MTG-mediated immunoconjugates is hampered by the low specificity of the enzyme.

Known MTG species are mainly representatives of the families *Streptomyces* or *Bacillus*. These MTG species exhibit very similar primary amino acid structures and substrate specificities. All known active MTG species exhibit molecular weights of at least about 38 kDa. Being a cross-linking enzyme in nature, known MTG generally display broad substrate specificity for amine-donor substrates and a relatively low specificity for acyl-donor substrates. Approaches for the high-throughput screening of improved MTG substrates have previously been limited to phage panning or mRNA display. While recently pioneered array-based high-throughput screening approaches have successfully identified substrates of the *S. mobaraensis* MTG (U.S. Provisional Pat. App. Ser. No. 62/094,495 to Albert et al. filed on 19 Dec. 2014), only the substrate specificities of this and homolog enzymes are known, thereby precluding any bio-orthogonal conjugation approaches (e.g., simultaneous labeling of a biomolecule using two or more different label-substrates and two or more transglutaminase species). Accordingly, there is a need for high-throughput approaches for the identification and characterization of new transglutaminase species. Moreover, there is a need for improved transglutaminases with greater activity, specificity, or a combination thereof. Further, there is a need for acyl-donor tags (e.g., glutamine- or Q-tags) and amine-donor tags (e.g., lysine- or K-tags) that are specific and unique substrates for a transglutaminase of interest.

These and other challenges may be overcome with a system and method for the identification and characterization of transglutaminase species. To this end, the present disclosure provides for characterization of the structure and biochemistry of known and unknown candidate transglutaminase species. The disclosure further provides for characterization of the recombinant production of candidate transglutaminases, high-throughput screening of potential transglutaminase substrates via high-density peptide array, and semi-orthogonal conjugation of biomolecules using the newly characterized transglutaminase species. In yet another aspect, the present disclosure provides for the acyl-donor tags (e.g., glutamine- or Q-tags) and amine-donor tags (e.g., lysine- or K-tags) that are specific and unique substrates for a transglutaminase of interest. Here, the term 'tag' refers to a sequence including one or more amino acids or other like molecules that can be grafted, fused, conjugated, or otherwise attached to another structure, such as a protein, peptide, small molecule, detectable label (e.g., a fluorescent dye), oligonucleotide, non-amino or nucleic acid polymer (e.g., polyethylene glycol), or the like. In one aspect, the nature of the attachment should enable the access to the tag by an enzyme for which the tag is a substrate.

In one embodiment of the present disclosure, a previously unknown transglutaminase species from the organism *Kutzneria albida* was identified, recombinantly expressed, purified, and characterized using a high-throughput array-based screening approach. The *K. albida* transglutaminase was determined to exhibit a high selectivity and substrate specificity for its array-determined substrate sequences, but reacts only poorly or not at all with substrate sequences of the *S. mobaraensis* enzyme. Accordingly, the *K. albida* transglutaminase can be said to be bio-orthogonal to the *S. mobaraensis* enzyme. In another aspect, the *K. albida* transglutaminase exhibited a surprisingly lower molecular weight (about 30 kDa) than all previously described MTG species (e.g., *S. mobaraensis* MTG is about 38 kDa), signifying an advantage for production and enzymatic labeling purposes. Further, the *K. albida* transglutaminase had a distinctly different primary amino acid structure compared to all currently known proteins. Overall, these properties make the *K. albida* transglutaminase highly attractive for a broad range of applications, including, but not limited to, the versatile, cost-effective, and site-specific conjugation of biomolecules with various label molecules. Additional or alternative applications where the *K. albida* transglutaminase can be effective include the production of therapeutic antibody-drug conjugates or chemiluminescent antibodies for in-vitro diagnostic uses.

In one aspect, a number of the challenges posed by recombinant production of transglutaminases may be overcome through implementation of embodiments of the present disclosure. With reference to FIG. 1, a method 100 of identifying and characterizing a transglutaminase includes a step 102 of identifying candidate transglutaminases. The step 102 can include a search for homologs of known or suspected transglutaminase species to identify candidate transglutaminases for further study. In one illustrative embodiment, the transglutaminase can be a microbial transglutaminase (e.g., a *Streptoverticillium* sp. transglutaminase, *Kutzneria* sp. transglutaminase, *Streptomyces* sp., or the like) or a mammalian transglutaminase. In embodiments where the enzyme is a mammalian transglutaminase, the mammalian transglutaminase can be, for example, selected from the group consisting of Human Factor XIII A transglutaminase, Human Factor XIII B transglutaminase, a Factor XIII transglutaminase, a keratinocyte transglutaminase, a tissue-type transglutaminase, an epidermal transglutaminase, a prostate transglutaminase, a neuronal transglutaminase, a human transglutaminase 5, and a human transglutaminase 7.

A search for homologs of known or suspected candidate transglutaminases can include the use of one or more search tools or databases. One suitable tool includes the Protein Basic Local Alignment Search Tool (Protein BLAST) from the National Center for Biotechnology Information (NCBI). The Protein BLAST tool can be supplied with the sequence of known or suspected transglutaminase species, the sequences of which can be obtained from various databases. One example database is the Universal Protein catalog (UniProt). However, other databases may be used in addition, or as an alternative to UniProt. In one aspect, when using Protein BLAST, a threshold Expect-value (E-value) may be selected for narrowing the results of the search. In one example, it may be useful to select an E-value of less than about $10^{-8}$. In another example, it may be useful to select an E-value of less than about $10^{-10}$. In yet another example, it may be useful to select an E-value of less than about $10^{-12}$.

The step 102 can further include performance of a sequence alignment of a transglutaminase sequence with an alignment tool. One example alignment tool includes the Clustal Omega 1.2.1 tool (Sievers et al. 2011, *Molecular Systems Biology* 7: 539). An alignment tool can provide a percent identity matrix value, identify potential conservation of catalytically active residues (if known), or a combination thereof. Other tools that can be used in the step 102 include the ProP 1.0 Server from the Technical University of Denmark (Duckert et al. 2004, *Protein Engineering, Design & Selection* 17(1): 107-112) to predict propeptide and signal sequences of a transglutaminase. In one aspect, a candidate transglutaminase may have a similarity of at least about 20%, at least about 25%, at least about 30%, at least about 35%, or more with respect to a known transglutaminase. Further, a candidate transglutaminase may be characterized by conservation of at least one or more active site residues with respect to a known or suspected transglutaminase, indicating that the enzymatic structure and function may be preserved.

Information gleaned in the step 102 through the use of one or more of the aforementioned tools can be used to select candidate transglutaminases from predicted or known transglutaminase sequences for expression and purification in a step 104. In one aspect, the step 104 can include rapidly screening expression conditions for a candidate transglutaminase species. One suitable method for screening includes insertion of the genetic insert for the candidate transglutaminase into one or more expression vectors designed for soluble cytosolic or periplasmic expression in a host organism using a fragment exchange system (Geertsma, et al. 2011. *Biochemistry* 50(15): 3272-3278). Other methods for screening may also be employed.

The step 104 can further include an initial screening to identify evidence of expression of full-length protein with the anticipated electrophoretic mobility. In the case that poor or no expression of the full-length, active candidate transglutaminase protein is observed, a candidate transglutaminase sequence can be fused with a chaperone (e.g., SlyD) to improve the likelihood of expression of functional enzyme. Expression of a candidate transglutaminase can be further optimized by screening different incubation times, incubation temperatures, inducer concentrations, induction times, media types, media volumes, the like, and combinations thereof.

In general, it will be appreciated that the many viable purification and expression strategies can be employed in the step 104 of the method 100. In one embodiment, a candidate transglutaminase sequence can be incorporated into a modular expression construct. Example expression constructs for use in the step 104 can include chaperone modules, protease cleavage site modules, purification tag modules, detection modules, the like, and combinations thereof. For example, an expression construct may include one or more SlyD chaperone modules arranged to yield a transglutaminase-chaperone fusion protein, one or more protease cleavage sites modules flanking the transglutaminase sequence for separation of the various modules following expression, and one or more 8x-histidine tags or other purification modules for recovery of one or more segments of the expressed protein. For expression constructs including a protease cleavage site module, the expressed protein can be treated with one or more proteases to yield the activated protein. For example, the expressed protein can be treated with a factor Xa protease, trypsin protease, thrombin protease, or another like protease to cleave any chaperone proteins, propeptide sequences, purification tags, or the like from the expressed candidate transglutaminase.

For the production of a selected transglutaminase protein, the gene sequence encoding the candidate transglutaminase—including some, none or all predicted signal and propeptide sequences—can be codon optimized and chemically synthesized for expression in a particular host organism (e.g., *E. coli*). Expression can be performed according to standard molecular biology protocols as described, for example, in Green, et al., 2012, *Molecular Cloning: A Laboratory Manual*, Cold Spring Harbor Laboratory Press.

In a next step 106 of the method 100, candidate transglutaminases expressed and purified in the step 104 are screened against a substrate library to identify potential substrates including acyl-donor sequences, amine-donor sequences, or both. In one aspect, the substrate library can include a plurality of peptide features synthesized in an array by maskless array synthesis (U.S. Pat. Pub. No 2015/0185216 to Albert et al. filed on 19 Dec. 2014). The peptide features can be prepared from natural amino acids, non-natural amino acids, other molecular building blocks, the like, and combinations thereof. Further, the peptides can be in a linear, cyclic or constrained (macrocycle) form.

As used herein, the terms "peptide," "oligopeptide" or "peptide binder" refer to organic compounds composed of amino acids, which may be arranged in either a linear chain (joined together by peptide bonds between the carboxyl and amino groups of adjacent amino acid residues), in a cyclic form or in a constrained (e.g., "macrocycle" form). The terms "peptide" or "oligopeptide" also refer to shorter polypeptides, i.e., organic compounds composed of less than 50 amino acid residues. A macrocycle (or constrained peptide), as used herein, is used in its customary meaning for describing a cyclic small molecule such as a peptide of about 500 Daltons to about 2,000 Daltons.

The term "natural amino acid" refers to one of the 20 amino acids typically found in proteins and used for protein biosynthesis as well as other amino acids which can be incorporated into proteins during translation (including pyrrolysine and selenocysteine). The 20 natural amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine, and lysine.

The term "non-natural amino acid" refers to an organic compound that is not among those encoded by the standard genetic code, or incorporated into proteins during translation. Therefore, non-natural amino acids include amino acids or analogs of amino acids, but are not limited to, the D-isostereomers of amino acids, the beta-amino-analogs of amino acids, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

With continued reference to FIG. 1, a step 108 of the method 100 includes identifying from the substrate library top amine-donor substrate sequences, acyl-donor substrate sequences, or both. In one aspect, activity of the candidate transglutaminases on the library substrates can be measured using one or more direct or coupled assays. In general, a direct assay includes measurement of the reactants (e.g., substrates, co-factors, etc.) and products (e.g., isopeptide bonds, deamidated substrates, etc.) of the enzymatic reaction. For example, spectrophotometry can be used to track the course of the enzymatic reaction by measuring a change in light absorbance associated with a reactant or product over time. In the case that the enzymatic reaction is not conducive to the use of one or more direct assay measurements, or in addition or as an alternative to a direct assay, a coupled assay can be employed. In the case of a coupled assay, the product of the enzymatic reaction of interest can be used as the substrate of another, more readily measured secondary reaction. Examples of coupled assays include measurement of redox reactions involving cofactors such as NADP(H) and NAD(H) that are involved as products or reactants in the enzymatic reaction of interest. In the case of the reaction catalyzed by a transglutaminase, a glutamate dehydrogenase (GLDH) dependent oxidation coupled assay may be implemented. One example of a GLDH assay includes β-casein as a cross-linking substrate and detection of deamidation by GLDH oxidation of NADPH. Notably, it may be useful to select an assay that is compatible with a high-throughput screening format in order to investigate a large number of substrates (e.g., greater than 1 million) in parallel.

Using one of the aforementioned direct or indirect assays, the step 108 can include the use of peptide substrate arrays to identify specific sequences or motifs recognized by the candidate transglutaminases. For example, the transamidation reaction between a millions of unique peptides and a biotinylated amine donor can be quantified on one or more arrays in parallel and the sequences of the peptides with the highest signal output (i.e., the top substrates) can be determined. Thereafter, in a next step 110 of the method 100, the top substrates can be resynthesized and tested for transglutaminase activity in a standalone (on array or in solution) assay. Accordingly, the step 110 includes characterization of the candidate transglutaminases in the presence of the top substrates identified in the step 108.

Characterization of candidate transglutaminases can include determination of the parameters such as specificity, selectivity, affinity, activity, and the like. Moreover, two or more candidate transglutaminases can be characterized for orthogonality. Here, the ability of the candidate transglutaminases to act on the same substrates can be identified. In the case that two different transglutaminases are unable to act on the same substrate or substrates, the two different transglutaminases can be said to be orthogonal. However, in the case that the two different transglutaminases are able to act on one or more of the same substrates, but with different degrees of activity, the two different transglutaminases can be said to be semi-orthogonal. In one aspect, a peptide substrate array can deliver a readout for all viable 5-mer peptides sequences at once. Therefore, data collected from the substrate libraries can be used to identify differences in substrate specificity for each candidate transglutaminase for the identification of orthogonal, semi-orthogonal, and non-orthogonal transglutaminases.

The step 110 of the method 100 can further include characterization of the ability of the candidate transglutaminases to perform site-specific labeling on protein substrates. In one aspect assay, the top substrate sequences identified in the step 108 can be further analyzed in the step 110 both on array and in solution. Experiments can also be performed to quantify cross-reactivity of candidate transglutaminases with various substrates. In one aspect, a protein scaffold may be useful for labeling approaches as epitope (i.e., substrate sequence) containing loops can be grafted onto the scaffold for presentation to binders or enzymes. One approach including the use of scaffolds is described in PCT App. Pub. No. WO 2012/150321 to Andres et al. filed on 4 May 2012. Example scaffolds can advantageously include one or more FK506-binding protein (FKBP) domains as a site for grafting epitope-containing loops.

Labeling of the scaffold protein with candidate transglutaminases can be achieved under a variety of conditions. Factors that can be varied for labeling experiments include the ratio of substrate to transglutaminase enzyme, the ratio of one substrate to another substrate, the labeling time, pH, or the like. Notably, a substrate refers to any peptide, protein, or other structure including one or more amine-donor or acyl-donor substrates sequences. Example substrates include scaffold proteins having an acyl-donor or amine-donor substrate sequence grafted thereon, a detectable label conjugated to or otherwise associated with an acyl-donor or amine-donor substrate sequence, an acyl-donor or amine-donor substrate sequence in isolation, the like, and combinations thereof. Labeling yield can be measured over time using standard techniques, such as sodium dodecyl sulfate polyacrylamide gel electrophoresis (SDS-PAGE) in combination with optical (e.g., bright field, fluorescence) detection. For example, a first substrate can include one or more detectable labels. Cross-linking of the first substrate to a second substrate (e.g., the protein scaffold) can be analyzed by identifying a molecular weight shift on an SDS-PAGE gel followed by detection of the label within the gel.

Labels for use with embodiments of the present disclosure include any suitable label that can be combined with a transglutaminase substrate. Examples of suitable labels include fluorescent labels, chemiluminescent labels, radio-labels, chemical labels (e.g., incorporating "click" chemistry), haptens, a toxin, the like, and combinations thereof. More generally, a suitable label is compatible with at least one substrate of the transglutaminase (e.g., an acyl-donor substrate or amine-donor substrate) in that the label does not eliminate the ability of the transglutaminase to act on the labeled substrate. Further, a suitable label can produce a signal that is detectable relative to an unlabeled transglutaminase substrate. Specific examples of detectable labels for use in any appropriate embodiment herein can comprise fluorescein, rhodamine, TEXAS RED fluorescent dye, phycoerythrin, OREGON GREEN fluorescent dyes (e.g., OREGON GREEN 488 fluorescent dye, OREGON GREEN 514 fluorescent dye, and the like) ALEXA FLUOR 488 fluorescent dye, ALEXA FLUOR 647 fluorescent dye (Molecular Probes, Eugene, Oreg.), Cy3, Cy5, Cy7, biotin, ruthenium, DYLIGHT fluorescent agents, including but not limited to DYLIGHT 680 fluorescent dye, CW 800, trans-cyclooctene, tetrazine, methyltetrazine, and the like. Examples of haptens include biotin, digoxigenin, dinitrophenyl, and the like. Examples of toxins include amatoxins (e.g., amanitin), maitansinoids, and the like.

In some embodiments, the step 110 can further include identification and characterization of the three-dimensional (3D) crystal structure of the transglutaminase to provide further insight into the nature of the transglutaminase. The crystal structure of the transglutaminase can be performed in the presence of absence of one or more substrates, cofactors, or the like. Analysis of the crystal structure can provide insight into possible locations for site-specific mutagenesis for improving the properties of the transglutaminase. Crystallization of a candidate transglutaminase with a particular substrate sequence can further reveal interactions between the transglutaminase and substrate sequence to inform modifications to either or both of the transglutaminase and substrate sequence to tailor the properties of the transglutaminase to a particular application. Moreover, analysis of the crystal structure can serves as an independent confirmation of the reliability of array-based substrate discovery (see Example 5).

In a step 112 the method 100, substrate sequences identified in the step 108 and characterized in the step 110 are selected for use in downstream application of a selected candidate transglutaminase. In general, a particular acyl-donor or amine-donor substrate sequence may be unique to a given transglutaminase. Accordingly, for a given application, it may be useful to first select a transglutaminase and then select one or more substrate sequences. For applications where specificity and selectivity are important (e.g., orthogonal labeling with two or more transglutaminases), the step 112 can include selecting substrate sequences that are specifically and selectively labeled by the selected transglutaminase. However, other applications may benefit from selecting substrate sequences that can be acted on by more than one transglutaminase. Substrates can also be selected to achieve a particular degree of transglutaminase activity when it is useful to achieve faster or slower reaction times. To further tailor the selected substrate sequences, after the step 112 the method 100 can return to the step 106 for additional rounds of screening. In this case, the selected substrates can be extended, matured, or the like in subsequent rounds of screening on the peptide array. Example methods for extension and maturation of peptide sequences are described in U.S. Pat. Pub. No 2015/0185216 to Albert et al. filed on 19 Dec. 2014.

In yet other embodiments, it may be useful to provide site-specific labeling with promiscuous transglutaminase activity. A promiscuous transglutaminase may be useful if the substrate is not recombinantly produced, if the labeling site and label ratio can be controlled or are not of critical importance for the application on hand, or the like. One example of labeling with a promiscuous transglutaminase is the conjugation of payloads to deglycosylated or glycosylated IgG. However, transglutaminases having non-specific activity may be limited to a narrow range of possible applications. Accordingly, in other situations, it may be useful to provide a transglutaminase having specific activity for only a particular substrate or group of like substrates.

In summary, the method 100 can be used to identify and characterize one or more candidate transglutaminases along with one or more corresponding substrates. Hypothetical or known transglutaminases can be expressed and screened on substrate libraries to identify preliminary substrate sequences that elicit the desired transglutaminase activity. Top substrates can then be selected and optionally refined in an iterative manner, thereby resulting in a transglutaminase-substrate combination that can be implemented for a variety of applications.

One embodiment is directed to a structure, a microbial transglutaminse, a first substrate tag, and a second substrate tag, wherein the first substrate tag is attached to the structure; wherein the first substrate tag comprises an acyl-donor tag having at least 80% sequence identity to any one of the peptide sequences selected from the group consisting of YRYRQ (SEQ ID NO:1), PRYRQ (SEQ ID NO:38), GGGYRYRQGGGP (SEQ ID NO:105), GGGSYRYRQGGGS (SEQ ID NO:106), GGGSPRYRQGGGS (SEQ ID NO:107), GGGSRWRQRGGGS (SEQ ID NO:108), GGGSRVRQRGGGS (SEQ ID NO:109), GGGSPKFRQGGGS (SEQ ID NO:110), GGGSPKQRQGGGS (SEQ ID NO:111), RWRQR (SEQ ID NO:112), RVRQR (SEQ ID NO:113), PKFRQ (SEQ ID NO:114), and PKQRQ (SEQ ID NO:115); wherein the second substrate tag comprises an amine-donor tag; wherein the structure is selected from a recombinant protein, a detectable label, and a chemically synthesized structure; wherein the microbial transglutaminase has at least 80% sequence identity to the *Kutzneria albida* microbial transglutaminase (SEQ ID NO:6); and wherein the microbial transglutaminase cross-links the first substrate tag to the second substrate tag by forming an isopeptide bond between the acyl-donor tag and the amine-donor tag. In another embodiment, the detectable label is selected from a biotin moiety, a fluorescent dye, a ruthenium label, a radiolabel, and a chemiluminescent label. In another embodiment, the acyl-donor tag has the peptide sequence of any one of the peptide sequences selected from the group consisting of YRYRQ (SEQ ID NO:1), GGGYRYRQGGGP (SEQ ID NO:105), GGGSYRYRQGGGS (SEQ ID NO:106), GGGSPRYRQGGGS (SEQ ID NO:107), GGGSRWRQRGGGS (SEQ ID NO:108), GGGSRVRQRGGGS (SEQ ID NO:109), GGGSPKFRQGGGS (SEQ ID NO:110), GGGSPKQRQGGGS (SEQ ID NO:111), RWRQR (SEQ ID NO:112), RVRQR (SEQ ID NO:113), PKFRQ (SEQ ID NO:114), and PKQRQ (SEQ ID NO:115). In another embodiment, the recombinant microbial transglutaminase is the *Kutzneria albida* microbial transglutaminase (SEQ ID N0:6). In another embodiment, the chemically synthesized structure comprises at least one of a protein, a peptide, an oligonucleotide, a carboxybenzyl group, and a polyethylene glycol (PEG) polymer. In another embodiment, the amine-donor tag has a peptide sequence selected from the group consisting of RYESK (SEQ ID NO:2), RYSKY (SEQ ID NO:25), AYRTK (SEQ ID NO:26), RYRSK (SEQ ID NO:27), RYGKS (SEQ ID NO:28), YKGRG (SEQ ID NO:29), ARSKL (SEQ ID NO:30), NYRFK (SEQ ID NO:45), YQKWK (SEQ ID NO:46), YKYKY (SEQ ID NO:47), RWKFK (SEQ ID NO:48), RFYSK (SEQ ID NO:49), YKYAK (SEQ ID NO:50), YRYAK (SEQ ID NO:51), RYSYK (SEQ ID NO:52), YKSFK (SEQ ID NO:53), YKSWK (SEQ ID NO:54), KYRYK (SEQ ID NO:55), YKYNK (SEQ ID NO:56), PYKYK (SEQ ID NO:57), FYKYK (SEQ ID NO:58), and FYESK (SEQ ID NO:59). In another embodiment, the amine-donor tag is attached to a second structure, wherein the second structure is selected from a second recombinant protein, a second detectable label, and a second chemically synthesized structure. In another embodiment, the second detectable label is selected from a biotin moiety, a fluorescent dye, a ruthenium label, a radiolabel, and a chemiluminescent label. In another embodiment, the second chemically synthesized structure comprises at least one of a protein, a peptide, an oligonucleotide, a carboxybenzyl group, and a polyethylene glycol (PEG) polymer. In another embodiment, the substrate tag is flanked on the N-terminus, on the C-terminus, or both the N-terminus and C-terminus with a linker. In another embodiment, the linker is a 3 amino acid long linker or a 4 amino acid long linker. In another embodiment, the linker is synthesized by using a mixture of glycine and serine having a 3:1 ratio. In another embodiment, the linker consists of the sequence GGGS (SEQ ID NO:116). In another embodiment, the linker is synthesized by using a mixture of glycine and proline having a 3:1 ratio. In another embodiment, the linker consists of the sequence GGGP (SEQ ID NO:118). In another embodiment, the linker consists of the sequence GGG (SEQ ID NO:119).

One embodiment is directed to a kit for forming an isopeptide bond in the presence of a microbial transglutaminase, the kit comprising an isolated microbial transglutaminase having at least 80% sequence identity to the *Kutzneria albida* microbial transglutaminase (SEQ ID NO:6). In a related embodiment, the kit further comprises one of a first substrate, wherein the first substrate comprises an acyl-donor tag having at least 80% sequence identity to the any one of the peptide sequences selected from the group consisting of YRYRQ (SEQ ID NO:1), GGGYRYRQGGGP (SEQ ID NO:105), GGGSYRYRQGGGS (SEQ ID NO:106), GGGSPRYRQGGGS (SEQ ID NO:107), GGGSRWRQRGGGS (SEQ ID NO:108), GGGSRVRQRGGGS (SEQ ID NO:109), GGGSPKFRQGGGS (SEQ ID NO:110), GGGSPKQRQGGGS (SEQ ID NO:111), RWRQR (SEQ ID NO:112), RVRQR (SEQ ID NO:113), PKFRQ (SEQ ID NO:114), and PKQRQ (SEQ ID NO:115), and a second substrate, wherein the second substrate comprises an amine-donor tag having at least 80% sequence identity to the peptide sequence RYESK (SEQ ID NO:2). In another embodiment, at least one of the first substrate and the second substrate includes a detectable label. In another embodiment, the detectable label is selected from a biotin moiety, a fluorescent dye, a ruthenium label, and a chemiluminscent label. In another embodiment, the acyl-donor tag has the peptide sequence of any one of the peptide sequences selected from the group consisting of YRYRQ (SEQ ID NO:1), GGGYRYRQGGGP (SEQ ID NO:105), GGGSYRYRQGGGS (SEQ ID NO:106), GGGSPRYRQGGGS (SEQ ID NO:107), GGGSRWRQRGGGS (SEQ ID NO:108), GGGSRVRQRGGGS (SEQ ID NO:109), GGGSPKFRQGGGS (SEQ ID NO:110), GGGSPKQRQGGGS (SEQ ID NO:111), RWRQR (SEQ ID NO:112), RVRQR (SEQ ID NO:113), PKFRQ (SEQ ID NO:114), and PKQRQ (SEQ ID NO:115). In another embodiment, the kit further comprises the other one of the first substrate and the second substrate. In another embodiment, the isolated microbial transglutaminase is expressed and isolated in the presence of ammonium. In a related embodiment, the ammonium is present at a concentration of at least about 10 µM.

EXAMPLES

Example 1

Identification of the *K. albida* Microbial Transglutaminase

Establishing a viable and robust, enzymatic, industrial-scale method for site-specific conjugation approaches like antibody-drug conjugates makes high demands on the coupling enzyme. Among other factors, it may be useful for such approaches to have a high reaction rate, conjugation efficacy, and substrate specificity. Further, it may be useful for such approaches to be economical in production, include an enzyme having a low molecular weight, an enzyme that is independent of cofactors, the like, and combinations thereof. For discovery of new microbial transglutaminases, a search for homologs of this enzyme that may fulfill all the mentioned criteria was performed using the amino acid sequence of *S. mobaraensis* protein-glutamine gamma-glutamyltransferase as a query. This yielded the hypothetical gene product KALB_7456 from bacteria *K. albida* DSM 43870, a spore-forming gram-positive bacterium which was sequenced in 2014 (Rebets et al., 2014. BMC genomics 15: 885).

The web interface of NCBI Protein BLAST tool was used to search for sequences similar to the MTG of *Streptomyces mobaraensis*. The amino acid sequence of *S. mobaraensis* protein-glutamine gamma-glutamyltransferase (UniProt accession number P81453) was entered as a query. The amino acid sequence of *S. mobaraensis* protein-glutamine gamma-glutamyltransferase is as follows:

(SEQ ID NO: 5)
MRIRRRALVFATMSAVLCTAGFMPSAGEAAADNGAGEETKSYAETYRLTA

DDVANINALNESAPAASSAGPSFRAPDSDDRVTPPAEPLDRMPDPYRPSY

GRAETVVNNYIRKWQQVYSHRDGRKQQMTEEQREWLSYGCVGVTWVNSGQ

YPTNRLAFASFDEDRFKNELKNGRPRSGETRAEFEGRVAKESFDEEKGFQ

RAREVASVMNRALENAHDESAYLDNLKKELANGNDALRNEDARSPFYSAL

RNTPSFKERNGGNHDPSRMKAVIYSKHFWSGQDRSSSADKRKYGDPDAFR

PAPGTGLVDMSRDRNIPRSPTSPGEGFVNFDYGWFGAQTEADADKTVWTH

GNHYHAPNGSLGAMHVYESKFRNWSEGYSDFDRGAYVITFIPKSWNTAPD

KVKQGWP

Manual screening of the results for E-values of less than $10^{-10}$ and polypeptide sequences shorter than that of *S. mobaraensis* MTG yielded hypothetical gene product KALB_7456 (SEQ ID NO:6) from bacterial strain *Kutzneria albida* DSM 43870 (GenBank accession number AHI00814.1; UniProt accession number W5WHY8). The amino acid sequence of gene product KALB_7456 is as follows:

(SEQ ID NO: 6)
MHKWFLRAAVVAAVGFGLPTLIATTAQAAAVAAPTPRAPLAPPLAEDRSY

RTWRVEDYVEAWERYHGREMTEDERENLARGCIGVTVVNLNREDLSNPPL

NLSFGSLRTAEAVQAALNKIVDTHPSPAQYEAAVAKDPILKRLKNVVKAL

PSWIDSAKLKASIFSKRFYSWQNPDWSEERAHTTYRPDRETDQVDMSTYR

YRARPGYVNFDYGWFDQDTNTWWHANHEEPRMVVYQSTLRHYSRPLQDFD

EQVFTVAFAKKD

Sequence alignment of the *S. mobaraensis* and the *K. albida* sequences with Clustal Omega 1.2.1 yielded a value of 32% in the percent identity matrix and identified conservation of the catalytically active residues of *S. mobaraensis* MTG (C140, R331, and H350 based on P81453 numbering (SEQ ID NO:5)). The ProP 1.0 Server from the Technical University of Denmark was used to predict the propeptide and signal sequences of the hypothetical *K. albida* microbial transglutaminase. The only predicted propeptide cleavage site was VAAPTPR/AP (residues 31 to 39 of SEQ ID NO:6) with a score (0.513) above the threshold, where the slash mark in between the amino acids R and A indicates the predicted cleavage site.

Figure 2A:
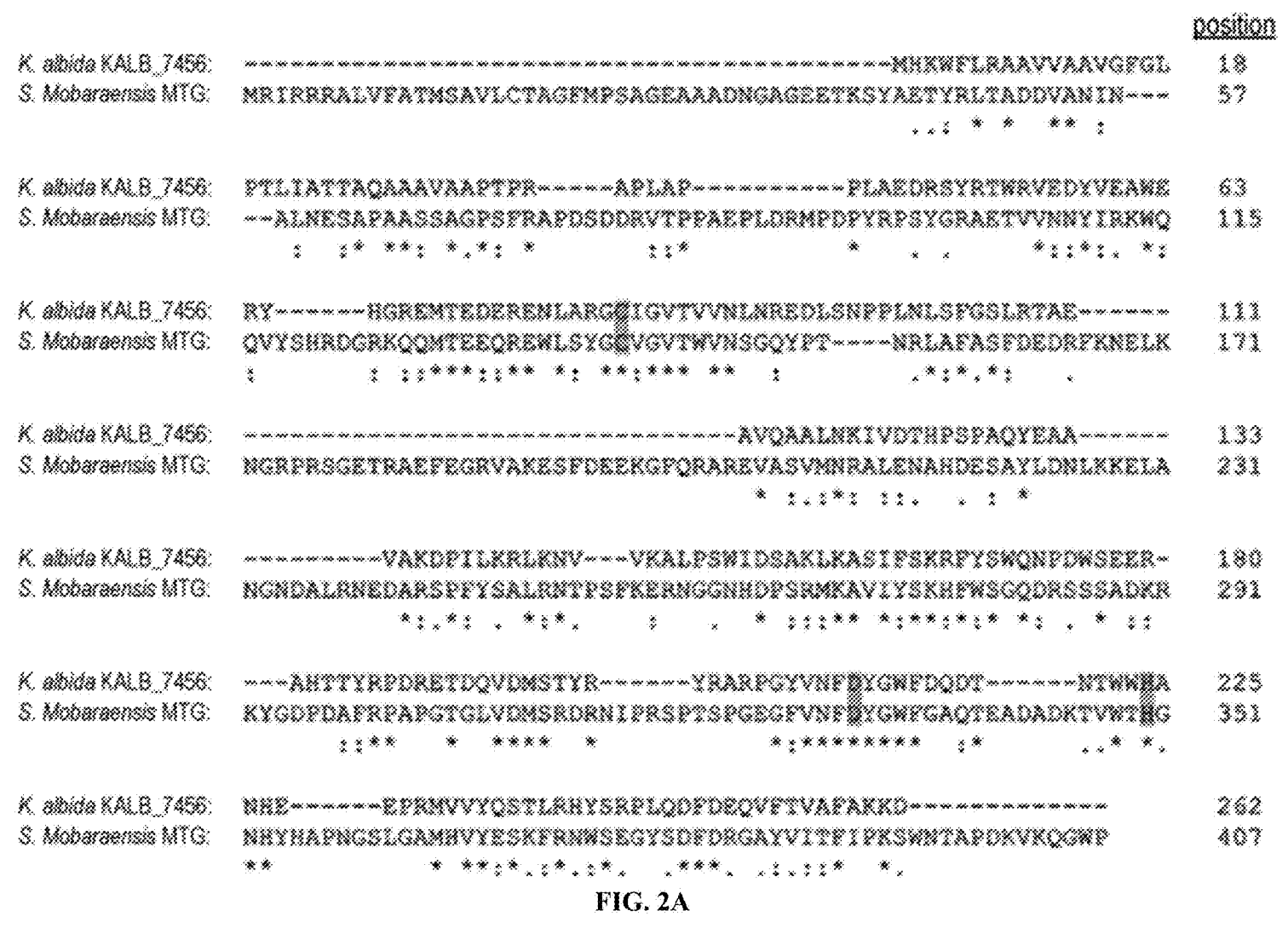
Figure 2B:
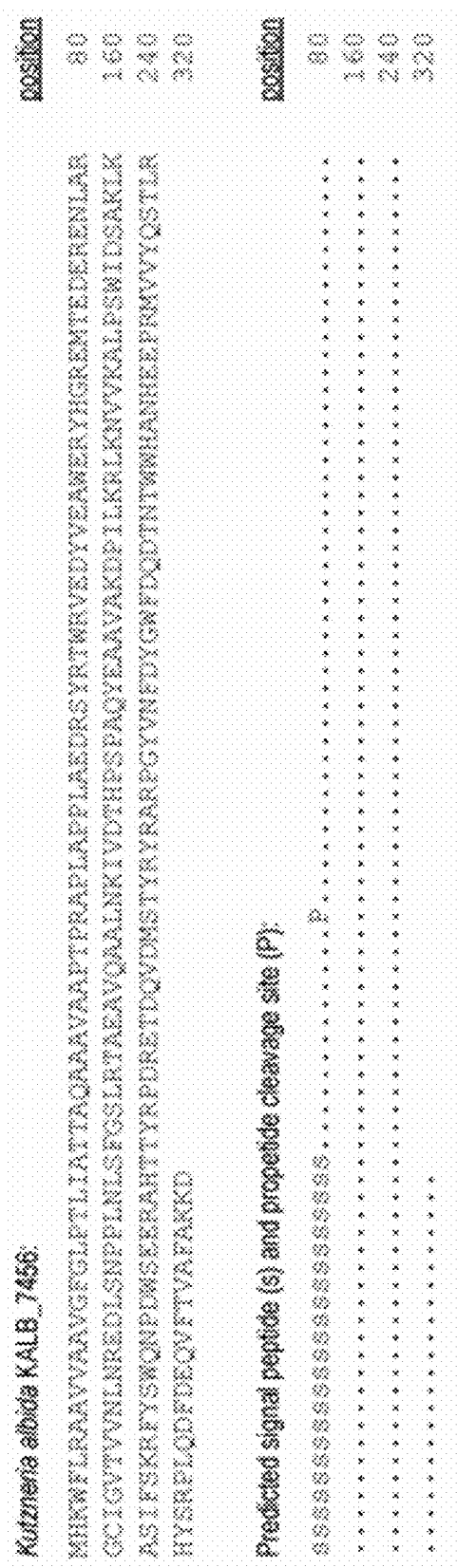
FIG. 2B is an amino acid sequence of the hypothetical transglutaminase KALB_7456 from *K. albida* (SEQ ID NO:6) including a general cleavage site prediction as determined by ProP 1.0 (Duckert et al., 2004. *Protein Engineering, Design and Selection* 17: 107-112), with both predicted signal peptide sequence ('s') and propeptide cleavage site ('P') indicated.
Figure 2C:
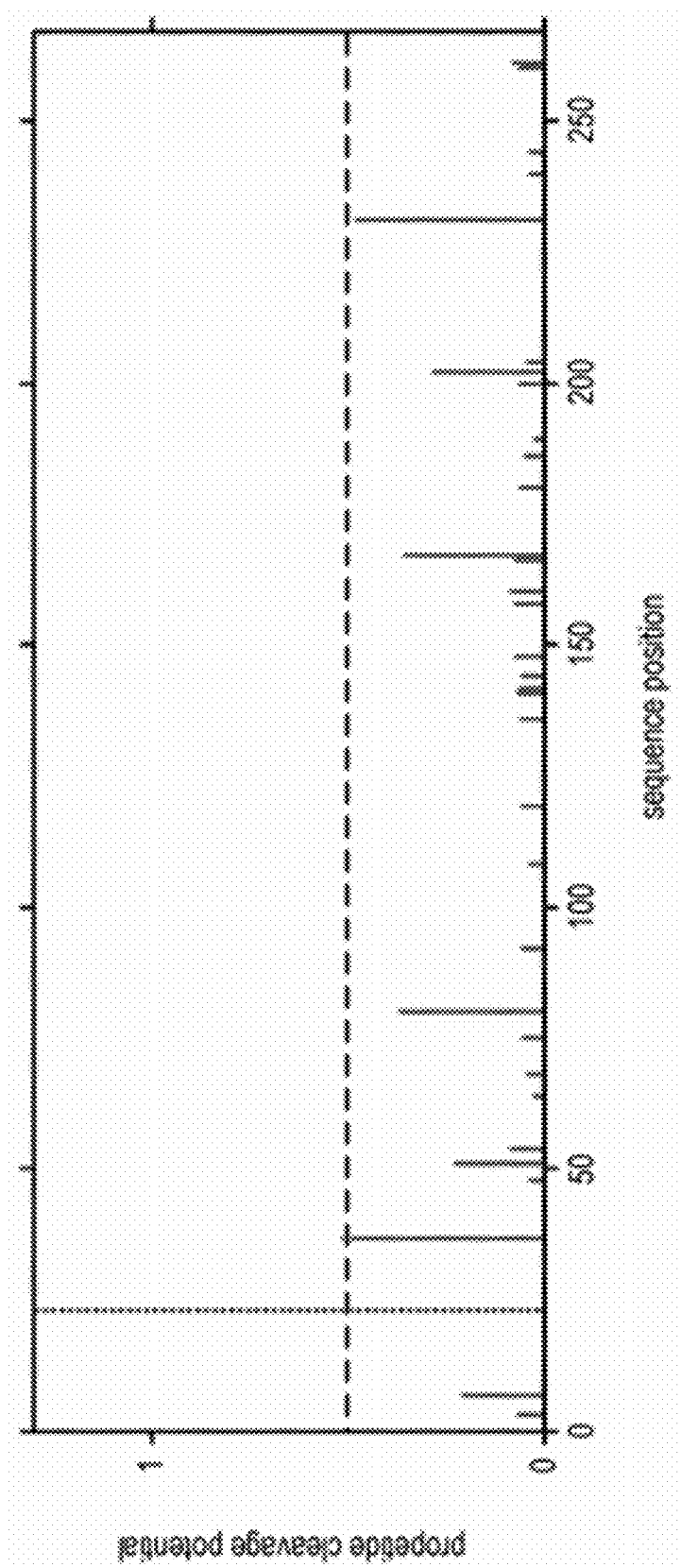
FIG. 2C is a bar graph showing propeptide cleavage potential as a function of the amino acid sequence position for the hypothetical transglutaminase KALB_7456 from *K. albida* as determined by ProP 1.0. The dashed line indicates the propeptide cleavage potential threshold, and the dotted line indicates the amino acid position predicted for signal peptide.

Comparing the primary structures of the *S. mobaraensis* (SEQ ID NO:5) and *K. albida* (SEQ ID NO:6) gene products showed 30% similarity with a distinct conservation of active site residues (FIG. 2A), indicating that the enzymatic structure and function may be preserved. The full *K. albida* gene product is significantly smaller than that of *S. mobaraensis* MTG, with the *K. albida* gene product amounting to a calculated molecular weight of 30.1 kDa. As *S. mobaraensis* MTG is produced as an inactive proenzyme and processed by extracellular proteases to yield the 38 kDa active form, a similar activation mechanism was predicted for the hypothetical *K. albida* MTG and the ProP 1.0 server was used to analyze the probability for signal and propeptide sequences in the N-terminal region of the protein (FIGS. 2B and 2C). The sequence VAAPTPR/AP (residues 31 to 39 of SEQ ID NO:6) was the only predicted propeptide cleavage site, where cleavage occurs between the amino acids arginine and proline as indicated by the forward slash. The sequence VAAPTPR/AP (residues 31 to 39 of SEQ ID NO:6) corresponds with the dispase site SAGPSFR/AP (residues 68 to 76 of SEQ ID NO:5) in *S. mobaraensis* MTG but putatively has no dispase reactivity as phenylalanine is a required residue in the enzymes recognition motif. Additionally, a signal peptide was predicted by the ProP 1.0 server with a high-probability cleavage site GLPTLIA/TT (residues 17 to 25 of SEQ ID NO:6). However, the predicted signal peptide cleavage site bears no sequence resemblance to the significantly longer *S. mobaraensis* MTG pre-sequence or other known signal peptides. Based on the predicted signal peptide and propeptide cleavage site, the molecular weights of the mature *K. albida* transglutaminase, the pro-enzyme, and the pre-pro-enzyme were calculated to be 26.4 kDa, 27.7 kDa, and 30.1 kDa, respectively.

Example 2

Parallel Construct Evaluation for Recombinant Production of KalbTG

To rapidly screen expression conditions for the hypothetical *K. albida* transglutaminase (KalbTG), we inserted the synthetic genetic insert into multiple expression vectors designed for the soluble cytosolic or periplasmic expression in *E. coli* using a fragment exchange system (Geertsma, et al. 2011. *Biochemistry* 50(15): 3272-3278).

Figure 3A:
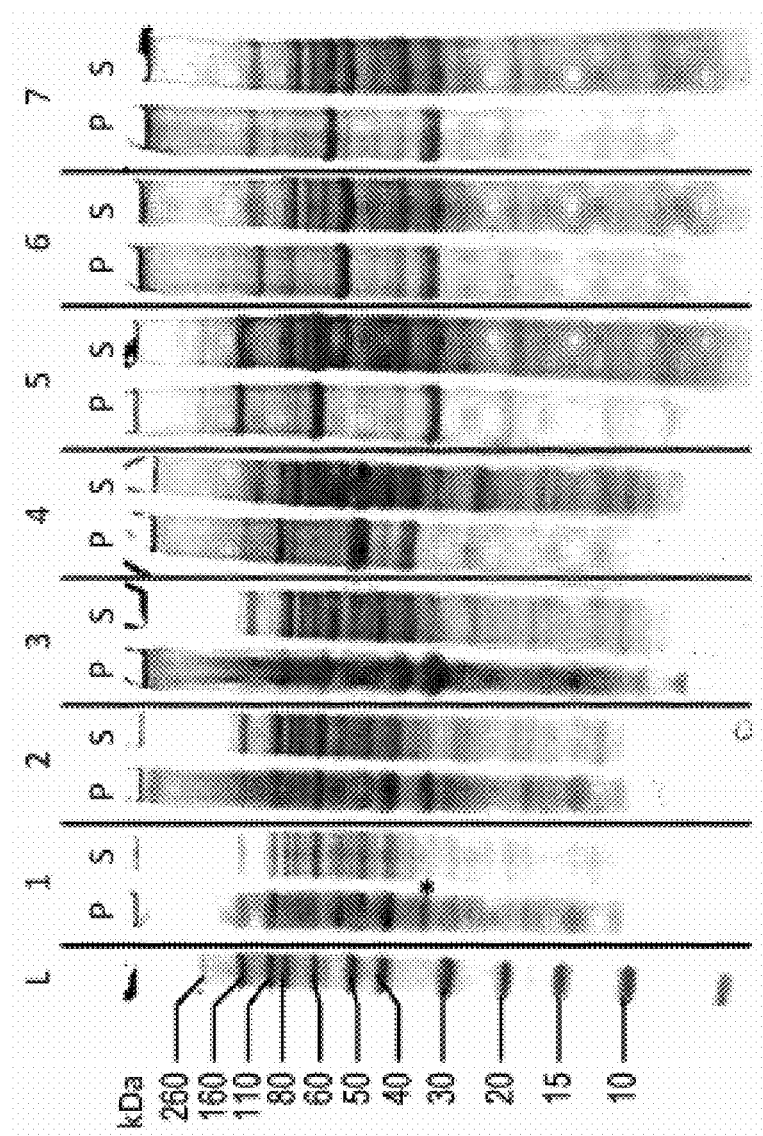
FIG. 3A is an optical image of an SDS-PAGE gel showing an expression profile for *K. albida* transglutaminase (KalbTG) fusion proteins. Amino-terminal fusion partners are grouped in adjacent lanes as indicated by lane pairs numbered 1-7 (1: 8×-His tag; 2: dsbA signal peptide; 3: ompT signal peptide; 4: *E. coli* SlyD (EcSlyD); 5: 2×EcSlyD; 6: FkpA; 7: maltose binding protein). The lane labeled 'L' was loaded with a standard molecular weight ladder (values shown in kDa). Individual lanes labeled as 'P' and 'S' denote insoluble (pellet) and soluble (supernatant) fractions of *E. coli* cell lysate, respectively. The coomassie blue stained protein band representing His-KalbTG is marked by an asterisk (*) in lane pair 1.
Figure 3B:
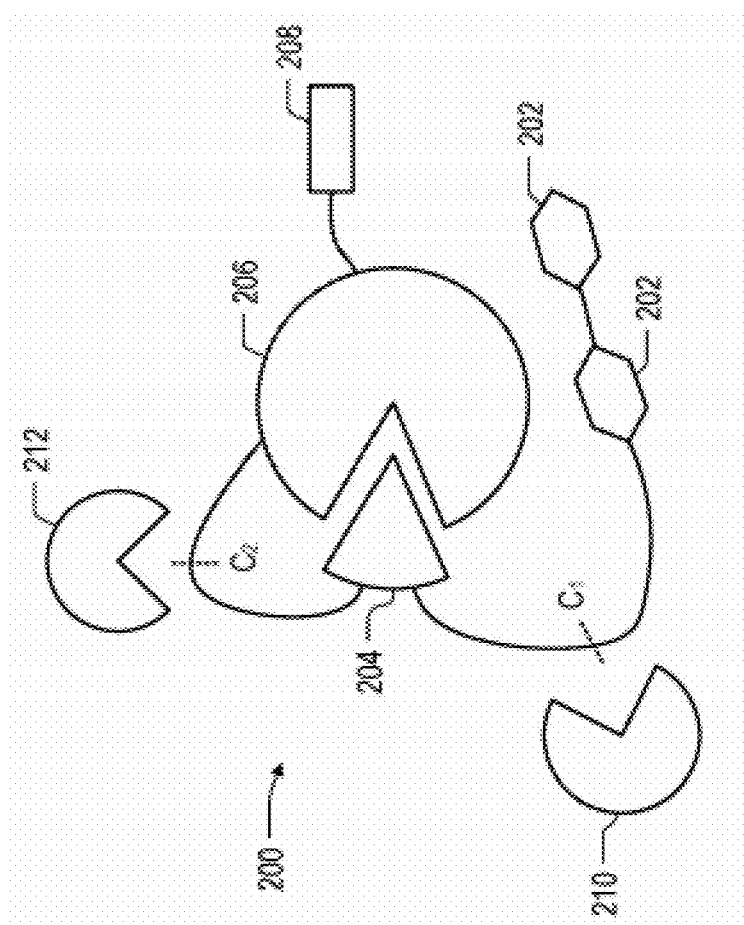
FIG. 3B is a schematic representation of the 2×SlyD-fusion protein expression and purification strategy. N-terminal fusion with two moieties of sensitive-to-lysis D (SlyD) protein confers solubility and is cleavable by factor Xa. The enzyme is further matured by cleavage of a propeptide sequence with trypsin.
Figure 3C:
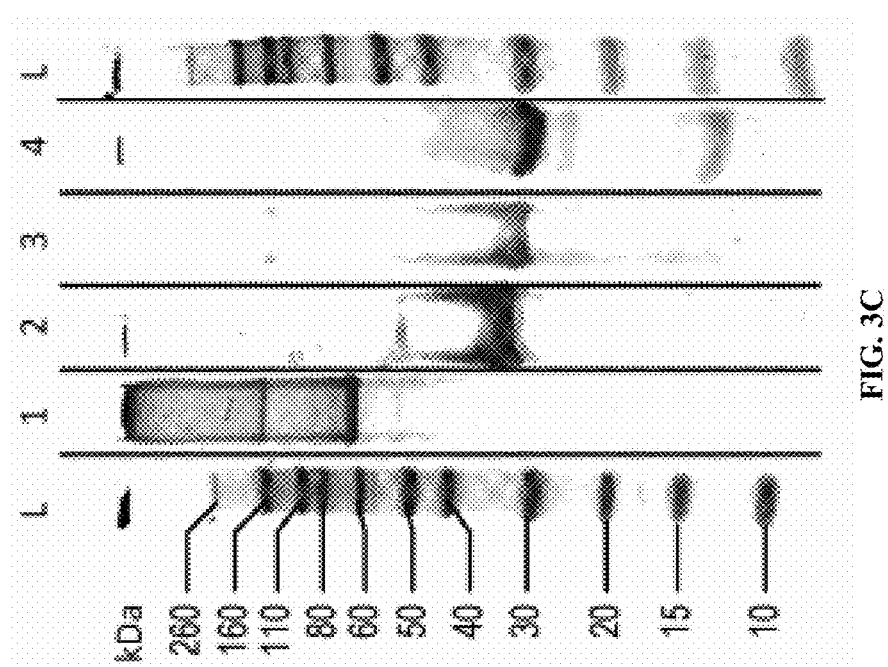
FIG. 3C is an image of an SDS-PAGE gel showing the modular purification of KalbTG. The lanes labeled 'L' were loaded with a standard molecular weight ladder (values shown in kDa). Lane 1: Fraction containing 2×SlyD-KalbTG from first Ni$^+$-IMAC gradient elution (0-250 mM Imidazole). Lane 2: KalbTG proenzyme purified by Ni$^+$-IMAC gradient elution, on-column factor Xa digest, and size exclusion chromatography. Lane 3: Fraction from second Ni$^+$-IMAC gradient elution after consecutive on-column digests with factor Xa and trypsin (0-250 mM imidazole). Lane 4: Concentrate of lane 3, filtered by a 50,000 molecular weight cut-off (MWCO) membrane.

Initial screening at the 5 ml scale provided clear evidence that proteins with the anticipated electrophoretic mobility of full length KalbTG fusions were expressed, and that a fusion with tandem SlyD chaperones (Scholz, et al. 2005. *Journal of Molecular Biology* 345(5): 1229-1241) yielded the highest amount of soluble protein among all the constructs tested (FIG. 3A). The expression of this construct was further optimized by screening different incubation times and temperatures, Isopropyl β-D-1-thiogalactopyranoside (IPTG) inducer concentrations and induction times, media types and volumes. With reference to FIGS. 3B and 3C, the modular nature of the chosen fusion construct afforded the SlyD fusion protein, the pro-enzyme, and the activated enzyme by a combination of sequential purification and proteolytic cleavage steps. The expression construct 200 included, starting from N-terminus, two sequential SlyD chaperones 202, a factor Xa protease cleavage site (C$_1$), the KalbTG pro-peptide 204, a trypsin protease cleavage site (C$_2$) the KalbTG enzyme 206, and an 8×-histidine tag 208. The SlyD chaperones 202 are cleaved from the expression construct 200 with a factor Xa protease 210. Further, the pro-peptide 204 is cleaved from the KalbTG enzyme 206 with a trypsin protease 212 resulting in an activated form of the KalbTG construct 200. The purified and activated enzyme remained stable at 4° C. and over multiple freeze-thaw cycles. The melting point of the purified and activated enzyme was determined to be 48.9° C. using differential scanning calorimetry (DSC). It will be appreciated that the method described herein represents one of many viable purification strategies. Further, the described parallel cloning approach enables reevaluation of different constructs and lab-scale production processes in an efficient and economical manner.

For the production of KalbTG, the gene sequences encoding for hypothetical *K. albida* microbial transglutaminase, including both the predicted signal and propeptide (KalbTGpp), including only the predicted propeptide (kalbTGt3), excluding the predicted signal and propeptide (kalbTGt1), or excluding the predicted signal and inserting an additional factor Xa cleavage site after the propeptide (kalbTGt2), were codon optimized for *E. coli* expression (Roche Sequence Analysis Web interface) chemically synthesized (GeneArt, ThermoFisher, Regensburg) and cloned via fragment exchange (Fx) cloning (Geertsma, et al. 2011, *Biochemistry* 50(15): 3272-3278) into a vector conferring two N-terminal moieties of Sensitive-to-lysis D chaperones (SlyD, UniProt entry P0A9K9, truncated after Asp165, (Scholz et al. 2005, *Journal Of Molecular Biology* 345(5): 1229-1241) followed by protease factor Xa cleavage site and conferring a C-terminal 8×-His tag. The amino acid sequence of SlyD truncated after Asp165 is as follows:

(SEQ ID NO: 7)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFLAET

DQGPVPVEITAVEDDHVVVDGNHMLAGQNLKFNVEVVAIREATEEELAHG

HVHGAHDHHHDHDHD

The vector is based on the pQE-80 series by Qiagen, comprising IPTG-inducible protein expression by T5 promotor and conferring resistance to ampicillin. The expression construct used for all experiments described in this work was termed EcSlyD2-Xa-KalbTGt3-8×His. Additionally, as an initial expression screen, fragment exchange cloning was performed in vectors conferring N-terminal fusions to 8×-His tag, dsbA, and ompT signal peptides, single SlyD or FkpA chaperone moieties and maltose binding protein (MBP). Plasmid preparation and transformation of chemically competent *E. coli* Bl21 Tuner cells with the expression plasmid was performed according to standard molecular biology protocols (Green, et al., 2012. "Molecular Cloning: A Laboratory Manual", Cold Spring Harbor Laboratory Press).

To prepare active KalbTG enzyme, between 0.4 liters and 1 liter Terrific Broth (TB) medium was inoculated with overnight culture of EcSlyD2-Xa-KalbTGt3-8×His-tag in *E. coli* Bl21 Tuner in a ratio of 1:50. The amino acid sequence of the EcSlyD2-Xa-KalbTGt3-8×His-tag expression construct was as follows:

(SEQ ID NO: 8)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFLAET

DQGPVPVEITAVEDDHVVVDGNHMLAGQNLKFNVEVVAIREATEEELAHG

HVHGAHDHHHDHDHDGGGSGGGSGGGSGGGSGGGSGGGMKVAKDLVVSLA

YQVRTEDGVLVDESPVSAPLDYLHGHGSLISGLETALEGHEVGDKFDVAV

GANDAYGQYDENLVQRVPKDVFMGVDELQVGMRFLAETDQGPVPVEITAV

EDDHVVVDGNHMLAGQNLKFNVEVVAIREATEEELAHGHVHGAHDHHHDH

DHDGGGSGGGSGGGSGGGSGGGSGGGIEGRMGGGSTTAQAAAVAAPTPRA

PLAPPLAEDRSYRTWRVEDYVEAWERYHGREMTEDERENLARGCIGVTVV

NLNREDLSNPPLNLSFGSLRTAEAVQAALNKIVDTHPSPAQYEAAVAKDP

ILKRLKNVVKALPSWIDSAKLKASIFSKRFYSWQNPDWSEERAHTTYRPD

-continued
RETDQVDMSTYRYRARPGYVNFDYGWFDQDTNTWWHANHEEPRMVVYQST

LRHYSRPLQDFDEQVFTVAFAKKDGGGSGHHHHHHHH

Cells were incubated at 37° C., 180 rpm in baffled shaker flasks and protein expression was induced with 1 mM IPTG after cell density had reached an $OD_{600\,nm}$ of 0.8-1.2. Cells were harvested by centrifugation (7878×g for 30 at 4° C.). Supernatants were discarded and cell pellets were stored at −80° C. or immediately processed for nickel immobilized metal affinity chromatography ($Ni^+$-IMAC).

For the subsequent $Ni^+$-IMAC purification of EcSlyD2-Xa-KalbTGt3-8×His, cell pellets were resuspended in 30-50 ml phosphate-buffered saline (PBS) in the presence of lysozyme and DNAse I. Cells were disrupted by high pressure homogenization at 2 kbar. To remove cellular debris, the suspension was centrifuged (17,210×g for 30 min at 4° C.).

Supernatants derived from cell disruption were filtered through a 0.45 μm polyethersulfone (PES) membrane and loaded onto a 5 ml HISTRAP chromatography column, washed with at least 5 column volumes PBS, and His-tagged protein eluted with a linear gradient from 0 to 250 mM imidazole in PBS (30 ml, 5 ml $min^{-1}$). The 3 ml fractions containing protein as identified by $Abs_{280\,nm}$ were collected, diluted in PBS and concentrated via AmiconUltra concentrators (10 000 MWCO; 5000×g for 15-30 min). The protein concentration of the fractions was determined by Bradford Assay (BioRad, according to the manufacturer's instructions). Between 5-10 μg protein per sample was analyzed by SDS-PAGE (ThermoFisher Novex, according to the manufacturer's instructions). Purified protein was aliquoted into 200 μl volumes, frozen through a short incubation in liquid nitrogen and stored at −80° C.

To cleave the SlyD chaperones and propeptide from EcSlyD2-Xa-KalbTGt3-8×His-tag, the protein was immobilized on a 5 ml HISTRAP chromatography column and on-column digest was performed with factor Xa followed with trypsin. One microgram factor Xa per 50 μg total protein was applied and incubated on column for 1.5 hours. Protease and cleaved SlyD was washed off the column with PBS.

The amino acid sequence of the EcSlyD2-Xa-KalbTGt3-8×His-tag expression construct after factor Xa digest was as follows:

(SEQ ID NO: 9)
MGGGSTTAQAAAVAAPTPRAPLAPPLAEDRSYRTWRVEDYVEAWERYHGR

EMTEDERENLARGCIGVTVVNLNREDLSNPPLNLSFGSLRTAEAVQAALN

KIVDTHPSPAQYEAAVAKDPILKRLKNVVKALPSWIDSAKLKASIFSKRF

YSWQNPDWSEERAHTTYRPDRETDQVDMSTYRYRARPGYVNFDYGWFDQD

TNTWWHANHEEPRMVVYQSTLRHYSRPLQDFDEQVFTVAFAKKDGGGSGH

HHHHHHH

Following Trypsin digest, the amino acid sequence of the KalbTG enzyme (KalbTGt3) was as follows:

(SEQ ID NO: 10)
APLAPPLAEDRSYRTWRVEDYVEAWERYHGREMTEDERENLARGCIGVTV

VNLNREDLSNPPLNLSFGSLRTAEAVQAALNKIVDTHPSPAQYEAAVAKD

PILKRLKNVVKALPSWIDSAKLKASIFSKRFYSWQNPDWSEERAHTTYRP

DRETDQVDMSTYRYRARPGYVNFDYGWFDQDTNTWWHANHEEPRMVVYQS

TLRHYSRPLQDFDEQVFTVAFAKKDGGGSGHHHHHHHH

For crystal structure analysis of KalbTG, His-tagged protein was eluted after factor Xa digest with a 0-250 mM linear imidazole gradient and a polishing step was performed using size exclusion chromatography (GE SUPERDEX 200 size exclusion media pg 16/60, PBS). Alternatively, to receive active and pure enzyme preparation, activation was performed by adding 200 μg $ml^{-1}$ trypsin onto the HISTRAP chromatography column and incubating for 15-30 min. Protease and cleaved propeptide were washed off the column with PBS and digested KalbTG was collected in the same manner as described above. To eliminate high molecular-weight impurities from active KalbTG, the enzyme preparation was filtered through AmiconUltra concentrators (50,000 MWCO). The filtrate was tested for activity via GLDH-coupled assay and purity analyzed by SDS-PAGE as shown in FIG. 3C. The remaining filtrate was divided into 200 μl aliquots, frozen in liquid nitrogen and stored at −80° C.

In another embodiment of an approach for the preparation of active KalbTG enzyme, E. coli BL21 Tuner harboring the plasmid pQE-EcSlyD2-Xa-KalbTGt1-8H (ColE1 origin; IPTG inducible T5 promoter) was inoculated into 10 L standard E. coli fermentation medium similar to Terrific Broth (yeast extract, $K_2HPO_4$, $NH_4Cl$, glycerin, antifoam, $MgSO_4.7H_2O$, $H_3PO_4$, NaOH) and containing an additional 1 g of $NH_4Cl$ per liter. The sequence of the EcSlyD2-Xa-KalbTGt1-8×His construct was as follows:

(SEQ ID NO: 11)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFLAET

DQGPVPVEITAVEDDHVVVDGNHMLAGQNLKFNVEVVAIREATEEELAHG

HVHGAHDHHHDHDHDGGGSGGGSGGGSGGGSGGGSGGGMKVAKDLVVSLA

YQVRTEDGVLVDESPVSAPLDYLHGHGSLISGLETALEGHEVGDKFDVAV

GANDAYGQYDENLVQRVPKDVFMGVDELQVGMRFLAETDQGPVPVEITAV

EDDHVVVDGNHMLAGQNLKFNVEVVAIREATEEELAHGHVHGAHDHHHDH

DHDGGGSGGGSGGGSGGGSGGGSGGGIEGRMLAPPLAEDRSYRTWRVEDY

VEAWERYHGREMTEDERENLARGCIGVTVVNLNREDLSNPPLNLSFGSLR

TAEAVQAALNKIVDTHPSPAQYEAAVAKDPILKRLKNVVKALPSWIDSAK

LKASIFSKRFYSWQNPDWSEERAHTTYRPDRETDQVDMSTYRYRARPGYV

NFDYGWFDQDTNTWWHANHEEPRMVVYQSTLRHYSRPLQDFDEQVFTVAF

AKKDGHHHHHHHH

The EcSlyD2-Xa-KalbTGt1-8×His construct had a modular composition similar (but not identical) to the construct illustrated in FIG. 3B, with one notable difference being that the EcSlyD2-Xa-KalbTGt1-8×His construct omitted the KalbTG pro-peptide 204 and the trypsin protease cleavage site ($C_2$).

Fermentation was carried out at 35° C. for 26 h, until an $OD_{600}$ of 44 was reached. Cells were harvested and resuspended in buffer containing 50 mM Tris-HCl pH 8.0, 1 mM EDTA, 1 mM DTT and 10 mM $(NH_4)_2SO_4$. Cells were disrupted by a high-pressure homogenizer at 800 bar. The resulting cellular extract was pre-treated with 1-3% Polymin-G20 and then loaded on a Q-SEPHAROSE XL chromatography media column (strong anion exchange matrix; GE Healthcare Life Sciences) at a protein concentration of approximately 30 mg/ml. Bound protein was washed with 20 mM Tris-HCl pH 8.0, 1 mM EDTA, 1 mM DTT, 10 mM $(NH_4)_2SO_4$ and 150 mM NaCl and then eluted with a 30 column volumes gradient from 150-500 mM NaCl. The eluate was dialyzed (10 kDa molecular weight cutoff) against 20 mM Tris-HCl pH 8.0, 0.1 mM EDTA, 0.1 mM DTT, 10 mM $(NH_4)_2SO_4$, 500 mM NaCl, concentrated and loaded onto a Ni-NTA column. Bound, His-tagged protein was washed with 20 mM Tris-HCl pH 8.0, 0.1 mM EDTA, 0.1 mM DTT, 10 mM $(NH_4)_2SO_4$, 500 mM NaCl, 25 mM imidazole and eluted with a 20 column volume gradient from 25-200 mM imidazole. Purified protein was dialyzed (10 kDa molecular weight cutoff) against 20 mM Tris-HCl, 1 mM EDTA, 1 mM DTT and 10 mM $(NH_4)_2SO_4$, pH 8.0, concentrated to 1.77 mg/ml, analyzed by SDS-PAGE and GLDH activity assay and frozen in 10 mg aliquots at −80° C. Prior to use, $(NH_4)_2SO_4$ was removed by dialysis with a 10 kDa molecular weight cutoff filter. Factor Xa digest was performed as described herein to remove the 2×SlyD portion from the KalbTG construct, thereby yielding the KalbTG enzyme (KalbTGt1) having the following sequence:

(SEQ ID NO: 12)
MLAPPLAEDRSYRTWRVEDYVEAWERYHGREMTEDERENLARGCIGVTVV

NLNREDLSNPPLNLSFGSLRTAEAVQAALNKIVDTHPSPAQYEAAVAKDP

ILKRLKNVVKALPSWIDSAKLKASIFSKRFYSWQNPDWSEERAHTTYRPD

RETDQVDMSTYRYRARPGYVNFDYGWFDQDTNTWWHANHEEPRMVVYQST

LRHYSRPLQDFDEQVFTVAFAKKDGHHHHHHHH

One aspect of the approach taken to express the KalbTG enzyme derived from the EcSlyD2-Xa-KalbTGt1-8×His construct includes the addition of a source of ammonium ion (i.e., $(NH_4)_2SO_4$ or $NH_4Cl$), which is a natural inhibitor of the KalbTG enzyme, to both the fermentation broth and the purification buffers. The use of ammonium (or ammonia) enables production of the KalbTG fusion protein without the need for expression or downstream cleavage of the pro-peptide sequence. The auto-catalytic activity of the KalbTG enzyme is reversibly inhibited by the presence of the ammonium ion (from the ammonium chloride in solution) until the final dialysis used to remove to the ammonium ion prior to application of the KalbTG enzyme. Surprisingly, the purification process including the use of ammonium chloride lead to an increase in KalbTG enzymatic activity of up to about 9-fold as measured by GLDH assay, thereby making the KalbTG enzyme highly competitive as compared to current commercially available MTG (See Example 3, Table 4). Accordingly, it may be useful to express, purify, or otherwise isolate a transglutaminase in the presence of ammonium chloride, another ammonium salt, or another source of ammonia.

In some embodiments, it may be useful to select a source of ammonium where the counter-ion has a neutral effect in the overall process. For example, in experiments where the ammonium counter-ion was sulfate, a negative impact on expression was observed as compared with the use of chloride as the counter-ion. However, the use of sulfate as the counter-ion may have little to no negative effect with respect to purification steps. Accordingly, it may be useful to first determine the effects of the counter-ion on expression and purification of a given transglutaminase. Moreover, the concentration of ammonium ion present during either expression or purification of a given transglutaminase may be varied. In one embodiment, the ammonium may be present at a concentration of at least about 10 µM. In another embodiment, the ammonium may be present at a concentration of at least about 100 µM. In yet another embodiment, the ammonium may be present at a concentration of at least about 1 mM. In still another embodiment, the ammonium may be present at a concentration of at least about 10 mM.

Example 3

Use of Peptide Arrays for Transglutaminase Substrate Discovery

Figure 4A:
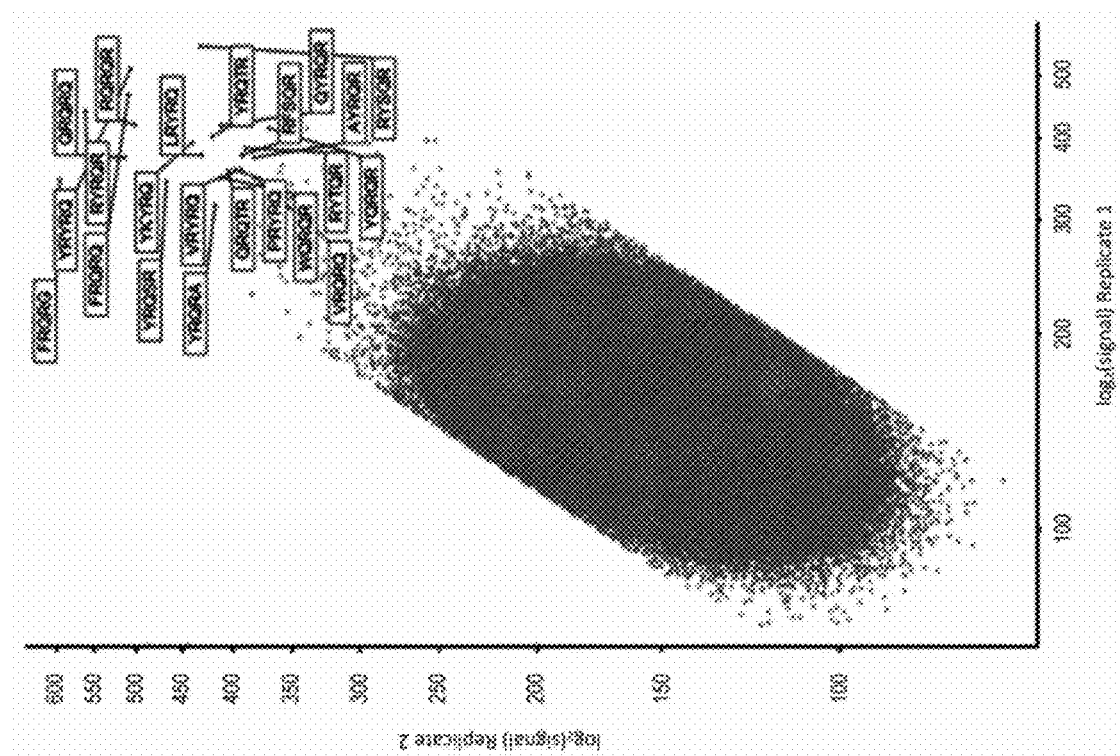
FIG. 4A is a log-log scatter plot showing the correlation between fluorescence signal data generated by KalbTG for replicate features on a 5-mer peptide array in the presence of biotinylated amine-donor substrate. Each data point represents a pair of replicate peptides from a library of 1.4 million unique peptides synthesized in duplicate. The 22 data points displaying the highest fluorescence signals are tagged by their respective 5-mer peptide sequence: YRYRQ (SEQ ID NO:1), RYRQR (SEQ ID NO:14), RYSQR (SEQ ID NO:15), FRQRQ (SEQ ID NO:16), RQRQR (SEQ ID NO:17), FRQRG (SEQ ID NO:18), QRQRQ (SEQ ID NO:19), YKYRQ (SEQ ID NO:20), QYRQR (SEQ ID NO:21), YRQSR (SEQ ID NO:32), LRYRQ (SEQ ID NO:33), YRQRA (SEQ ID NO:34), VRYRQ (SEQ ID NO:35), QRQTR (SEQ ID NO:36), YRQTR (SEQ ID NO:37), PRYRQ (SEQ ID NO:38), RFSQR (SEQ ID NO:39), WQRQR (SEQ ID NO:40), VRQRQ (SEQ ID NO:41), RYTQR (SEQ ID NO:42), AYRQR (SEQ ID NO:43), and YQRQR (SEQ ID NO:44).
Figure 4B:
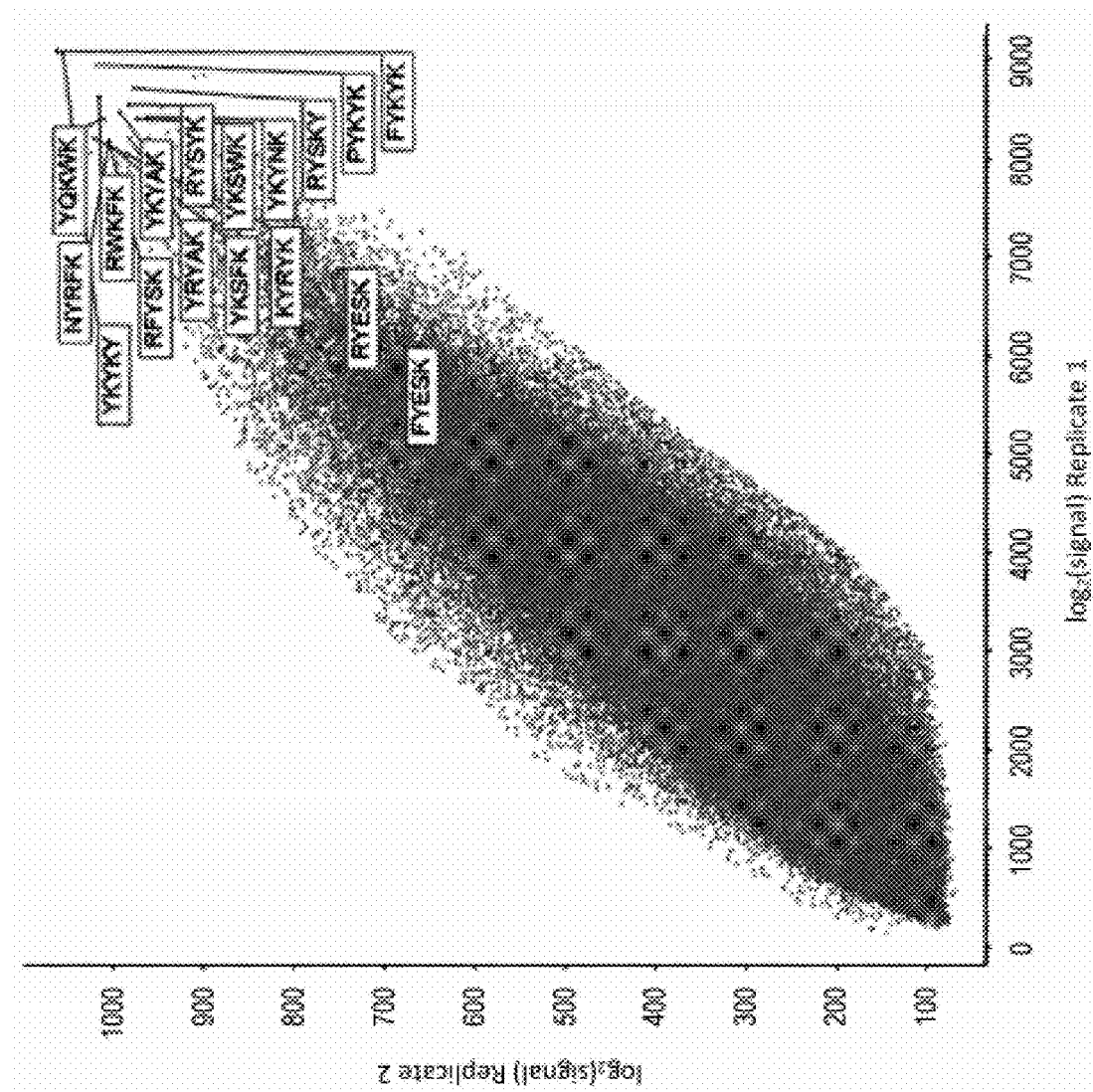
FIG. 4B is a log-log scatter plot showing the correlation between fluorescence signal data generated by KalbTG for replicate features on a 5-mer peptide array in the presence of biotinylated glutamine-donor substrate (Z-APRYRQRAAGGG-PEG-biotin). Each data point represents a pair of replicate peptides from a library of 1.4 million unique peptides synthesized in duplicate. The 17 data points displaying the highest fluorescence signals are tagged by their respective 5-mer peptide sequence: RYESK (SEQ ID NO:2), RYSKY (SEQ ID NO:25), NYRFK (SEQ ID NO:45), YQKWK (SEQ ID NO:46), YKYKY (SEQ ID NO:47), RWKFK (SEQ ID NO:48), RFYSK (SEQ ID NO:49), YKYAK (SEQ ID NO:50), YRYAK (SEQ ID NO:51), RYSYK (SEQ ID NO:52), YKSFK (SEQ ID NO:53), YKSWK (SEQ ID NO:54), KYRYK (SEQ ID NO:55), YKYNK (SEQ ID NO:56), PYKYK (SEQ ID NO:57), FYKYK (SEQ ID NO:58), and FYESK (SEQ ID NO:59).

To identify potential acyl-donor and amine-donor substrates of the *K. albida* transglutaminase, high-throughput screening on 5-mer peptide arrays was performed (FIGS. 4A and 4B). An activity of at least 1.65 U/mg for both the SlyD-fused and the mature KalbTG enzymes was confirmed by commercial assay (Zedira MTG-ANiTA-KIT; compared to 4.3 U $mg^{-1}$ by the MTG supplied with the kit and a 0.07 U/mg blank value with BSA). The assay used β-casein as a cross-linking substrate and detected deamidation by a glutamate dehydrogenase dependent oxidation of NADPH. Specific recognition motifs were identified by assaying KalbTG with peptide arrays prepared by maskless array synthesis (U.S. Pat. Pub. No 2015/0185216 to Albert et al. filed on 19 Dec. 2014). The efficiency of the transamidation reaction between 1.4 million unique 5-mer peptides and a biotinylated amine donor was quantified on two arrays in parallel and the sequences of the peptides with the highest turnovers were determined (FIG. 4A). The nine best peptides were resynthesized and tested for KalbTG activity in a standalone GLDH-coupled assay. The results of the GLDH-coupled assay alongside the corresponding array data are shown in Table 1. Note that the array signal for the sequence MLAQG (SEQ ID NO:13) is marked not applicable (n. a.) as this sequence was not included on the array. Similarly, measurement of a background signal was only applicable to experiments performed on the array.

TABLE 1

| Sequence | SED ID NO | Array signal ($log_2$) | Reaction rate in solution (pmol/s) |
|---|---|---|---|
| YRYRQ | (SEQ ID NO: 1) | 8.99 | 3.52 ± 0.08 |
| RYRQR | (SEQ ID NO: 14) | 8.96 | 3.60 ± 0.12 |
| RYSQR | (SEQ ID NO: 15) | 8.93 | 3.22 ± 0.10 |
| FRQRQ | (SEQ ID NO: 16) | 8.93 | 3.07 ± 0.17 |
| RQRQR | (SEQ ID NO: 17) | 8.84 | 2.06 ± 0.08 |
| FRQRG | (SEQ ID NO: 18) | 8.82 | 2.11 ± 0.13 |
| QRQRQ | (SEQ ID NO: 19) | 8.77 | 2.98 ± 0.01 |
| YKYRQ | (SEQ ID NO: 20) | 8.70 | 4.00 ± 0.18 |
| QYRQR | (SEQ ID NO: 21) | 8.70 | 1.92 ± 0.07 |
| DYALQ | (SEQ ID NO: 22) | 7.22 | −0.05 ± 0.09 |
| MLAQG | (SEQ ID NO: 13) | n. a. | −0.11 ± 0.10 |
| Background | | 7.27 | n.a. |

KalbTG activity was obtained by measuring incorporation of a biotinylated amine-donor on the peptide array and rates of NADH oxidation at 340 nm and 37° C. in the presence of amine-donor substrate (500 µM) in the GLDH-coupled assay using 100 µM each of nine of the best-performing array-selected glutamine-containing substrates and of two S. mobaraensis MTG glutamine-containing substrates. Strong correlation between the top array-selected substrates and their performance in the GLDH-coupled assay was observed, whereas KalbTG exhibited no activity with preferred S. mobaraensis MTG substrates DYALQ (SEQ ID NO: 22) and MLAQG (SEQ ID NO: 13). Testing of the top sequences in Table 1 confirmed YRYRQ (SEQ ID NO: 1) and RYRQR (SEQ ID NO 14) as the top performing 5-mer substrates, with turnover rates of 3.52±0.08 pmol NADH $s^{-1}$ and 3.60±0.12 pmol NADH $s^{-1}$, respectively. Lysine-containing substrate YKYRQ (SEQ ID NO:20) exhibited the highest rates in the GLDH assay (4.00±0.18 pmol $s^{-1}$), which, without being limited by theory, may be an artifact caused by lysine cross-reactivity, and was thus omitted in further analysis. Surprisingly, no activity could be detected with the well-known S. mobaraensis MTG recognition motif MLAQGS (SEQ ID NO:23), represented by the 5-mer sequence MLAQG (SEQ ID NO: 13), or the S. mobaraensis MTG substrate DYALQ (SEQ ID NO:22).

A second round of maturation on the peptide array yielded APRYRQRAA (SEQ ID NO:24) as the top performing 9-mer substrate, which was then resynthesized as biotinylated peptide to act as acyl donor for the discovery of optimized lysine recognition motifs back on the 5-mer peptide array (FIG. 4B). Again, six of the best lysine-containing peptides were resynthesized and tested in the KalbTG in-solution activity assay using a peptide containing the optimized glutamine recognition sequence YRYRQ (SEQ ID NO:1) as an acyl donor (Table 2). It will be appreciated that calculation of an array signal for cadaverine was not applicable due to omission of cadaverine from the array.

TABLE 2

| Sequence | SEQ ID NO | Array Signal (log$_2$) | Reaction Rate in Solution (pmol $s^{-1}$) |
| --- | --- | --- | --- |
| RYSKY | (SEQ ID NO: 25) | 12.75 | 3.89 ± 0.04 |
| RYESK | (SEQ ID NO: 2) | 12.65 | 4.47 ± 0.16 |
| AYRTK | (SEQ ID NO: 26) | 12.57 | 3.65 ± 0.17 |
| RYRSK | (SEQ ID NO: 27) | 12.45 | 3.26 ± 0.10 |
| RYGKS | (SEQ ID NO: 28) | 12.38 | 2.66 ± 0.11 |
| YKGRG | (SEQ ID NO: 29) | 12.25 | 3.01 ± 0.09 |
| Cadaverine | n.a. | n.a. | 3.51 ± 0.12 |
| ARSKL | (SEQ ID NO: 30) | 12.0 | 3.87 ± 0.31 |

With reference to Table 2, KalbTG activity was obtained by measuring incorporation of a biotinylated glutamine-donor and rates of NADH oxidation at 340 nm and 37° C. in the presence of glutamine-donor substrate (200 µM) in the GLDH-coupled assay using 100 µM each of i) six of the top-performing array-selected lysine substrates, ii) cadaverine, and iii) preferred MTG lysine substrate ARSKL (SEQ ID NO:30). The highest turnover (4.47±0.16 pmol NADH $s^{-1}$) in the GLDH assay was observed with the sequence RYESK (SEQ ID NO:2). This is a small but significant increase over cadaverine (3.51±0.12 pmol $s^{-1}$) or ARSKL (SEQ ID NO:30) (3.87±0.31 pmol $s^{-1}$), a peptide previously established as a preferred MTG lysine donor motif on the peptide array. Additional details on the S. mobaraensis MTG substrate peptide ARSKL (SEQ ID NO:30) can be found in U.S. Provisional Patent Application Ser. No. 62/094,495 to Albert et al. filed on Dec. 19, 2014.

For construction of the peptide array, a library of 1,360,732 unique 5-mer peptides was designed by using all combinations of 18 natural amino acids excluding cysteine and methionine, as well as any dimer or a longer repeat of the same amino acid, and any peptide containing a dipeptide selected from HR, RH, HK, KH, RK, KR, HP, and PQ sequences. The library was synthesized in duplicate on the same array by using maskless light-directed peptide array synthesis. Each 5-mer peptide was flanked on both the N-terminus and C-terminus by 3 amino acid-long linkers synthesized by using mixture of glycine and serine having a 3:1 ratio.

To test KalbTG specificity for glutamine-containing substrate, N-(biotinyl)cadaverine was used as a substitute for a lysine substrate to biotinylate glutamine-peptides on a peptide array. KalbTG labeling reaction was performed in 1200 µL 100 mM Tris-HCl pH 8, 1 mM DTT, 50 µM N-(biotinyl)cadaverine, 0.2 ng µl$^{-1}$ KalbTG in SecureSeal™ chamber (Grace Bio-Labs) at 37° C. for 45 minutes. After incubation the chamber was removed and the array was washed in 20 mM Tris-HCl, pH7.8, 0.2 M NaCl, 1% SDS for 1 minute followed by a 1 minute wash in 20 mM Tris-HCl. Biotin linked to the array was stained with 0.3 µg ml$^{-1}$ Cy5-streptavidin in 10 mM Tris-HCl, pH7.4, 1% alkali-soluble casein, 0.05% TWEEN-20 non-ionic detergent at room temperature for 1 hour. Cy5 fluorescence intensity was measured with a fluorescence scanner at a resolution of 2 µm and a wavelength of 635 nm.

In order to test KalbTG specificity for lysine substrates, chemically synthesized Z-[APRYRQRAAGGG (SEQ ID NO:31)]-PEG-Biotin peptide—which includes the sequence APRYRQRAAGGG (SEQ ID NO:31)—was used as a glutamine-containing substrate to biotinylate lysine-containing peptides. Array biotinylation was done as described above with 0.1 ng µl$^{-1}$ KalbTG, 0.8 µM peptide at 37° C. for 15 minutes. Note that the a "Z—" in front of a peptide or other like construct is used herein to represent a carboxybenzyl group unless stated otherwise.

S. mobaraensis MTG reactions on peptide array were performed in 100 mM Tris-HCl, pH 8, 1 mM DTT with 10 µM N-(Biotinyl)cadaverine and 0.1 ng µl$^{-1}$ S. mobaraensis MTG at 37° C. for 15 minutes. As shown in FIG. 4A, the top 22 glutamine-donor substrates identified on the 5-mer peptide array with KalbTG were (in no particular order) FRQRG (SEQ ID NO:18), YRYRQ (SEQ ID NO:1), QRQRQ (SEQ ID NO:19), FRQRQ (SEQ ID NO:16), RYRQR (SEQ ID NO:14), RQRQR (SEQ ID NO:17), YRQSR (SEQ ID NO:32), YKYRQ (SEQ ID NO:20), LRYRQ (SEQ ID NO:33), YRQRA (SEQ ID NO:34), VRYRQ (SEQ ID NO:35), QRQTR (SEQ ID NO:36), YRQTR (SEQ ID NO:37), PRYRQ (SEQ ID NO:38), RFSQR (SEQ ID NO:39), WQRQR (SEQ ID NO:40), QYRQR (SEQ ID NO:21), VRQRQ (SEQ ID NO:41), RYTQR (SEQ ID NO:42), AYRQR (SEQ ID NO:43), YQRQR (SEQ ID NO:44), and RYSQR (SEQ ID NO:15). As shown in FIG. 4B, the top 17 lysine-donor substrates identified on the 5-mer peptide array with KalbTG were (in no particular order) NYRFK (SEQ ID NO:45), YQKWK (SEQ ID NO:46), YKYKY (SEQ ID NO:47), RWKFK (SEQ ID NO:48), RFYSK (SEQ ID NO:49), YKYAK (SEQ ID NO:50), YRYAK (SEQ ID NO:51), RYSYK (SEQ ID NO:52), YKSFK (SEQ ID NO:53), YKSWK (SEQ ID NO:54), KYRYK (SEQ ID NO:55), YKYNK (SEQ ID NO:56), RYSKY (SEQ ID NO:25), RYESK (SEQ ID NO:2), PYKYK (SEQ ID NO:57), FYKYK (SEQ ID NO:58), and FYESK (SEQ ID NO:59). The 16 glutamine-donor substrates identified with MTG and shown in FIGS. 5B and 5C were (in no particular order) EWVAQ (SEQ ID NO:60), EWALQ (SEQ ID NO:61), DYFLQ (SEQ ID NO:62), DYALQ (SEQ ID NO:22), EYWLQ (SEQ ID NO:63), DWALQ (SEQ ID NO:64), DWYLQ (SEQ ID NO:65), DYWLQ (SEQ ID NO:66), EYVAQ (SEQ ID NO:67), DYVAQ (SEQ ID NO:68), DWVAQ (SEQ ID NO:69), EYVLQ (SEQ ID NO:70), EWIAQ (SEQ ID NO:71), WYALQ (SEQ ID NO:72), EYALQ (SEQ ID NO:73), and EYFLQ (SEQ ID NO:74).

Example 4

Figure 5A:
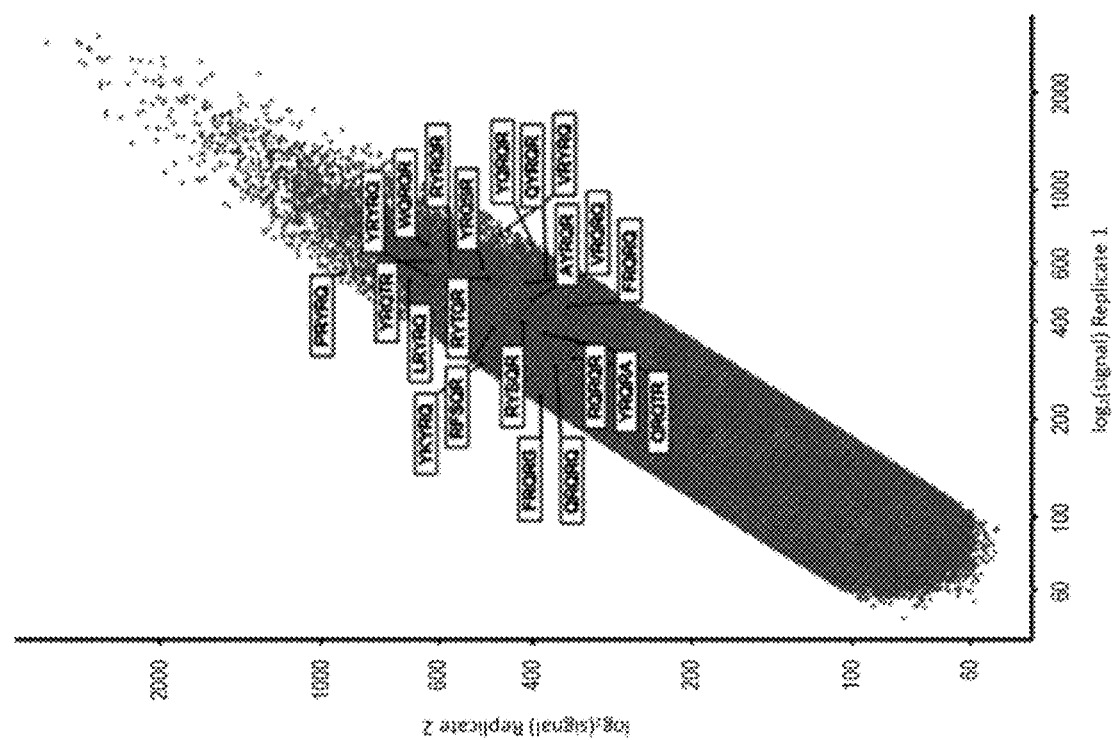
FIG. 5A is a log-log scatter plot showing the correlation between fluorescence signal data generated by S. mobaraensis MTG for replicate features on a 5-mer peptide array in the presence of biotinylated amine-donor substrate. Each data point represents a pair of replicate peptides from a library of 1.4 million unique peptides synthesized in duplicate. The 22 data points corresponding to the highest fluorescence signals generated by KalbTG from FIG. 4A are tagged by their respective 5-mer peptide sequence: YRYRQ (SEQ ID NO:1), RYRQR (SEQ ID NO:14), RYSQR (SEQ ID NO:15), FRQRQ (SEQ ID NO:16), RQRQR (SEQ ID NO:17), FRQRG (SEQ ID NO:18), QRQRQ (SEQ ID NO:19), YKYRQ (SEQ ID NO:20), QYRQR (SEQ ID NO:21), YRQSR (SEQ ID NO:32), LRYRQ (SEQ ID NO:33), YRQRA (SEQ ID NO:34), VRYRQ (SEQ ID NO:35), QRQTR (SEQ ID NO:36), YRQTR (SEQ ID NO:37), PRYRQ (SEQ ID NO:38), RFSQR (SEQ ID NO:39), WQRQR (SEQ ID NO:40), VRQRQ (SEQ ID NO:41), RYTQR (SEQ ID NO:42), AYRQR (SEQ ID NO:43), and YQRQR (SEQ ID NO:44).
Figure 5B:
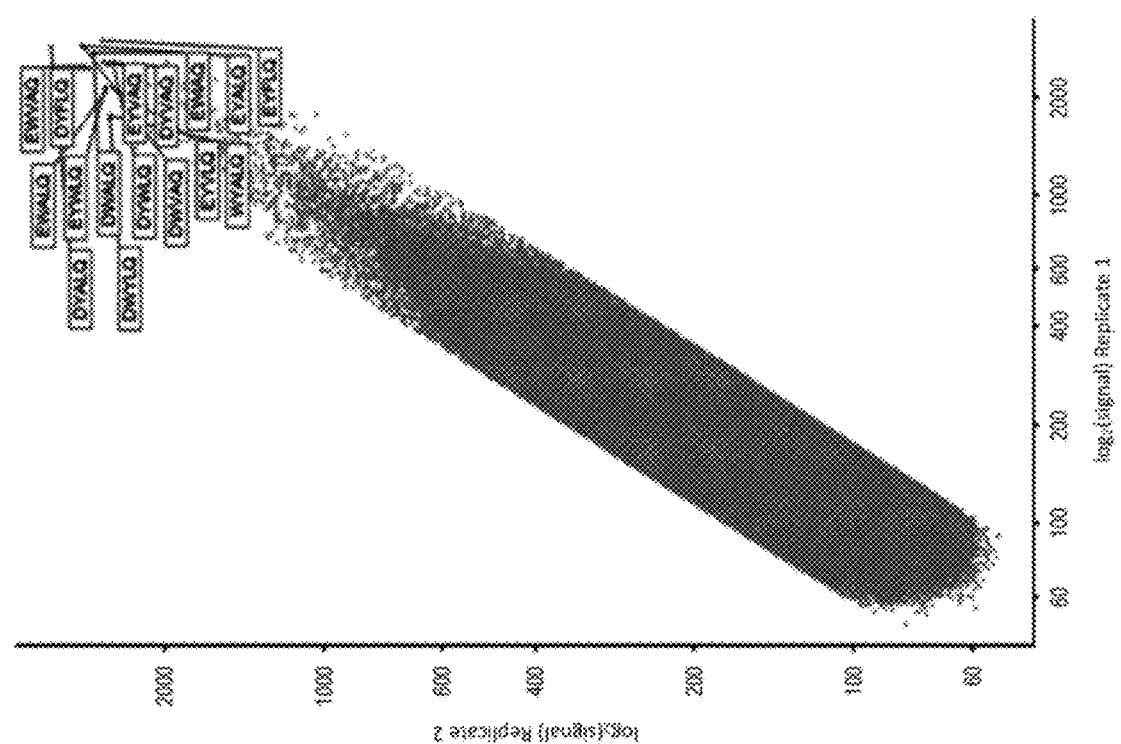
FIG. 5B is the plot of fluorescence signal data generated by S. mobaraensis MTG of FIG. 5A with the tagged data points from FIG. 4A omitted. The 16 data points corresponding to highest fluorescence signals generated by MTG are tagged by their respective 5-mer peptide sequence: DYALQ (SEQ ID NO:22), EWVAQ (SEQ ID NO:60), EWALQ (SEQ ID NO:61), DYFLQ (SEQ ID NO:62), EYWLQ (SEQ ID NO:63), DWALQ (SEQ ID NO:64), DWYLQ (SEQ ID NO:65), DYWLQ (SEQ ID NO:66), EYVAQ (SEQ ID NO:67), DYVAQ (SEQ ID NO:68), DWVAQ (SEQ ID NO:69), EYVLQ (SEQ ID NO:70), EWIAQ (SEQ ID NO:71), WYALQ (SEQ ID NO:72), EYALQ (SEQ ID NO:73), and EYFLQ (SEQ ID NO:74).
Figure 5C:
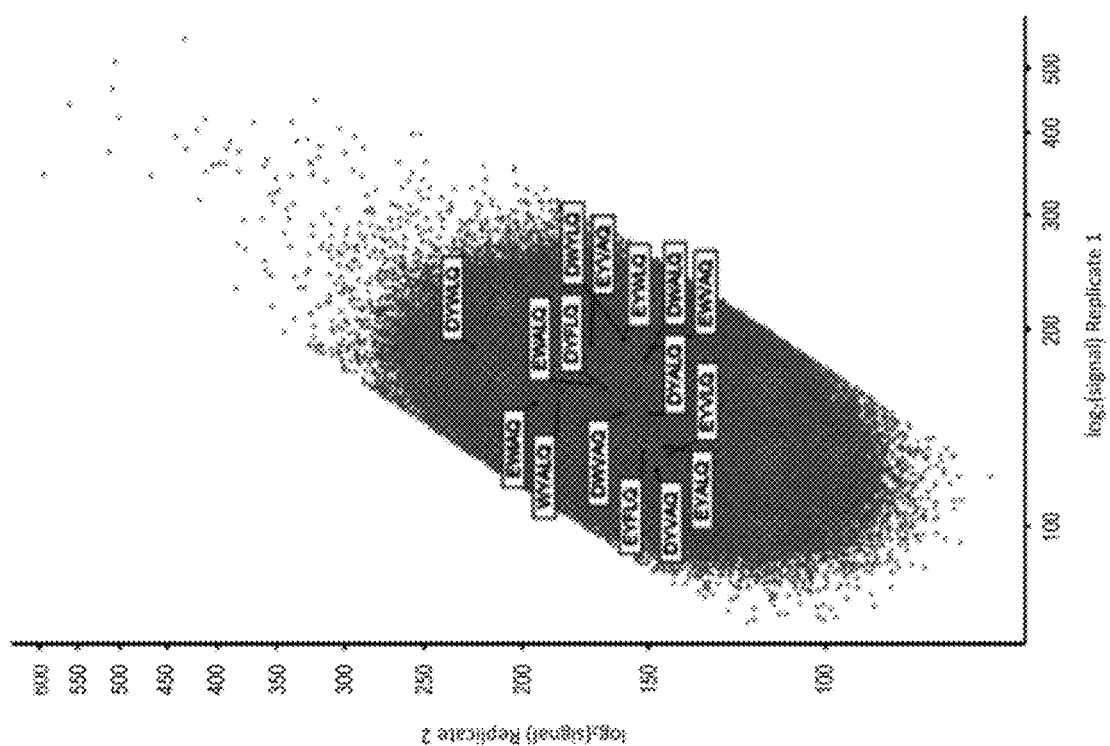
FIG. 5C is the plot of fluorescence signal data generated by KalbTG of FIG. 4A with the tagged data points from FIG. 4A omitted. The 16 data points corresponding to highest fluorescence signals generated by S. mobaraensis MTG from FIG. 5B are tagged by their respective 5-mer peptide sequence: DYALQ (SEQ ID NO:22), EWVAQ (SEQ ID NO:60), EWALQ (SEQ ID NO:61), DYFLQ (SEQ ID NO:62), EYWLQ (SEQ ID NO:63), DWALQ (SEQ ID NO:64), DWYLQ (SEQ ID NO:65), DYWLQ (SEQ ID NO:66), EYVAQ (SEQ ID NO:67), DYVAQ (SEQ ID NO:68), DWVAQ (SEQ ID NO:69), EYVLQ (SEQ ID NO:70), EWIAQ (SEQ ID NO:71), WYALQ (SEQ ID NO:72), EYALQ (SEQ ID NO:73), and EYFLQ (SEQ ID NO:74).
Figure 5D:
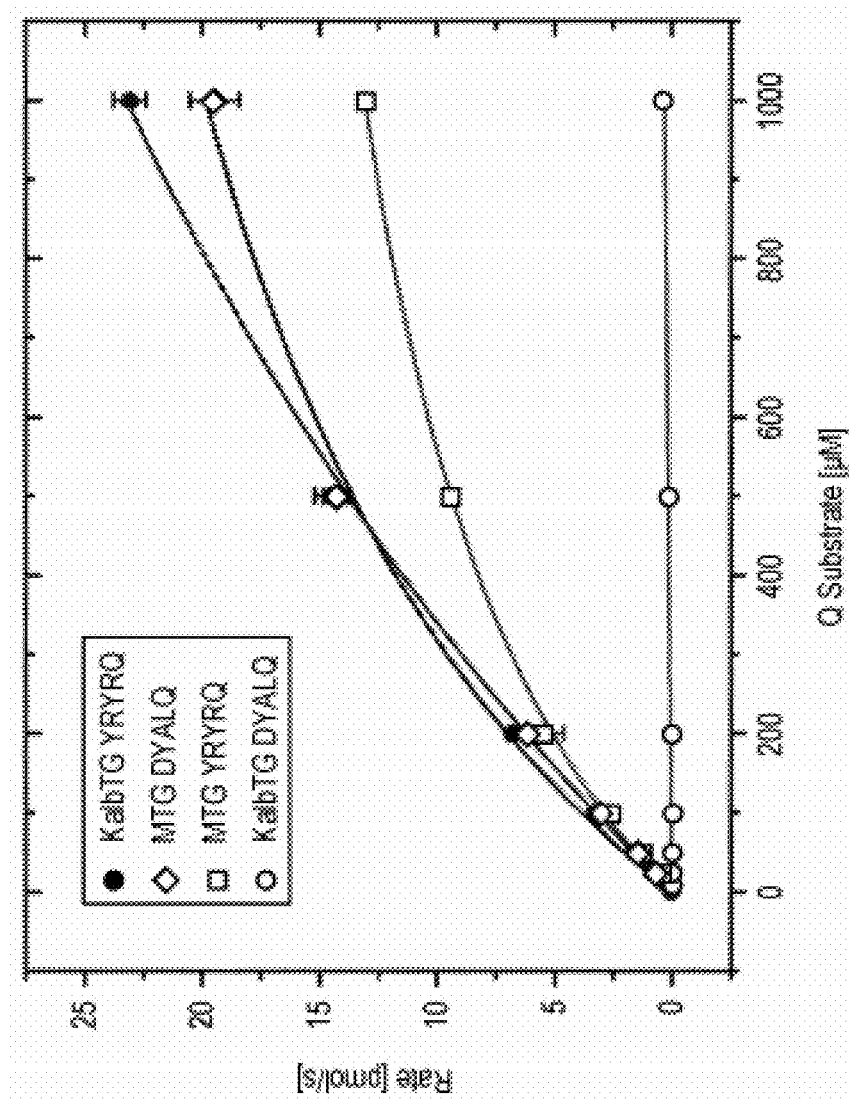
FIG. 5D is a plot of S. mobaraensis MTG and KalbTG activity obtained by measuring rates of NADH oxidation at 340 nm and 37° C. for varying concentrations of glutamine-donor substrates Z-GGGDYALQGGGG (SEQ ID NO:76) (0 to 1 mM) and Z-GGGYRYRQGGGG (SEQ ID NO:75) (0 to 1 mM) in the presence of amine-donor substrate cadaverine (1 mM) in a GLDH-coupled assay; YRYRQ (SEQ ID NO:1), DYALQ (SEQ ID NO:22).

Specificity of KalbTG for Maturated Glutamine Substrates and Application to Semi-Orthogonal Conjugation Since the peptide array can deliver readout about all viable 5-mer peptides at once, a single dataset each suffices to evaluate how enzymes differ in substrate specificity. The top KalbTG glutamine substrates (FIG. 4A) were found in the mid-field of the signal distribution on the array performed with MTG (FIG. 5A). By comparison, the top-performing S. mobaraensis MTG glutamine-containing substrates (FIG. 5B) exhibited relatively lower signal on the KalbTG array (FIG. 5C). To confirm that the two transglutaminase enzymes have orthogonal glutamine-containing substrate preferences and to quantify the amount of cross-reactivity, the kinetics of both enzymes were determined in the presence of varying concentrations of substrate peptides Z-[GGGYRYRQGGGG (SEQ ID NO:75)] and Z-[GGGDYALQGGGG (SEQ ID NO:76)] (FIG. 5D). Notably, the Z-conjugated substrates included the peptide sequences GGGYRYRQGGGG (SEQ ID NO:75) and GGGDYALQGGGG (SEQ ID NO:76). The S. mobaraensis MTG exhibited similar $K_M$ values in the 0.6-0.9 mM range for both substrates whereas turnover $k_{cat}$ was significantly higher with Z-[GGGDYALQGGGG (SEQ ID NO:76)] substrate including the preferred DYALQ (SEQ ID NO:22) sequence (1.39 s$^{-1}$ versus 0.93 s$^{-1}$ with YRYRQ (SEQ ID NO:1)), resulting in catalytic efficiencies ($k_{cat}\ K_M^{-1}$) of $1.64 \times 10^3$ [M$^{-1}$ s$^{-1}$] and $1.44 \times 10^3$ [M$^{-1}$ s$^{-1}$] respectively (Table 3). Compared to the engineered S. mobaraensis MTG enzyme, KalbTG appears to have a lower substrate binding efficiency ($K_M$ of 2 mM) but higher turnover ($k_{cat}$ of 1.92 s$^{-1}$), leading to $k_{cat}\ K_M^{-1}$ of $0.89 \times 10^3$ [M$^{-1}$ s$^{-1}$]. KalbTG appeared to be completely unreactive towards S. mobaraensis MTG substrate Z-[GGGDYALQGGGG (SEQ ID NO:76)], thus kinetic parameters could not be determined as indicated by 'n. d.' in Table 3.

TABLE 3

| Property | Value | | | |
|---|---|---|---|---|
| Enzyme | MTG | MTG | KalbTG | KalbTG |
| Substrate | DYALQ (SEQ ID NO: 22) | YRYRQ (SEQ ID NO: 1) | DYALQ (SEQ ID NO: 22) | YRYRQ (SEQ ID NO: 1) |
| $V_{max}$ [pmol/s] | 36.66 ± 3.33 | 21.50 ± 1.00 | n.d. | 73.18 ± 7.27 |
| $K_M$ [μM] | 846.96 ± 137.75 | 643.63 ± 58.38 | n.d. | 2151.09 ± 290.94 |
| $k_{cat}$ [S$^{-1}$] | 1.39 | 0.93 | n.d. | 1.92 |
| $k_{cat}/K_M$ [M$^{-1}$s$^{-1}$] | $1.64 \times 10^3$ | $1.44 \times 10^3$ | n.d. | $0.89 \times 10^3$ |

Figure 6A:
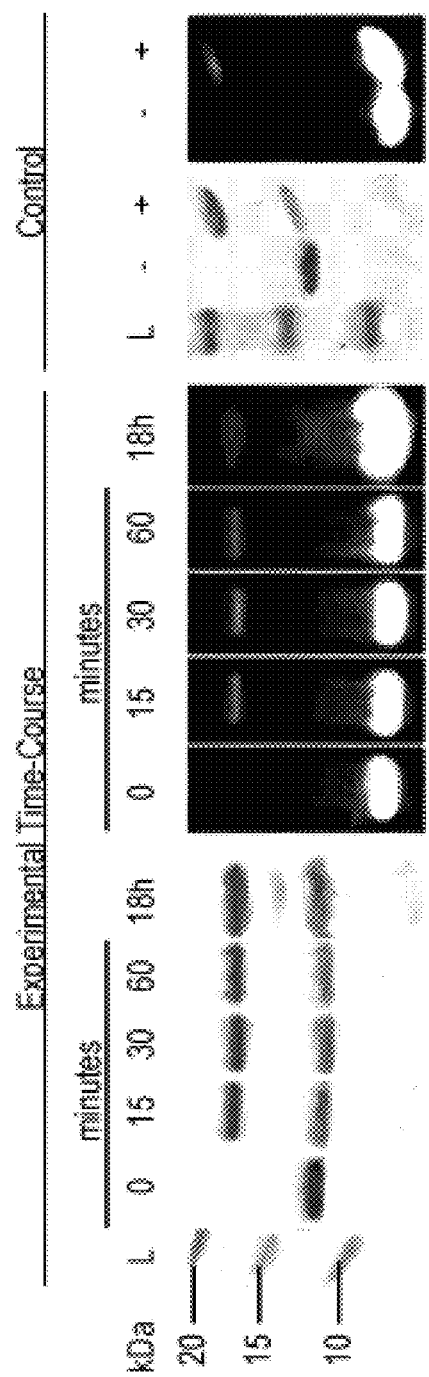
FIG. 6A is a series of images of SDS-PAGE gels showing both an experimental time-course (Left: bright field; Right: Cy3 fluorescence) and control data (Left: bright field; Right: Cy3 fluorescence) for Cy3 labeling of a Q-tagged *Thermus thermophilus* SlyD moiety. Successful mono-labeling is observed by the shift in electrophoretic mobility corresponding to the 6 kDa molecular weight of the label and by the fluorescent signal of the labeled species. Data is shown for a 60 minute time-course performed with 10-fold label excess, and for an 18 hour incubation with 50-fold label excess. Lanes labeled 'L' were loaded with a standard molecular weight ladder (values shown in kDa). Lanes labeled '−' and '+' denote control reactions with SlyD containing the S. mobaraensis MTG Q-tag (DYALQ (SEQ ID NO: 22)) and KalbTG (−) or S. mobaraensis MTG (+).
Figure 6B:
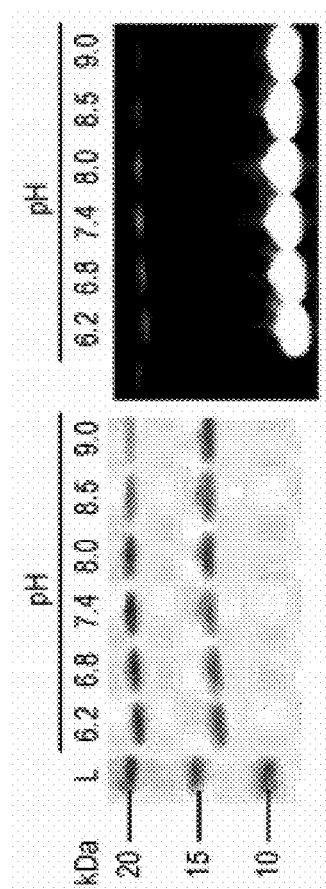
FIG. 6B is a series of images of an SDS-PAGE gel showing a pH profile of KalbTG labeling efficacy for pH values between 6.2 and 9.0 (Left: bright field; Right: Cy3 fluorescence). The highest labeling yield after the 15 minute reaction time was observed at pH 7.4. The lane labeled 'L' was loaded with a standard molecular weight ladder (values shown in kDa).

Next, the array and in-solution data were applied to perform site-specific labeling on protein substrates. The molecular chaperone SlyD is a useful scaffold for labeling approaches as epitope-containing loops can be grafted onto the FKBP domain for presentation to binders or enzymes (PCT App. Pub. No. WO 2012/150321 A1 to Andres et al.). A chimeric protein consisting of the Thermus thermophilus FKBP domain and the KalbTG recognition sequence RYRQR (SEQ ID NO:14) was produced. Labeling with a ten-fold excess of KalbTG K-tag-Cy3 and a substrate to enzyme ratio of 72:1 afforded approximately 70% yield of a labeled protein species after 15 minutes (FIG. 6A). This yield remained constant over a time-course of 60 minutes. Incubation with a 50-fold label excess only slightly increased the yield of the labeled species. The molecular weight shift from 13 kDa to 19 kDa was observed on the SDS-PAGE gel, corresponding exactly to the incorporation of a single 6 kDa label molecule. An identically constructed FKBP domain, containing the S. mobaraensis MTG sequence DYALQ (SEQ ID NO:22) instead of RYRQR (SEQ ID NO:14), showed no incorporation of label when incubated with KalbTG (FIG. 6A), signifying that the reaction is limited to the site of the KalbTG recognition motif and that none of the 5 other glutamines intrinsic to the FKBP domain are recognized. We furthermore assayed the pH dependency of the labeling reaction at pH 6.2, 6.8, 7.4, 8.0, 8.5, and 9 (FIG. 6B). The highest labeling efficiency after 15 minutes was found at pH 7.4, with activity trailing off at pH 8.5 and above. These findings correspond well with the published pH preferences of S. mobaraensis MTG.

Figure 6C:
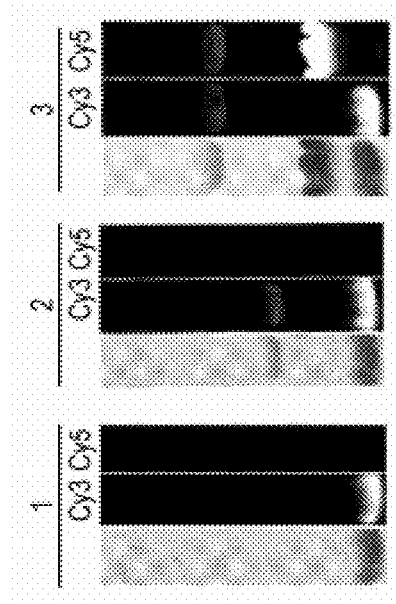
FIG. 6C is a series of images of SDS-PAGE gels showing dual site-specific functionalization of the construct YRYRQ-PEG27-(factor Xa cleavage site)-PEG27-PEG27-DYALQ with Cy3 and Cy5 fluorescent labels. Each group (labeled 1, 2, and 3) includes three images of the same gel lane arranged in the following order from left to a right: i) bright field; ii) Cy3 fluorescence; and iii) Cy5 fluorescence. Group 1: A mixture of peptide construct and 10-fold excess of Cy3 label. Group 2: A mixture of peptide construct and 10-fold excess of Cy3 label following incubation with KalbTG enzyme for 30 min. Group 3: S. mobaraensis MTG enzyme and Cy5 label added to the composition of Group 2, and incubated for 15 min with no intermediate blocking or purification steps; dually labeled construct was achieved with nearly quantitative yield.

Turning to FIG. 6C, the high sequence specificity of KalbTG was used to conjugate a 6 kDa Cy3 label to the YRYRQ (SEQ ID NO:1) site of a 7 kDa substrate peptide comprising both the KalbTG and S. mobaraensis MTG glutamine-containing motifs. The reaction was run for 30 minutes to saturate the YRYRQ (SEQ ID NO:1) site. Analysis by SDS-PAGE confirmed that the label was integrated at a single site. The substrate peptide was subsequently incubated for 15 minutes with S. mobaraensis MTG and a 6 kDa Cy5 label. This resulted in the formation of a site-specifically dual-labeled conjugate, with all single-labeled species having visibly been converted to the dual-labeled species. These results confirm that KalbTG and S. mobaraensis MTG constitute a semi-orthogonal labeling system with unparalleled ease of use, yield, and efficiency. Accordingly, KalbTG may be useful for the industrial-scale synthesis of complex protein conjugates of interest in therapeutic or diagnostic applications.

For the GLDH coupled assay, to determine whether the KalbTG peptides selected in the array assay were also preferred substrates in a solution reaction and to quantify cross-reactivity of KalbTG and S. mobaraensis MTG with various substrates, a continuous glutamate dehydrogenase (GLDH)-coupled assay for *S. mobaraensis* MTG activity (see Oteng-Pabi, et al., 2013. Analytical biochemistry 441 (2): 169-173) was applied.

For glutamine substrate evaluation, the assay was performed in a transparent 96-well microtiter plate in the presence of 500 µM α-ketoglutarate, 500 µM or 1 mM cadaverine as Amine donor substituting for a lysine-containing peptide, 2 U ml$^{-1}$ of glutamate dehydrogenase (GLDH), 500 µM NADH and glutamine-containing substrate peptide (Z-[GGGQRWRQGGGG (SEQ ID NO:77)], Z-[GGGWRYRQGGGG (SEQ ID NO:78)], Z-[GGGY-RYRQGGGG (SEQ ID NO:75)], Z-[GGGRYRQGGGG (SEQ ID NO:79)], Z-[GGGRYSQRGGGG (SEQ ID NO:80)], Z-[GGGFRQRQGGGG (SEQ ID NO:81)], Z-[GGGRQRQRGGGG (SEQ ID NO:82)], Z-[GGG-FRQRGGGGG (SEQ ID NO:83)], Z-[GGGQRQRQGGGG (SEQ ID NO:84)], Z-[GGGYKYRQGGGG (SEQ ID NO:85)], Z-[GGGQYRQRGGGG (SEQ ID NO:86)], Z-[GGGDYALQGGGG (SEQ ID NO:76)] or Z-[GGGM-LAQGSGGG (SEQ ID NO:87)]) concentrations ranging between 0 and 1 mM in 200 mM MOPS, 1 mM EDTA pH 7.2 (total volume per well 200 µl). Notably, the Z-conjugated peptides included the sequences GGGQRWRQGGGG (SEQ ID NO:77), GGGWRYRQGGGG (SEQ ID NO:78), GG-GYRYRQGGGG (SEQ ID NO:75), GGGRYRQRGGGG (SEQ ID NO:79), GGGRYSQRGGGG (SEQ ID NO:80), GGGFRQRQGGGG (SEQ ID NO:81), GGGRQ-RQRGGGG (SEQ ID NO:82), GGGFRQRGGGGG (SEQ ID NO:83), GGGQRQRQGGGG (SEQ ID NO:84), GG-GYKYRQGGGG (SEQ ID NO:85), GGGQYRQRGGGG (SEQ ID NO:86), GGGDYALQGGGG (SEQ ID NO:76), and GGGMLAQGSGGG (SEQ ID NO:87).

For amine substrate evaluation, assay conditions were the same as for glutamine substrate evaluation with the exception that 100 µM each of amine substrate (Z-[GGGRYSKY-GGGG (SEQ ID NO:88)], Z-[GGGAYRTKGGGG (SEQ ID NO:89)], Z-[GGGRYRSKGGGG (SEQ ID NO:90)], Z-[GGGYKGRGGGGG (SEQ ID NO:91)], Z-[GGGR-YGKSGGGG (SEQ ID NO:92)], Z-[GGGRYESKGGGG (SEQ ID NO:93)], Z-[GGGPGRYKGGGG (SEQ ID NO:94)], Z-[GGGARSKLGGGG (SEQ ID NO:95)] or cadaverine) and 200 µM glutamine donor (Z-[GG-GYRYRQGGGG (SEQ ID NO:75)] or Z-[GGGDY-ALQGGGG (SEQ ID NO:76)]) were used. Notably, the amine substrates included the sequences GGGRYSKY-GGGG (SEQ ID NO:88), GGGAYRTKGGGG (SEQ ID NO:89), GGGRYRSKGGGG (SEQ ID NO:90), GGG-YKGRGGGGG (SEQ ID NO:91), GGGRYGKSGGGG (SEQ ID NO:92), GGGRYESKGGGG (SEQ ID NO:93), GGGPGRYKGGGG (SEQ ID NO:94), and GGGARSK-LGGGG (SEQ ID NO:95).

Reactions were started by the addition of 5 µg ml$^{-1}$ of *S. mobaraensis* MTG or KalbTG and the oxidation of NADH was continuously recorded at 340 nm for 60 minutes using a Biotek Synergy H4 microplate reader, temperature controlled at 37° C., with short shaking intervals before each measurement. After a short lag phase where the GLDH was saturated by transglutaminase-mediated release of ammonia, linear rates of absorbance versus time corresponding to transglutaminase turnover were observed and subjected to Michaelis-Menten kinetic analysis. Rates of absorbance in millioptical density units per minute (mOD min$^{-1}$) were converted into molar rates of NADH turnover (pmol s$^{-1}$) using the formula of Equation 1 (previously determined by an NADH standard curve):

Turnover rate=|Absorbance rate|*1.111 (Eq. 1)

For the labeling assays, the chaperone SlyD from *Thermus thermophilus* (Universal Protein Resource (UniProt) Number Q5SLE7) was used as a labeling scaffold for KalbTG. The SlyD sequence is:

```
                                     (SEQ ID NO: 96)
MKVGQDKVVTIRYTLQVEGEVLDQGELSYLHGHRNLIPGLEEALEGREEG

EAFQAHVPAEKAYGPHDPEGVQVVPLSAFPEDAEVVPGAQFYAQDMEGNP

MPLTVVAVEGEEVTVDFNHPLAGKDLDFQVEVVKVREATPEELLHGHAH
```

A KalbTG glutamine donor sequence (Q-tag) was recombinantly grafted onto the FKBP domain of SlyD, yielding the following polypeptide sequence:

```
                                     (SEQ ID NO: 97)
MKVGQDKVVTIRYTLQVEGEVLDQGELSYLHGHRNLIPGLEEALEGREEG

EAFQAHVPAEKAYGAGSGGGGRYRQRGGGGGSSGKDLDFQVEVVKVREAT

PEELLHGHAHHHHHHHH
```

The 8×-histidine-tagged protein was produced in *E. coli* Bl21 Tuner and purified by standard Ni SEPHAROSE chromatography media-based immobilized metal ion affinity and size exclusion chromatography (HISTRAP chromatography column, SUPERDEX 200 size exclusion media; GE Healthcare).

Labeled peptides were chemically synthesized to have (in order from N-terminus to C-terminus) a "Z-" group (i.e., a carboxybenzyl group), a transglutaminase lysine donor sequence (K-tag), 8-amino-3,6-dioxaoctanoic acid (O2Oc), peptide, and a Cy3 or Cy5 fluorescent dye. The primary chemical structures of the labeled peptides were:

```
KalbTG K-tag-Cy3:
Z-[RYESKG (SEQ ID NO: 98)]-O2Oc-
[EUEUEUEUEUEUEUEUEUEUEUEUEUEUEUEUEUEUEU (SEQ ID
NO: 99)]-C(sCy3-MH)-OH (5863.9 g/mol),
and MTG K-tag-Cy5:
Z-[RSKLG (SEQ ID NO: 100)]-O2Oc-
[EUEUEUEUEUEUEUEUEUEUEUEUEUEUEUEUEUEUEU (SEQ ID
NO: 99)]-C(Cy5-MH)-OH (5723.9 g/mol),
``` where E is glutamate, U is β-alanine, and C(sCy3-MH) and C(Cy5-MH) stand for a C-terminal cysteine modified post-synthetically by sulfo-Cy3 maleimide or Cy5 maleimide, respectively.

For the orthogonal labeling experiment, a molecule containing both KalbTG and MTG Q-tags was chemically synthesized to have the primary chemical structure:

```
Z-[GGGYRYRQGGG (SEQ ID NO: 101)]-PEG27-[GIEGRG
(SEQ ID NO: 102)]-PEG27-PEG27-[GGGDYALQGG (SEQ ID
NO: 103)]-OH (6620.6 g/mol).
```

All peptides were synthesized via standard Fluorenylmethyloxycarbonyl (FMOC)-based solid phase peptide synthesis in a 0.25 mmol scale using commercially available building blocks. After solid phase synthesis, peptides were cleaved with a solution of 95% TFA, 2.5% triisopropylsilane, and 2.5% water. Peptides were then precipitated with diisopropylether and purified via reverse phase C18-based high performance liquid chromatography (RP18-HPLC) using a water/TFA acetonitrile gradient. Dye labeling was achieved by reaction of the peptides with sulfo-Cy3 maleimide (Lumiprobe) and Cy5 maleimide (GE Healthcare), respectively. Purification of dye labeled peptides was achieved by RP18-HPLC using a water/TFA acetonitrile gradient. Identity of peptides was confirmed by liquid chromatography—mass spectrometry (LC-MS) (Thermo Scientific RSLC-MSQplus system) applying a Kinetex C18 2.6 µm, 50×3 mm column (Phenomenex).

If not noted otherwise, labeling reactions were performed for 15 minutes at 37° C. in the presence of 72 µM substrate protein, 720 µM label peptide and 1 µM transglutaminase in 200 mM MOPS pH 7.2 and 1 mM EDTA. For the pH-dependent labeling profile, experiments were performed in 200 mM MOPS for each of pH 6.2, 6.8, and 7.4, or in 200 mM Tris for each of pH 8.0, 8.5, and 9.0. For the orthogonal labeling experiment, 1.5 µM EcSlyD2-Xa-KalbTGt3-8×His was added to a volume of 20 µl containing 100 µM substrate peptide and 1 mM KalbTG K-tag-Cy3. After incubation for 30 minutes at 37° C., 1 mM MTG K-tag-Cy5, and 1.5 µM S. mobaraensis MTG were added and incubated for an additional 15 minutes at 37° C. The reaction was stopped by the addition of 50 mM TCA. Samples were taken between incubation steps and analyzed by SDS-PAGE, in-gel fluorescence (BioRad ChemiDoc gel documentation system, Cy3 and Cy5 LED and filter sets). In a further orthogonal labeling experiment, 4.65 µM EcSlyD2-Xa-KalbTGt3-8×His was added to a volume of 50 µl containing 302 µM substrate peptide and 3.02 mM KalbTG K-tag-Cy3 (i.e., Cy3 labeled lysine substrate for KalbTG). After incubation for 30 minutes at 37° C., mixture was diluted by addition of 400 µl buffer, and subsequently concentrated to 50 µl (10 kDa molecular weight cutoff spin filter). Next, 3.02 mM MTG K-tag-Cy5 (i.e., Cy5 labeled lysine substrate for S. mobaraensis MTG) and 4.65 µM S. mobaraensis MTG were added and incubated for an additional 15 minutes at 37° C. The reaction was stopped by the addition of 50 µM $(NH_4)_2SO_4$. Then, 2 µg of factor Xa was added and the mixture incubated for 2 hours at room temperature. The reaction was stopped by the addition of 50 mM TCA. The mixture was filtered (0.2 µm spin filter) and analyzed by LC-MS with UV detection at 214 nm and 305 nm.

A further experiment was performed to determine the activity of KalbTG enzymes prepared from two different constructs, and stored at two different temperatures. The KalbTGt3 (SEQ ID NO:10) and KalbTGt1 (SEQ ID NO:12) enzymes tested were obtained respectively from the EcSlyD2-Xa-KalbTGt3-8×His-tag construct (SEQ ID NO:8) and the EcSlyD2-Xa-KalbTGt1-8×His-tag construct (SEQ ID NO:11) described in Example 3. The activity of the two KalbTG enzymes was tested after storage at either 4° C. or −20° C. and compared against the activity of commercially available S. mobaraensis MTG according to a published protocol (Oteng-Pabi, et al., 2013. Analytical biochemistry 441(2): 169-173). In particular, assays were performed at 37° C. in 200 µl total volume. The assay mixture included 200 mM MOPS, 1 mM EDTA, and 1 mM DTT at pH 7.4. Further, α-ketoglutarate and NADH were added at a concentration of 500 µM, along with 2 U/ml GLDH, and between 0.1 µg and 1.0 µg of one of the transglutaminase enzymes. The glutamine substrate was 200 µM Z-[GGGYRYRQGGGG (SEQ ID NO:75)]-OH, and the amine donor was 10 mM cadaverine, where Z represents a carboxybenzyl group. All data were collected in triplicate (average of 3 wells in a microtiter plate) and baseline activity (buffer without enzyme) subtracted. The resulting data is shown in Table 4.

TABLE 4

| Enzyme | Storage (° C.) | Activity (µmol NH3/min/mg Enzyme) |
|---|---|---|
| S. mobaraensis MTG | −20 | 1.1348 ± 0.0059 |
| KalbTGt3 (SEQ ID NO: 10) | 4 | 0.1501 ± 0.0011 |
| KalbTGt3 (SEQ ID NO: 10) | −20 | 0.1528 ± 0.0400 |
| KalbTGt1 (SEQ ID NO: 12) | 4 | 1.4099 ± 0.1806 |
| KalbTGt1 (SEQ ID NO: 12) | −20 | 0.8630 ± 0.0259 |

Example 5

Identification and Characterization of the 3D Crystal Structure of KalbTG

Figure 7A:
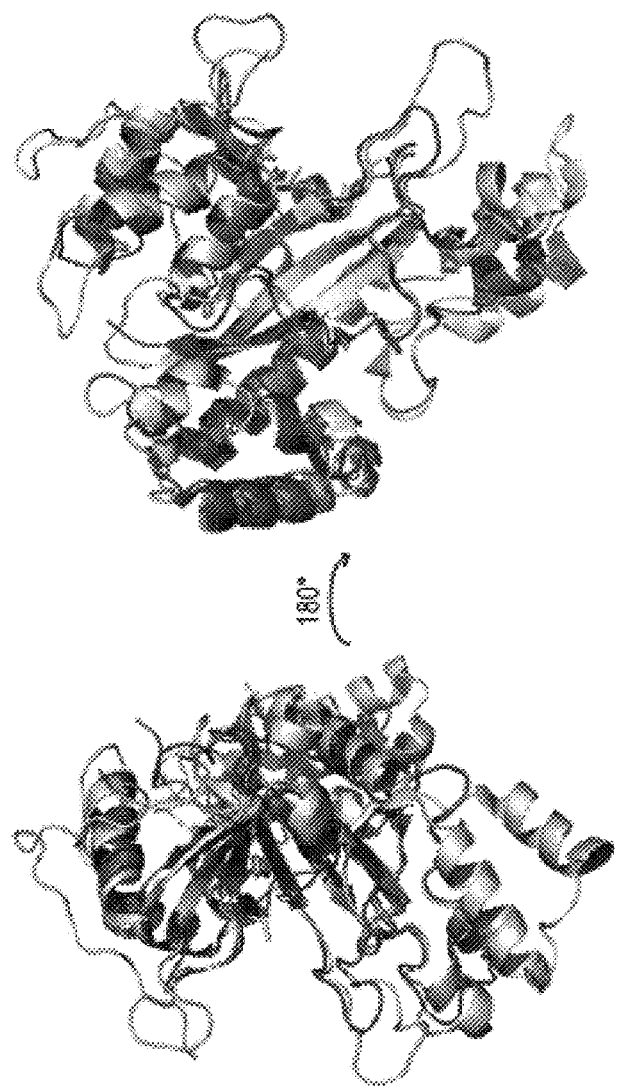
FIG. 7A is a three-dimensional alignment of the active enzyme structures of KalbTG (dark grey) and S. mobaraensis MTG (light grey) that reveals high conservation in the core and active site region and high variability in the peripheral loop regions.
Figure 7C:
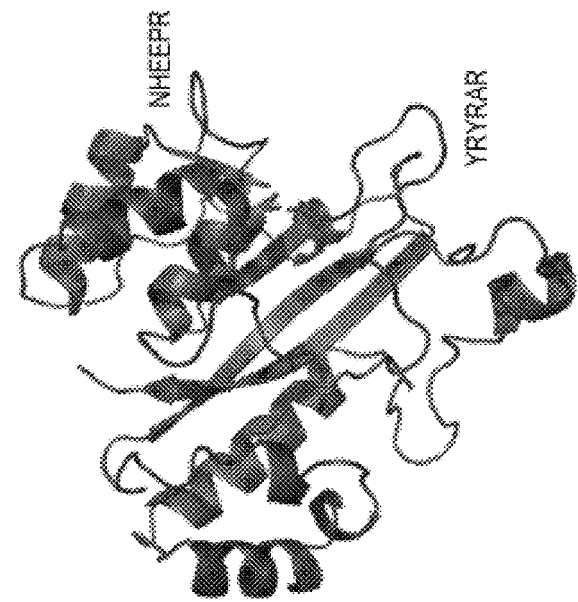
FIG. 7C is a three-dimensional ribbon structure illustrating contributors to the formation of the KalbTG active cleft including two strongly charged, hydrophilic loops that are believed to either mediate substrate recruitment, act as a substrate mimic, or a combination thereof. The two hydrophilic loops are labeled with their corresponding sequences (i.e., NHEEPR (SEQ ID NO:3) and YRYRAR (SEQ ID NO:4)).
Figure 7B:
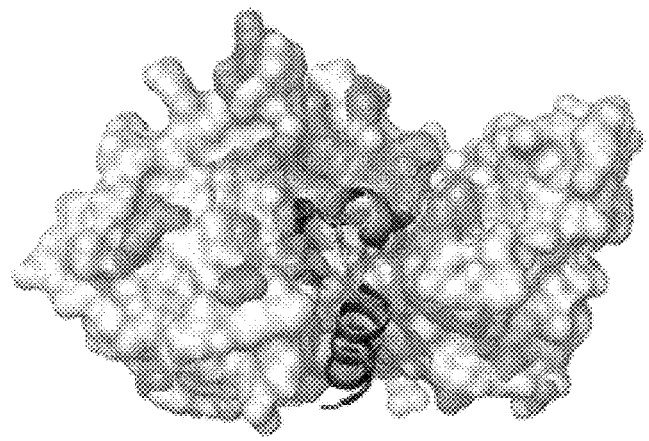
FIG. 7B is a three-dimensional surface overlay of the active enzyme structures of KalbTG (dark grey) and S. mobaraensis MTG (light grey) illustrating that the binding pocket of both S. mobaraensis MTG and the more compact KalbTG may be similarly occupied by a propeptide (ribbon structure).

As shown in FIGS. 7A-7C, alignment of the full structure of the MTG from K. albida with the MTG from S. mobaraensis provided insight into the nature of the KalbTG. In one aspect, the first nineteen N-terminal amino acids and the C-terminal artificial GGGSG-8×-His tag are disordered and were therefore not resolved in the structure. The overall structure of KalbTG resembles the S. mobaraensis MTG structure as described previously (Kashiwagi, et al. 2002. J. Bio. Chem. 277(46): 44252-44260), forming a disc-like shape of the α+β folding class, with two multi-loop protrusions forming the active site cleft. However, the structures differ in two α-helices (α4 and as in Kashiwagi's numbering) which are not present in the KalbTG structure, and two small β-strands ($\beta_2$ and $\beta_4$) which comprise less hydrophobic residues in the KalbTG (SF instead of AF, and QV instead of LV, respectively), bringing the total elements in KalbTG to only nine α-helices and six β-strands. The catalytic triad (Cys64, Asp255, His274) is structurally conserved (Cys82, Asp211, His224 numbering from the beginning of the KalbTG open reading frame). However the thiol side chain of KalbTG Cys82 is embedded 2.6 Å deeper in the active cleft than its S. mobaraensis MTG counterpart. The crystal structure of the S. mobaraensis MTG zymogen (Yang, et al. 2011. J. Bio. Chem. 286(9): 7301-7307) shows the active cleft being tightly occupied by the L-shaped propeptide. The binding pocket of KalbTG can be aligned with the propeptide of S. mobaraensis MTG without steric hindrance, indicating that a similar zymogenic mechanism may be present in the KalbTG (FIG. 7B). Amazingly, one of the loops forming the active cleft near Cys82 presents the amino acid sequence YRYRAR (SEQ ID NO:4), which is, but for the glutamine side chain, identical to the preferred KalbTG substrate discovered on the peptide array (i.e., the top two 5-mer peptides were YRYRQ (SEQ ID NO:1) and RYRQR (SEQ ID NO:14); FIG. 7C). Accordingly, analysis of the crystal structure served as an independent confirmation of the reliability of the peptide arrays with respect to the identification of substrate sequences.

For crystallization and structural characterization of KalbTG, KalbTG in PBS was crystallized at 22° C. using the sitting drop (200 nL) vapor diffusion method by 1:1 mixing of 8 mg/mL protein with un-buffered reservoir consisting of 0.2 M ammonium tartrate, 20% PEG 3350. Crystals were cryo-protected in reservoir solution containing 20% ethylene glycol before flash-cooling in liquid nitrogen. Data were collected at 100 K at SLS beamline PX-II using a Pilatus 6M detector and integrated and scaled in space group P3 with XDS (PMID 20124692). The I=3n reflections have I/σ of >9, rendering the presence of a screw axis unlikely. Self-Patterson and twinning analyses did not reveal suspicious data pathologies. The cell volume is consistent with two or three KalbTG molecules in the asymmetric unit with Matthews parameters of 3.5 Å³/Da and 2.3 Å³/Da, respectively. Data collection statistics are summarized in Table 5.

The structure of KalbTG (226 residues) was determined by molecular replacement using the *S. mobaraensis* transglutaminase (354 residues, RCSB Protein Data Band (PDB) ID No. 3iu0) as the search model. First attempts using the complete *S. mobaraensis* TG were generally unsuccessful as, without being limited by theory, the enzymes are of very different sizes. The two transglutaminases share 28.2% sequence identity and 38.9% sequence similarity over the entire length of KalbTG. A variant of *S. mobaraensis* TG devoid of loop regions and trimmed to the hydrophobic core resulted in a potential solution with the Phaser crystallographic software (McCoy et al., 2007. *J. Appl. Crystallogr.* August 1; 40 (Pt 4): 658-674) when searching for two molecules in the asymmetric unit in space group P3 with a log-likelihood gain (LLG) of 213. Trigonal space groups $P3_1$ and $P3_2$ did not yield solutions, consistent with the high intensities of the I=3n reflections. The model was refined with the BUSTER crystallographic software (Blanc et al., 2004. *Acta Cryst.* D60, 2210-2221) to an $R_{free}$ of 46%. Some secondary structure elements were visible in the electron density maps and included in the model, which was then submitted to ten cycles of automatic model building and refinement in CBUCCANEER and REFMAC5 (Winn et al., 2011. *Acta Cryst.* D67, 235-242). The resulting model contained all protein residues and had an $R_{free}$ of 30%. The structure was completed in COOT (Emsley et al., 2010. *Acta Cryst.* D66, 486-501) and refined with PHENIX (Adams et al., 2010. *Acta Cryst.* D66, 213-221). Model refinement statistics are collected in Table 5.

TABLE 5

| Data Statistics | |
|---|---|
| Wavelength (Å) | 1.0 |
| Resolution range (Å) | 38.69-1.98 (2.051-1.98) |
| Space group | P3 |
| Unit cell (Å, °) | A = 106.9 c = 56.1 |
| Total reflections | 244642 (23235) |
| Unique reflections | 49846 (4993) |
| Multiplicity | 4.9 (4.7) |

TABLE 5-continued

| | |
|---|---|
| Completeness (%) | 1.00 (1.00) |
| Mean I/σ (I) | 7.41 (1.10) |
| Wilson B-factor (Å²) | 29.12 |
| R-merge | 0.1793 (1.484) |
| R-meas | 0.2013 (1.679) |
| CC1/2 | 0.993 (0.327) |
| CC* | 0.998 (0.702) |
| $<I^2>/<I>^2$ | 2.0 |
| $<|E^2 - 1|>$ | 0.731 |
| Model Refinement | |
| Reflections used in refinement | 49846 (4984) |
| Reflections used for R-free | 2419 (318) |
| R-work | 0.1827 (0.3131) |
| R-free | 0.2296 (0.3498) |
| CC(work) | 0.967 (0.612) |
| CC(free) | 0.941 (0.575) |
| Number of non-hydrogen atoms | 4262 |
| Macromolecules | 3765 |
| Ligands | 75 |
| Protein residues | 450 |
| RMS(bonds) (Å) | 0.007 |
| RMS(angles) (°) | 1.08 |
| Ramachandran favoured (%) | 99 |
| Ramachandran allowed (%) | 1.3 |
| Ramachandran outliers (%) | 0 |
| Rotamer outliers (%) | 0.5 |
| Clashscore | 2.94 |
| Average B-factor (Å²) | 33.35 |
| Macromolecules | 32.42 |
| Ligands | 51.75 |
| Solvent | 38.41 |

With reference to Table 5, statistics for the highest-resolution shell are shown in parentheses.

Dynamic scanning calorimetry (DSC) measurements were performed in the temperature range 20° C. to 90° C. on a VP-Capillary DSC instrument (MicroCal/GE Healthcare) and a scanning rate of 90° C. h⁻¹, using PBS as reference.

Example 6

Analysis of Identified KalbTG Peptide Substrates Characteristics

With reference to Tables 6 and 7, analysis of the KalbTG peptide substrates identified herein revealed a set of characteristics shared by those substrates.

TABLE 6

| | amino acid position | | | | | amino acid count | | | | |
|---|---|---|---|---|---|---|---|---|---|---|
| SEQ ID NO: | 1 | 2 | 3 | 4 | 5 | R | Q | R + Q | R + Q + W + Y | R + Q + F + W + Y |
| (SEQ ID NO: 1) | Y | R | Y | R | Q | 2 | 1 | 3 | 2 | 5 |
| (SEQ ID NO: 18) | F | R | Q | R | G | 2 | 1 | 3 | 1 | 4 |
| (SEQ ID NO: 14) | R | Y | R | Q | R | 3 | 1 | 4 | 1 | 5 |
| (SEQ ID NO: 15) | R | Y | S | Q | R | 2 | 1 | 3 | 1 | 4 |
| (SEQ ID NO: 16) | F | R | Q | R | Q | 2 | 2 | 4 | 1 | 5 |
| (SEQ ID NO: 17) | R | Q | R | Q | R | 3 | 2 | 5 | 0 | 5 |
| (SEQ ID NO: 19) | Q | R | Q | R | Q | 2 | 3 | 5 | 0 | 5 |
| (SEQ ID NO: 20) | Y | K | Y | R | Q | 1 | 1 | 2 | 2 | 4 |
| (SEQ ID NO: 21) | Q | Y | R | Q | R | 2 | 2 | 4 | 1 | 5 |

TABLE 6-continued

| SEQ ID NO: | amino acid position | | | | | amino acid count | | | | |
|---|---|---|---|---|---|---|---|---|---|---|
| | 1 | 2 | 3 | 4 | 5 | R | Q | R+Q | F+W+Y | R+Q+F+W+Y |
| (SEQ ID NO: 32) | Y | R | Q | S | R | 2 | 1 | 3 | 1 | 4 |
| (SEQ ID NO: 33) | L | R | Y | R | Q | 2 | 1 | 3 | 1 | 4 |
| (SEQ ID NO: 34) | Y | R | Q | R | A | 2 | 1 | 3 | 1 | 4 |
| (SEQ ID NO: 35) | V | R | Y | R | Q | 2 | 1 | 3 | 1 | 4 |
| (SEQ ID NO: 36) | Q | R | Q | T | R | 2 | 2 | 4 | 0 | 4 |
| (SEQ ID NO: 37) | Y | R | Q | T | R | 2 | 1 | 3 | 1 | 4 |
| (SEQ ID NO: 38) | P | R | Y | R | Q | 2 | 1 | 3 | 1 | 4 |
| (SEQ ID NO: 39) | R | F | S | Q | R | 2 | 1 | 3 | 1 | 4 |
| (SEQ ID NO: 40) | W | Q | R | Q | R | 2 | 2 | 4 | 1 | 5 |
| (SEQ ID NO: 41) | V | R | Q | R | Q | 2 | 2 | 4 | 0 | 4 |
| (SEQ ID NO: 42) | R | Y | T | Q | R | 2 | 1 | 3 | 1 | 4 |
| (SEQ ID NO: 43) | A | Y | R | Q | R | 2 | 1 | 3 | 1 | 4 |
| (SEQ ID NO: 44) | Y | Q | R | Q | R | 2 | 2 | 4 | 1 | 5 |

TABLE 7

| SEQ ID NO: | amino acid position | | | | | amino acid count | | | | |
|---|---|---|---|---|---|---|---|---|---|---|
| | 1 | 2 | 3 | 4 | 5 | K | Y | R | S | K+Y+R+S |
| (SEQ ID NO: 2) | R | Y | E | S | K | 1 | 1 | 1 | 1 | 4 |
| (SEQ ID NO: 25) | R | Y | S | K | Y | 1 | 2 | 1 | 1 | 5 |
| (SEQ ID NO: 26) | A | Y | R | T | K | 1 | 1 | 1 | 0 | 3 |
| (SEQ ID NO: 27) | R | Y | R | S | K | 1 | 1 | 2 | 1 | 5 |
| (SEQ ID NO: 28) | R | Y | G | K | S | 1 | 1 | 1 | 1 | 4 |
| (SEQ ID NO: 29) | Y | K | G | R | G | 1 | 1 | 1 | 0 | 3 |
| (SEQ ID NO: 30) | A | R | S | K | L | 1 | 0 | 1 | 1 | 3 |
| (SEQ ID NO: 45) | N | Y | R | F | K | 1 | 1 | 1 | 0 | 3 |
| (SEQ ID NO: 46) | Y | Q | K | W | K | 2 | 1 | 0 | 0 | 3 |
| (SEQ ID NO: 47) | Y | K | Y | K | Y | 2 | 3 | 0 | 0 | 5 |
| (SEQ ID NO: 48) | R | W | K | F | K | 2 | 0 | 1 | 0 | 3 |
| (SEQ ID NO: 49) | R | F | Y | S | K | 1 | 1 | 1 | 1 | 4 |
| (SEQ ID NO: 50) | Y | K | Y | A | K | 2 | 2 | 0 | 0 | 4 |
| (SEQ ID NO: 51) | Y | R | Y | A | K | 1 | 2 | 1 | 0 | 4 |
| (SEQ ID NO: 52) | R | Y | S | Y | K | 1 | 2 | 1 | 1 | 5 |
| (SEQ ID NO: 53) | Y | K | S | F | K | 2 | 1 | 0 | 1 | 4 |
| (SEQ ID NO: 54) | Y | K | S | W | K | 2 | 1 | 0 | 1 | 4 |
| (SEQ ID NO: 55) | K | Y | R | Y | K | 2 | 2 | 1 | 0 | 5 |
| (SEQ ID NO: 56) | Y | K | Y | N | K | 2 | 2 | 0 | 0 | 4 |
| (SEQ ID NO: 57) | P | Y | K | Y | K | 2 | 2 | 0 | 0 | 4 |
| (SEQ ID NO: 58) | F | Y | K | Y | K | 2 | 2 | 0 | 0 | 4 |
| (SEQ ID NO: 59) | F | Y | E | S | K | 1 | 1 | 0 | 1 | 3 |

Turning first to Table 6, twenty-two 5-mer peptide sequences identified as acyl-donor substrates for KalbTG are listed using the one-letter amino acid code along with information including amino acid position (numbered from N-terminus to C-terminus) and amino acid counts for both individual amino acids (R and Q) and groups of amino acids (R+Q, F+W+Y, and R+Q+F+W+Y). In one aspect, for the KalbTG, the data revealed that an acyl-donor substrate including a 5-mer amino acid sequence having the formula $Xaa_1$-$Xaa_2$-$Xaa_3$-$Xaa_4$-$Xaa_5$, where Xaa is any amino acid, generally complied with several design rules. First, each 5-mer sequence included at least one glutamine (Q). More particularly, at least one of the third, fourth, and fifth positions of the 5-mer sequence (i.e., $Xaa_3$, $Xaa_4$, and $Xaa_5$) was a glutamine. Notably, sequences having two or more adjacent glutamines were generally not observed. However, several sequences were observed that included a glutamine at each of the third and fifth positions. In another aspect, the observation was made that each 5-mer sequence included at least one arginine (R). More particularly, at least one of the fourth and fifth positions of the 5-mer sequence (i.e., $Xaa_4$ and Xaa$_5$) was an arginine. For example, for each of the twenty-two sequences analyzed, an arginine was found in either (but not both) of the fourth or fifth positions. Further, the observation was made that when the fifth position was an arginine, at least one additional arginine was located in one of the first, second, and third positions of the 5-mer sequence (i.e., Xaa$_1$, Xaa$_2$, and Xaa$_3$).

In yet another aspect, the 5-mer sequences each included at least one arginine sequentially adjacent to a glutamine. For example, the 5-mer sequence FRQRG (SEQ ID NO: 8) includes a glutamine at the third position that is flanked by arginines located at both of the second and fourth positions, while the 5-mer sequence YRYRQ (SEQ ID NO: 1) includes an arginine at the fourth position followed sequentially by a glutamine in the fifth position. In addition to the presence of at least one arginine and at least one glutamine in the each of the 5-mer sequences, an amino acid having an aromatic side chain (i.e., phenylalanine, tryptophan, and tyrosine) was found to be present in many of the 5-mer sequences. In particular, the observation was made that the total number of positions occupied by an arginine, glutamine, phenylalanine, tryptophan, or tyrosine in each of the 5-mer sequences was at least four (see last column in Table 6—amino acid count for R+Q+F+W+Y). For example, the 5-mer sequence FRQRG (SEQ ID NO: 8) includes a glutamine, two arginines, and a phenylalanine for a total of four positions occupied by an amino acid selected from arginine, glutamine, phenylalanine, tryptophan, and tyrosine. In another example the 5-mer sequence YRYRQ (SEQ ID NO: 1) includes two arginines, two phenylalanines, and a glutamine for a total of five positions occupied by an amino acid selected from arginine, glutamine, phenylalanine, tryptophan, and tyrosine. Notably, 5-mer sequences lacking an aromatic amino acid include at least four total amino acids selected from arginine and glutamine (e.g., QRQRQ (SEQ ID NO: 19), QRQTR (SEQ ID NO: 36)).

With reference to Table 7, twenty-two 5-mer peptide sequences identified as amine-donor substrates for KalbTG are listed using the one-letter amino acid code along with information including amino acid position (numbered from N-terminus to C-terminus) and amino acid counts for both individual amino acids (K Y, R, S) and a group of amino acids (K+Y+R+S). Similar to the data obtained for the acyl-donor sequences in Table 6, for KalbTG, an amine-donor substrate including a 5-mer amino acid sequence having the formula Xaa$_1$-Xaa$_2$-Xaa$_3$-Xaa$_4$-Xaa$_5$, where Xaa is any amino acid, generally complied with several design rules. First, each 5-mer sequence included at least one lysine (K). More particularly, at least one of the fourth and fifth positions of each 5-mer sequence was a lysine with the single exception being the 5-mer sequence YKGRG (SEQ ID NO: 29). Notably, sequences having two or more adjacent lysines were generally not observed. While several 5-mer sequences were observed that included two total lysines, 5-mer sequences having more than two lysines were not found amongst the analyzed 5-mer sequences. In another aspect, the observation was made that most 5-mer sequences included at least one tyrosine (Y) with the only two exceptions of the twenty-two sequences in Table 7 being RWKFK (SEQ ID NO: 48) and ARSKL (SEQ ID NO: 30).

After the amino acids lysine and tyrosine, the next most frequently occurring amino acids that appeared in the 5-mer sequences in Table 7 were arginine and serine, with at least one arginine or serine present in many of the 5-mer sequences. In particular, the observation was made that the total number of positions occupied by a lysine, tyrosine, arginine, or serine in each of the 5-mer sequences was at least three (see last column in Table 7-amino acid count for K+Y+R+S). For example, the 5-mer sequence NYRFK (SEQ ID NO: 45) includes a tyrosine, an arginine, and a lysine for a total of three positions occupied by an amino acid selected from lysine, tyrosine, arginine, and serine. In another example the 5-mer sequence RYRSK (SEQ ID NO: 27) includes two arginines, a tyrosine, a serine, and a lysine for a total of five positions occupied by an amino acid selected from lysine, tyrosine, arginine, and serine.

Notably, all 5-mer sequences included at least two total amino acids selected from lysine, tyrosine, and either arginine or serine. For example, ARSKL (SEQ ID NO:30) includes one lysine, one arginine, one serine, and no tyrosine. Accordingly, the total number of amino acids selected from lysine, tyrosine, and arginine is two, and the total number of amino acids selected from lysine, tyrosine, and serine is also two. Of course, the total number of positions occupied by a lysine, tyrosine, arginine, or serine in the 5-mer sequences ARSKL (SEQ ID NO:30) is at least three, as discussed above. In a related aspect, 5-mer sequences having both a lysine and at least one of the amino acids tyrosine and arginine include at least two total amino acids selected from lysine, tyrosine, and arginine (e.g., ARSKL (SEQ ID NO:30), FYESK (SEQ ID NO:59)). Moreover, each of the 5-mer sequences included at least one tyrosine or arginine at one of positions one and two (i.e., Xaa$_1$ and Xaa$_2$).

The schematic flow charts shown in the Figures are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed in the Figures are provided to explain the logical steps of the method and are understood not to limit the scope of the method. Although various arrow types and line types may be employed, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention is presented in several varying embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail

Example 7

Figure 8:
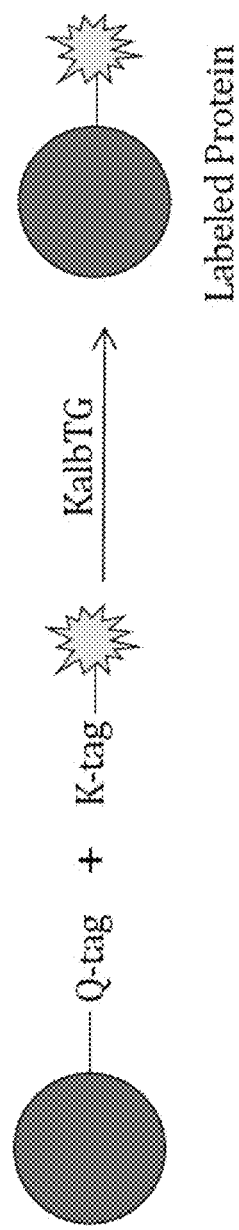
FIG. 8 shows the *Kutzneria albida* transglutaminase catalyzing the formation of an isopeptide bond between a glutamine side chain and a lysine side chain.

Generation of Protease-Resistant Stable Substrates of Microbial Transglutaminases The discovery of novel transglutaminases, such as *Kutzneria albida* transglutaminase (KalbTG) and the identification of highly-enzyme-specific peptide substrates are described herein (see, also, Steffen, et al., "Discovery of a microbial transglutaminase enabling highly site-specific labeling of proteins," J. Biol. Chem. 292(38):15622-15635 (2017), which is incorporated herein by reference). *Kutzneria albida* transglutaminases catalyze the formation of an isopeptide bond between a glutamine side chain and a lysine side chain, as shown in FIG. 8. As described herein, YRYRQ (SEQ ID NO:1) was identified as an excellent highly-specific Gln-motif (Q-tag) substrate of *Kutzneria albida* transglutaminase, and RYESK (SEQ ID NO:2) was identified as an excellent highly-specific Lys-motif (K-tag) substrate of *Kutzneria albida* transglutaminases.

Figure 9A:
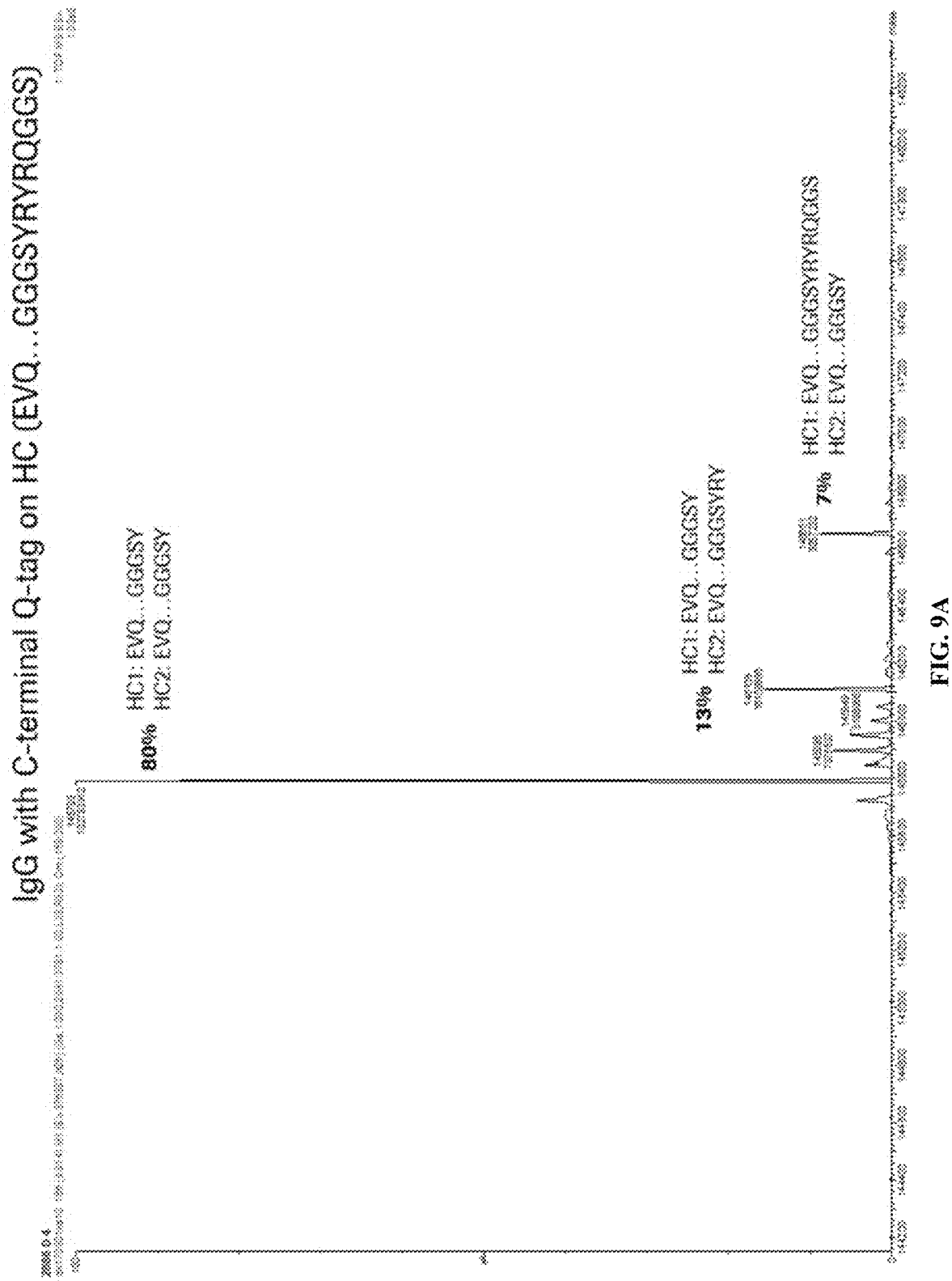
FIG. 9A shows mass spectrometry data, showing clipping/degradation products of the C-terminus YRYRQ (SEQ ID NO:1) Q-tag after the first or the second ˆ of the tag (Y'RY'RQ) on either one or both heavy chains, as evidenced by the three different significant populations of molecules with different clipping/degradation pattern combinations, as described in Example 7.

Some of the described Q-tag substrates for *Kutzneria albida* transglutaminase show clipping/degradation as an unwanted side produced during the mammalian cell fermentation process of the proteins bearing these tags. This clipping/degradation is likely caused by cell proteases. This results in a subpopulation of truncated products, which lack the target glutamine (Q), and therefore lack the ability to be conjugated to a Lys-motif (K-tag) substrate by the action of *Kutzneria albida* transglutaminase. Moreover, the stability of these protease-susceptible Q-tag substrates was also highly buffer-dependent, wherein these protease-susceptible Q-tag substrates show a loss in signal (likely due to the clipping/degradation of the tag and the subsequent loss of label attachment), following stress in application buffer. FIGS. 9A and 9B depict mass spectrometry data and assay performance data, respectively.

By way of example, an antibody, IgG, was tagged at its C-terminus of its heavy chain with a Q-tag substrate with GGGSYRYRQGGGS (SEQ ID NO:104), which bears the Q-containing sequence YRYRQ (SEQ ID NO:1). Thus, the substrate tag GGGSYRYRQGGGS (SEQ ID NO:104) comprises the Q-tag YRYRQ (SEQ ID NO:1), but with linkers GGGS (SEQ ID NO:116) attached to both sides of it. Following IgG production in mammalian HEK293 cells, and one-step purification (Protein affinity chromatography), a sample was subject to Mass Spectrometry (MS) analysis. The Mass Spectrometry data show clipping/degradation products of the C-terminus YRYRQ (SEQ ID NO:1) Q-tag after the first or the second Y of the tag (Y'RY'RQ) on either one or both heavy chain. Three different significant populations of molecules with different clipping/degradation pattern combinations were detected, as shown in FIG. 9A.

Antibody portions, Fab and IgG, which were tagged in the C-terminus of their heavy chain regions with Q-tags (GGGYRYRQGGGP (SEQ ID NO:105) for Fab and GGGSYRYRQGGGS (SEQ ID NO:106) for IgG, each of which contain the Q-containing sequence YRYRQ (SEQ ID NO:1) sequence), were then conjugated with biotin via action of *Kutzneria albida* transglutaminase. Thus, the substrate tag GGGYRYRQGGGP (SEQ ID NO:105) comprises the Q-tag YRYRQ (SEQ ID NO:1) with linkers GGG (SEQ ID NO:119) and GGGP (SEQ ID NO:118) attached to either side. Similarly, the substrate tag GGGSYRYRQGGGS (SEQ ID NO:106) comprises the Q-tag YRYRQ (SEQ ID NO:1) with linkers GGGS (SEQ ID NO:116) attached to both of its sides. Conjugates were tested as capture antibodies in an ElectroChemiLuminescence Immunoassay on an Elecsys E170 analyzer in the respective assay buffer using calibrator 2 of the respective assay. Conjugates were then stressed for seven days at 35° C., Elecsys measurements repeated, and percentage signal recovery was calculated as compared to original sales lot of the same assay. The data/results, shown in FIG. 9B, which show, after seven days, only 35% recovery of the Fab with heavy chain C-terminal GGGYRYRQGGGP and only 10% recovery of the IgG with heavy chain C-terminal GGGYRYRQGGGS. Thus, these data also show significant clipping/degradation of the Fab- or IgG-conjugated Q-tag substrates over time.

Subsequent studies were conducted in order to identify Q-tag substrates that do not exhibit the tag-clipping/degradation within cell culture or assay buffer. That is, subsequent studies were conducted in order to identify protease-resistant and more stable Q-tag substrates. These studies (as shown in FIGS. 10-16) show the successful identification and characterization of protease-resistant stable Q-tag substrates. The absence of tyrosine (Y) within the 5-mer Q-tag sequence seems to be the determining factor of its protease resistant properties. That is, the absence of Y in the 5-mer Q-tag sequence appears to render the Q-tag substrate resistant to protease-mediated clipping/degradation and thereby rending it more stable.

Figure 10:
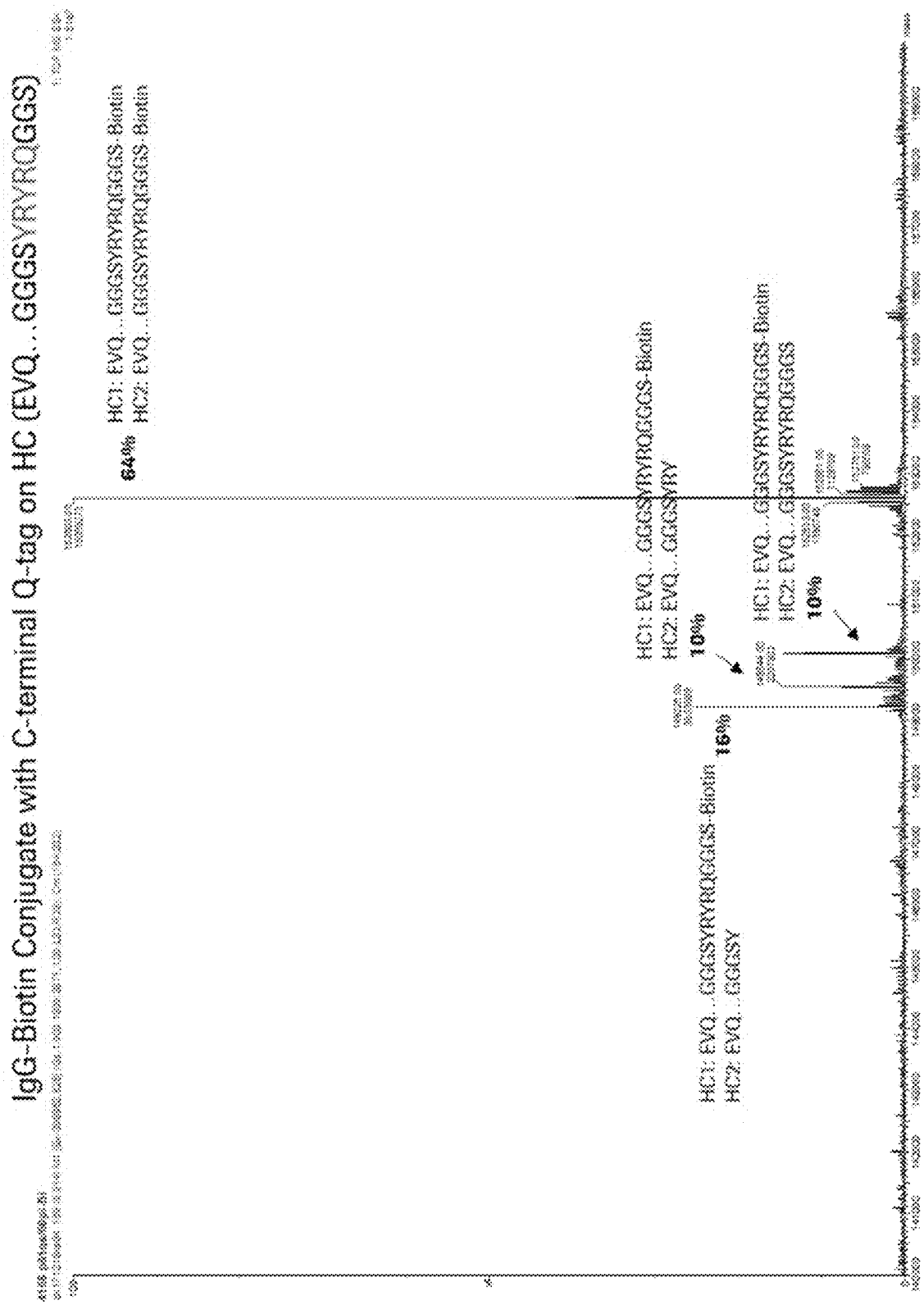
FIG. 10 depicts mass spectrometry data showing data showing clipping/degradation products of the C-terminal YRYRQ (SEQ ID NO:1) Q-tag after the first or the second Y of the tag (Y'RY'RQ) on the heavy chain. This clipping/degradation resulted in the loss of the Q, which is required for conjugation to a Lys-motif (K-tag) substrate, and hence, an unconjugated heavy chain. Different significant populations of molecules with different clipping/degradation patterns combinations (resulting in single biotin conjugation) were detected. These data show that only 64% of product is the expected IgG double conjugated at the C-terminus of each heavy chain with biotin.

In one study, IgG tagged at the C-terminus of its heavy chain with Q-tag substrate, GGGSYRYRQGGGS (SEQ ID NO:106), which contains the Q-containing sequence YRYRQ (SEQ ID NO:1) sequence within, was employed. Thus, the substrate tag GGGSYRYRQGGGS (SEQ ID NO:106) comprises the Q-tag YRYRQ (SEQ ID NO:1), with the linker GGGS (SEQ ID NO:116) attached to both of its sides. Following IgG production in mammalian HEK293 cells and one-step purification (Protein A affinity chromatography), IgG was then conjugated with biotin using *Kutzneria albida* transglutaminase, purified in a single-step by size-exclusion chromatography (which removes excess label). A sample was then subjected to Mass Spectrometry (MS) analysis. MS data shows clipping/degradation products of the C-terminal YRYRQ (SEQ ID NO:1) Q-tag after the first or the second Y of the tag (Y'RY'RQ) on the heavy chain. This clipping/degradation resulted in the loss of the Q, which is required for conjugation to a Lys-motif (K-tag) substrate, and hence, an unconjugated heavy chain. Different significant populations of molecules with different clipping/degradation patterns combinations (resulting in single biotin conjugation) were detected. These data show that only 64% of product is the expected IgG double conjugated at the C-terminus of each heavy chain with biotin. These data/results are shown in FIG. 10.

Figure 11:
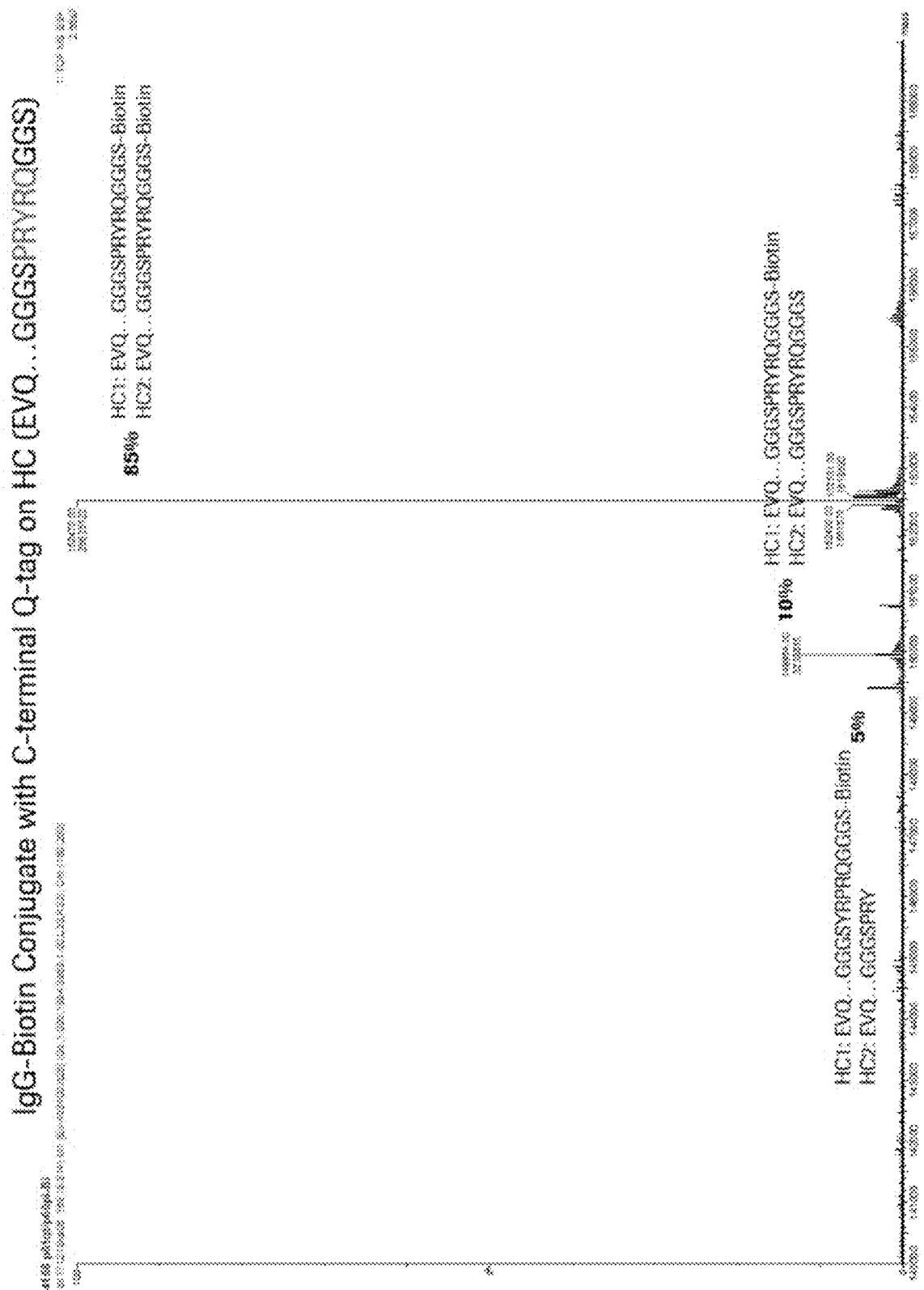
FIG. 11 depicts mass spectrometry data showing clipping/degradation products of the C-terminal PRYRQ (SEQ ID NO:38) Q-tag after the Y of the tag (PRY'RQ) on the heavy chain. This clipping/degradation resulted in the loss of the conjugatable Q in the tag and hence unconjugated heavy chain. Significant populations of molecules with different clipping/degradation (resulting in single biotin conjugation) or with full-length, but unconjugated Q-tag, were detected. These results show that only 85% of product is the expected IgG double conjugated at the C-terminus of each heavy chain with biotin.

In another example, IgG tagged at the C-terminus of its heavy chain with Q-tag substrate, GGGSPRYRQGGGS (SEQ ID NO:107), which contained the Q-containing PRYRQ sequence (SEQ ID NO:38) within, was employed. Thus, the substrate tag GGGSPRYRQGGGS (SEQ ID NO:107) comprises the Q-tag PRYRQ (SEQ ID NO:38), with the linker GGGS (SEQ ID NO:116) attached to both of its sides. Following IgG production in mammalian HEK293 cells and one-step purification (Protein A affinity chromatography), IgG was then conjugated with biotin using *Kutzneria albida* transglutaminase, purified in a single-step by size-exclusion chromatography (removes excess label). A sample was then subject to Mass Spectrometry (MS) analysis. MS data shows clipping/degradation products of the C-terminal PRYRQ (SEQ ID NO:38) Q-tag after the Y of the tag (PRY'RQ) on the heavy chain. This clipping/degradation resulted in the loss of the conjugatable Q in the tag and hence unconjugated heavy chain. Significant populations of molecules with different clipping/degradation (resulting in single biotin conjugation) or with full-length, but unconjugated Q-tag, were detected. These results show that only 85% of product is the expected IgG double conjugated at the C-terminus of each heavy chain with biotin, as depicted in FIG. 11.

Figure 12:
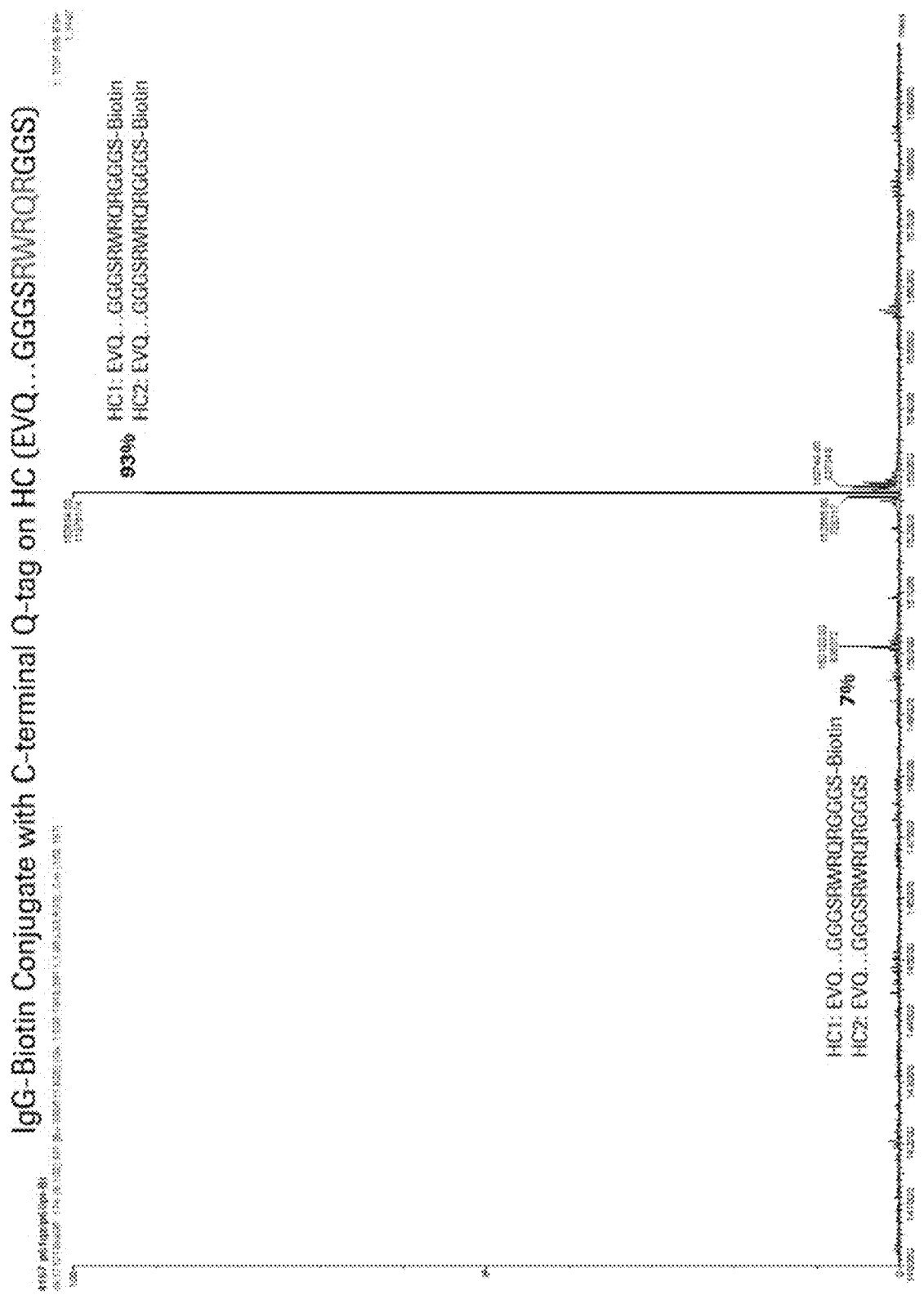
FIG. 12 depicts mass spectrometry data showing no clipping/degradation products of the C-terminal RWRQR (SEQ ID NO:112) Q-tag. Two significant populations of molecules were detected: (1) one with both heavy chains conjugated with biotin and (2) another with only one conjugated Q-tag (but in both cases full-length Q-tags were detected at C-terminus). These data show that 93% of product is the expected IgG double conjugated at the C-terminus of each heavy chain with biotin.

In another example, IgG tagged at the C-terminus of its heavy chain with Q-tag substrate, GGGSRWRQRGGGS (SEQ ID NO:108), which contained the Q-containing sequence RWRQR (SEQ ID NO:112) within, was employed. Thus, the substrate tag GGGSRWRQRGGGS (SEQ ID NO:108) comprises the Q-tag RWRQR (SEQ ID NO:112), with linker GGGS (SEQ ID NO:116) attached to both of its sides. Following IgG production in mammalian HEK293 cells and one-step purification (Protein A affinity chromatography), IgG was then conjugated with biotin using *Kutzneria albida* transglutaminase, purified in a single-step by size-exclusion chromatography (removes excess label). A sample was then subjected to Mass Spectrometry (MS) analysis. MS data shows no clipping/degradation products of the C-terminal RWRQR (SEQ ID NO:112) Q-tag. Two significant populations of molecules were detected: (1) one with both heavy chains conjugated with biotin and (2) another with only one conjugated Q-tag (but in both cases full-length Q-tags were detected at C-terminus). These data show that 93% of product is the expected IgG double conjugated at the C-terminus of each heavy chain with biotin, as shown in FIG. 12.

Figure 13:
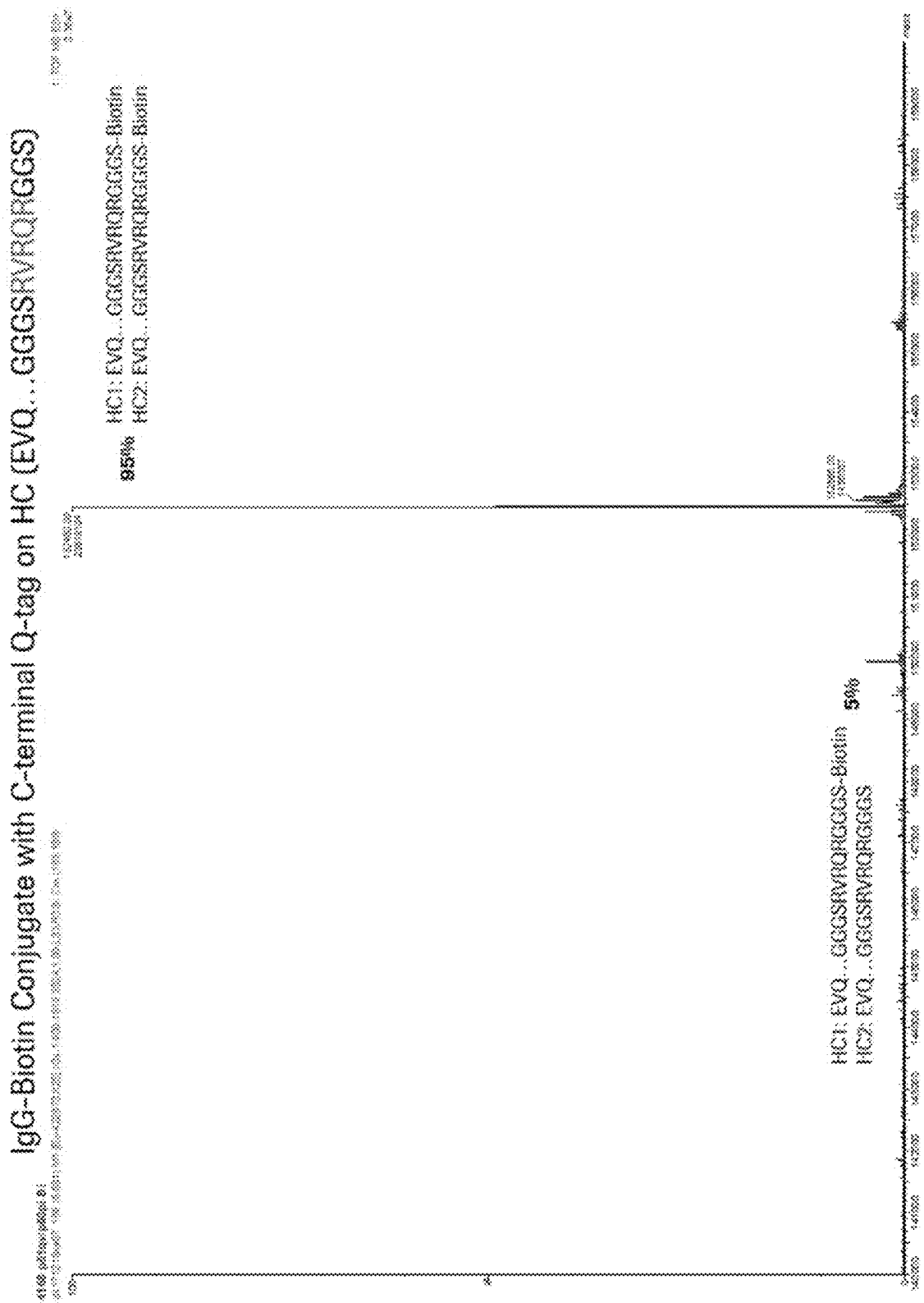
FIG. 13 depicts mass spectrometry data showing no clipping/degradation products of the C-terminal RVRQR (SEQ ID NO:113) Q-tag. Two significant populations of molecules were detected: (1) one with both heavy chains conjugated with biotin, and (2) the second with only one conjugated Q-tag (but in both cases full-length Q-tags are detected at C-terminus). These results show that 95% of product is the expected IgG double conjugated at the C-terminus of each heavy chain with biotin.

In another example, IgG tagged at the C-terminus of its heavy chain with Q-tag substrate, GGGSRVRQRGGGS (SEQ ID NO:109), which contained the Q-containing 5-mer RVRQR (SEQ ID NO:113) within, was employed. Thus, the substrate tag GGGSRVRQRGGGS (SEQ ID NO:109) comprises the Q-tag RVRQR (SEQ ID NO:113), with linker GGGS (SEQ ID NO:116) attached to both of its sides. Following IgG production in mammalian HEK293 cells and one-step purification (Protein A affinity chromatography), IgG was then conjugated with biotin using *Kutzneria albida* transglutaminase, purified in a single-step by size-exclusion chromatography (removes excess label). A sample was then subjected to analysis by Mass Spectrometry (MS). The MS data shows no clipping/degradation products of the C-terminal RVRQR (SEQ ID NO:113) Q-tag. Two significant populations of molecules were detected: (1) one with both heavy chains conjugated with biotin, and (2) the second with only one conjugated Q-tag (but in both cases full-length Q-tags are detected at C-terminus). These results show that 95% of product is the expected IgG double conjugated at the C-terminus of each heavy chain with biotin, as shown in FIG. 13.

Figure 14:
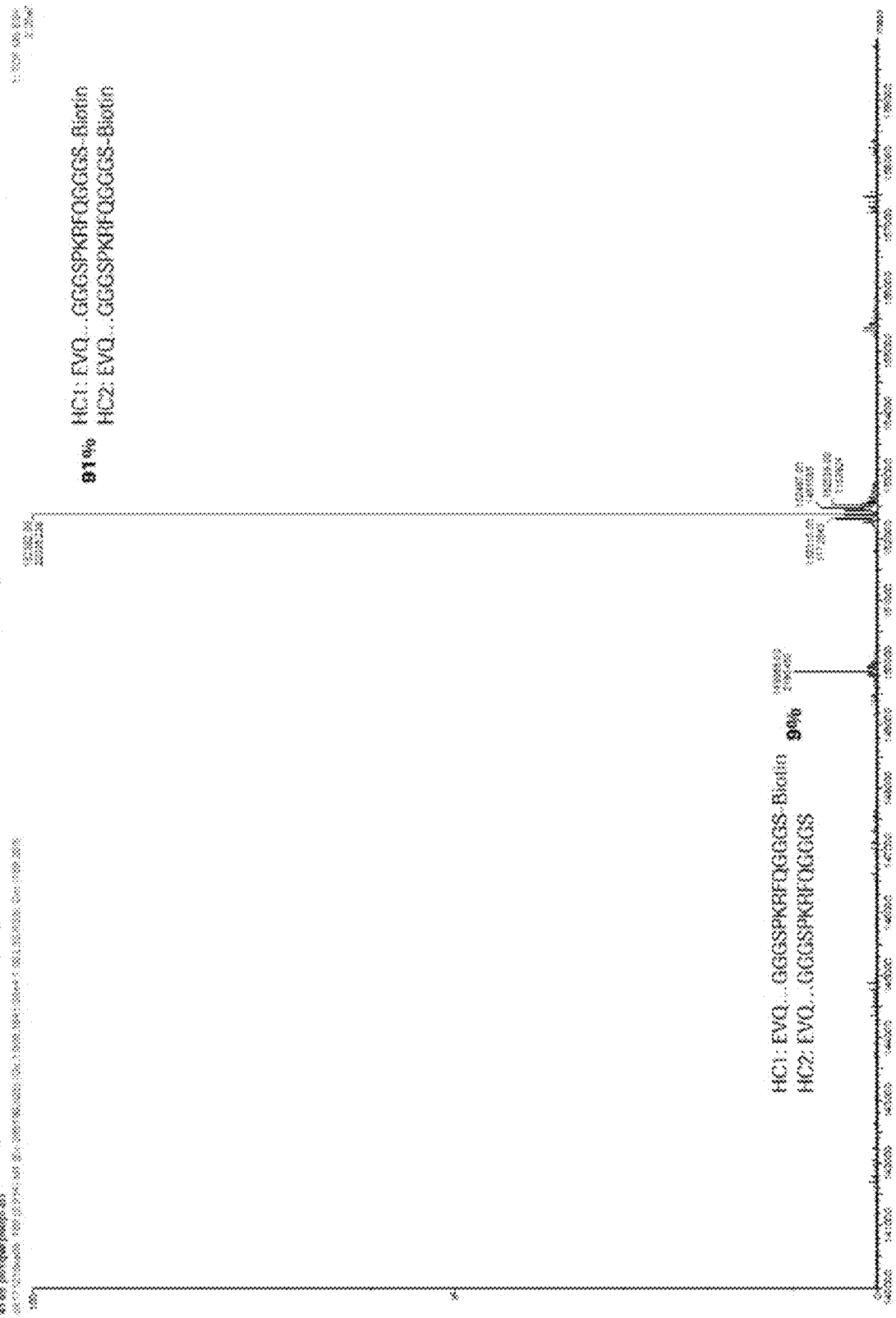
FIG. 14 depicts mass spectrometry data showing shows no clipping/degradation products of the C-terminal PKFRQ (SEQ ID NO:114) Q-tag. Two significant populations of molecules were detected: (1) one with both heavy chains conjugated with biotin, and (2) one with only one conjugated Q-tag (but in both cases full-length Q-tags are detected at C-terminus) (see, FIG. 14). These results show that 91% of product is the expected IgG double conjugated at the C-terminus of each heavy chain with biotin.

In another example, IgG tagged at the C-terminus of its heavy chain with Q-tag substrate, GGGSPKFRQGGGS (SEQ ID NO:110), which contained the Q-containing 5-mer tag PKFRQ (SEQ ID NO:114) within, was employed. Thus, the substrate tag GGGSPKFRQGGGS (SEQ ID NO:110) comprises the Q-tag PKFRQ (SEQ ID NO:114), with linker GGGS (SEQ ID NO:116) attached to both of its sides. Following IgG production in mammalian HEK293 cells and one-step purification (Protein A affinity chromatography), IgG was then conjugated with biotin using *Kutzneria albida* transglutaminase, purified in a single-step by size-exclusion chromatography (removes excess label). Then, a sample was subjected to analysis by Mass Spectrometry (MS). The MS data shows no clipping/degradation products of the C-terminal PKFRQ (SEQ ID NO:114) Q-tag. Two significant populations of molecules were detected: (1) one with both heavy chains conjugated with biotin, and (2) one with only one conjugated Q-tag (but in both cases full-length Q-tags are detected at C-terminus) (see, FIG. 14). These results show that 91% of product is the expected IgG double conjugated at the C-terminus of each heavy chain with biotin, as depicted in FIG. 14.

Figure 15:
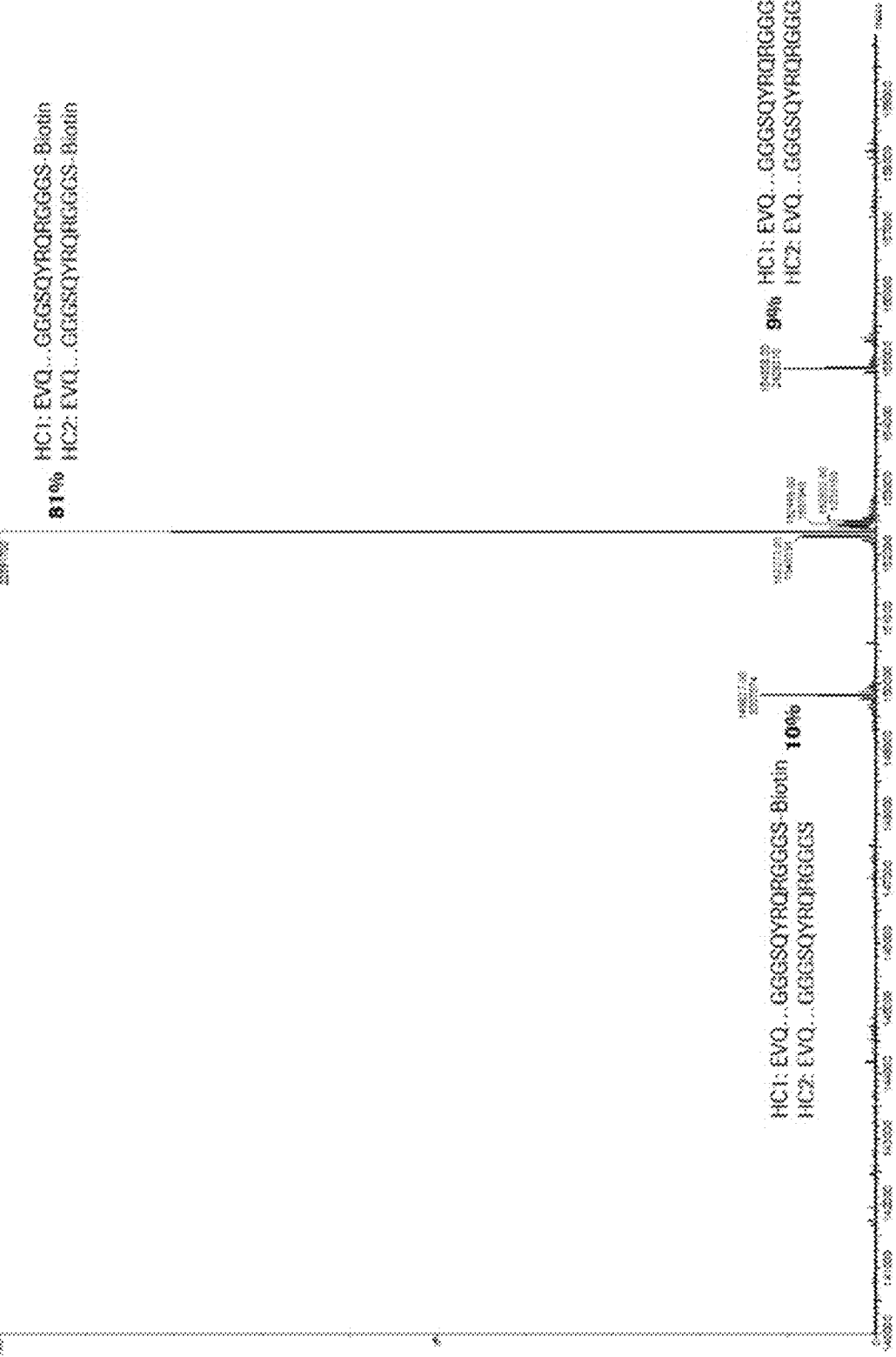
FIG. 15 depicts mass spectrometry data showing no clipping/degradation products of the C-terminal PKQRQ (SEQ ID NO:115) Q-tag. Three significant populations of molecules are detected: (1) one with both heavy chains conjugated with biotin, (2) a second with only one conjugated Q-tag, and (3) a third with one heavy chain carrying two biotins (two conjugatable Q per tag). In all cases full-length Q-tags are detected at C-terminus. These data show that 81% of product is IgG double conjugated at the C-terminus of each heavy chain with biotin.

In another example, IgG tagged at the C-terminus of its heavy chain with Q-tag substrate, GGGSPKQRQGGGS (SEQ ID NO:111), which contained the Q-containing 5-mer, PKQRQ (SEQ ID NO:115) within, was employed. Thus, the substrate tag GGGSPKQRQGGGS (SEQ ID NO:111) comprises the Q-tag PKQRQ (SEQ ID NO:115) with linker GGGS (SEQ ID NO:116) attached to both of its sides. Following IgG production in mammalian HEK293 cells and one-step purification (Protein A affinity chromatography), IgG was then conjugated with biotin using *Kutzneria albida* transglutaminase, purified in a single-step by size-exclusion chromatography (removes excess label). A sample was then subjected to analysis by Mass Spectrometry (MS). The MS data shows no clipping/degradation products of the C-terminal PKQRQ (SEQ ID NO:115) Q-tag. Three significant populations of molecules are detected: (1) one with both heavy chains conjugated with biotin, (2) a second with only one conjugated Q-tag, and (3) a third with one heavy chain carrying two biotins (two conjugatable Q per tag). In all cases full-length Q-tags are detected at C-terminus (see, FIG. 15). These data show that 81% of product is IgG double conjugated at the C-terminus of each heavy chain with biotin, as shown in FIG. 15.

In another example, IgGs with C-terminal tagging of heavy chain with different Q-tag substrate, either GGGYRYRQGGGP (SEQ ID NO:105) or GGGSRVRQRGGGS (SEQ ID NO:109), were conjugated with biotin using *Kutzneria albida* transglutaminase. The substrate tag GGGYRYRQGGGP (SEQ ID NO:105) comprises the Q-tag YRYRQ (SEQ ID NO:1), with the linkers GGG (SEQ ID NO:119) and GGGP (SEQ ID NO:118) attached to either side. Similarly, the substrate tag GGGSRVRQRGGGS (SEQ ID NO:109) comprises the Q-tag RVRQR (SEQ ID NO:113), with the linker GGGS (SEQ ID NO:116) attached to both of its sides. Conjugates were tested on Elecsys E170 analyzer in the respective assay buffer using calibrator 2 of the respective assay. Conjugates were then stressed for seven days at 35° C. Elecsys measurements were repeated and amount of signal recovery (reflected as a percentage) was calculated compared to an original sales lot rackpack of the same assay. IgG with C-terminal RVRQR (SEQ ID NO:113) show superior stability in tested Elecsys buffer compared to those with YRYRQ (SEQ ID NO:1), as shown in FIG. 16.

Q-tag substrates must be inserted within the sequence of target biomolecules in order to achieve site-specific conjugate using *Kutzneria albida* transglutaminase. These Examples demonstrate that the use of protease-resistant and stable substrates assures the production of stable homogeneous biomolecules that can be efficiently conjugated for diagnostic or pharmaceutical applications.

What is claimed is:

1. A structure, a microbial transglutaminse, a first substrate tag, and a second substrate tag,
   wherein the first substrate tag is attached to the structure;
   wherein the first substrate tag comprises an acyl-donor tag, wherein the acyl-donor tag consists of the peptide sequence of RVRQR (SEQ ID NO:113);
   wherein the second substrate tag comprises an amine-donor tag;
   wherein the structure is selected from a recombinant protein, a detectable label, and a chemically synthesized structure;
   wherein the microbial transglutaminase has at least 80% sequence identity to the *Kutzneria albida* microbial transglutaminase (SEQ ID NO:6); and
   wherein the microbial transglutaminase cross-links the first substrate tag to the second substrate tag by forming an isopeptide bond between the acyl-donor tag and the amine-donor tag.

2. The structure, the microbial transglutaminase, the first substrate tag, and the second substrate tag of claim 1, wherein the detectable label is selected from a biotin moiety, a fluorescent dye, a ruthenium label, a radiolabel, and a chemiluminescent label.

3. The structure, the microbial transglutaminase, the first substrate tag, and the second substrate tag of claim 1, wherein the recombinant microbial transglutaminase is the *Kutzneria albida* microbial transglutaminase (SEQ ID NO:6).

4. The structure, the microbial transglutaminase, the first substrate tag, and the second substrate tag of claim 1, wherein the chemically synthesized structure comprises at least one of a protein, a peptide, an oligonucleotide, a carboxybenzyl group, and a polyethylene glycol (PEG) polymer.

5. The structure, the microbial transglutaminase, the first substrate tag, and the second substrate tag of claim 1, wherein the amine-donor tag has a peptide sequence of RYESK (SEQ ID NO:2).

6. The structure, the microbial transglutaminase, the first substrate tag, and the second substrate tag of claim 1, wherein the amine-donor tag is attached to a second structure, wherein the second structure is selected from a second recombinant protein, a second detectable label, and a second chemically synthesized structure.

7. The structure, the microbial transglutaminase, the first substrate tag, and the second substrate tag of claim 6, wherein the second detectable label is selected from a biotin moiety, a fluorescent dye, a ruthenium label, a radiolabel, and a chemiluminescent label.

8. The structure, the microbial transglutaminase, the first substrate tag, and the second substrate tag claim 6, wherein the second chemically synthesized structure comprises at least one of a protein, a peptide, an oligonucleotide, a carboxybenzyl group, and a polyethylene glycol (PEG) polymer.

9. The structure, the microbial transglutaminase, the first substrate tag, and the second substrate tag of claim 1, wherein the first substrate tag and/or the second substrate tag is flanked on the N-terminus, on the C-terminus, or both the N-terminus and C-terminus with a linker.

10. The structure, the microbial transglutaminase, the first substrate tag, and the second substrate tag of claim 9, wherein the linker is a 3 amino acid long linker or a 4 amino acid long linker.

11. The structure, the microbial transglutaminase, the first substrate tag, and the second substrate tag of claim 10, wherein the linker is synthesized by using a mixture of glycine and serine having a 3:1 ratio.

12. The structure, the microbial transglutaminase, the first substrate tag, and the second substrate tag of claim 11, wherein the linker consists of the sequence GGGS (SEQ ID NO:116).

13. The structure, the microbial transglutaminase, the first substrate tag, and the second substrate tag of claim 10, wherein the linker is synthesized by using a mixture of glycine and proline having a 3:1 ratio.

14. The structure, the microbial transglutaminase, the first substrate tag, and the second substrate tag of claim 13, wherein the linker consists of the sequence GGGP (SEQ ID NO:118).

15. The structure, the microbial transglutaminase, the first substrate tag, and the second substrate tag of claim 10, wherein the linker consists of the sequence GGG (SEQ ID NO:119).

16. A kit for forming an isopeptide bond in the presence of a microbial transglutaminase, the kit comprising an isolated microbial transglutaminase having at least 80% sequence identity to the *Kutzneria albida* microbial transglutaminase (SEQ ID NO:6), and a first substrate, wherein the first substrate comprises an acyl-donor tag, wherein the acyl-donor tag consists of the peptide sequence of RVRQR (SEQ ID NO:113).

17. The kit of claim 16, further comprising a second substrate, wherein the second substrate comprises an amine-donor tag having at least 80% sequence identity to the peptide sequence RYESK (SEQ ID NO:2).

18. The kit of claim 17, wherein at least one of the first substrate and the second substrate includes a detectable label.

19. The kit of claim 18, wherein the detectable label is selected from a biotin moiety, a fluorescent dye, a ruthenium label, and a chemiluminscent label.

20. The kit of claim 17, further comprising the other one of the first substrate and the second substrate.

21. A structure, a substrate tag attached to the structure, and a microbial transglutaminase bound to the substrate tag, wherein the substrate tag comprises an acyl-donor tag having the peptide sequence of RVRQR (SEQ ID NO:113), wherein the acyl-donor tag is a substrate for the microbial transglutaminase, wherein the structure is selected from a recombinant protein, a detectable label, and a chemically synthesized structure, and wherein the microbial transglutaminase has at least 80% sequence identity to the *Kutzneria albida* microbial transglutaminase (SEQ ID NO:6).

22. The structure of claim 21, wherein the detectable label is selected from a biotin moiety, a fluorescent dye, a ruthenium label, a radiolabel, and a chemiluminescent label.

23. The structure of claim 21, wherein the recombinant microbial transglutaminase is the *Kutzneria albida* microbial transglutaminase (SEQ ID NO:6).

24. The structure of claim 21, wherein the chemically synthesized structure comprises at least one of a protein, a peptide, an oligonucleotide, a carboxybenzyl group, and a polyethylene glycol (PEG) polymer.

25. The structure of claim 21, wherein the microbial transglutaminase is further bound to an amine-donor tag.

26. The structure of claim 25, wherein the amine-donor tag has a peptide sequence consisting of RYESK (SEQ ID NO:2).

27. The structure of claim 26, wherein the amine-donor tag is attached to a second structure, wherein the second structure is selected from a second recombinant protein, a second detectable label, and a second chemically synthesized structure.

28. The structure of claim 27, wherein the second detectable label is selected from a biotin moiety, a fluorescent dye, a ruthenium label, a radiolabel, and a chemiluminescent label.

29. The structure of claim 27, wherein the second chemically synthesized structure comprises at least one of a protein, a peptide, an oligonucleotide, a carboxybenzyl group, and a polyethylene glycol (PEG) polymer.

30. The structure, the microbial transglutaminase, the first substrate tag, and the second substrate tag of claim 1, wherein the acyl-donor tag has the peptide sequence of GGGSRVRQRGGGS (SEQ ID NO:109).

31. The kit of claim 17, wherein the acyl-donor tag has the peptide sequence of GGGSRVRQRGGGS (SEQ ID NO:109).

* * * * *